US011137401B2

(12) United States Patent
Okano et al.

(10) Patent No.: US 11,137,401 B2
(45) Date of Patent: Oct. 5, 2021

(54) METHOD FOR DETECTING CANCER USING CAPRIN-1 AS A MARKER

(75) Inventors: Fumiyoshi Okano, Kanagawa (JP); Kana Suzuki, Kanagawa (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 13/057,515

(22) PCT Filed: Aug. 5, 2009

(86) PCT No.: PCT/JP2009/063883
§ 371 (c)(1), (2), (4) Date: Feb. 4, 2011

(87) PCT Pub. No.: WO2010/016527
PCT Pub. Date: Feb. 11, 2010

(65) Prior Publication Data

US 2011/0136121 A1 Jun. 9, 2011

(30) Foreign Application Priority Data

Aug. 5, 2008 (JP) ............................. JP2008-202320

(51) Int. Cl.
*G01N 33/574* (2006.01)
*C12Q 1/6886* (2018.01)

(52) U.S. Cl.
CPC ..... *G01N 33/57415* (2013.01); *C12Q 1/6886* (2013.01); *G01N 33/57407* (2013.01); *C12Q 2600/112* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,552,293 | A | 9/1996 | Lindholm et al. | |
| 5,698,396 | A | 12/1997 | Pfreundschuh | |
| 6,335,170 | B1 | 1/2002 | Orntoft | |
| 6,444,425 | B1 | 9/2002 | Reed et al. | |
| 7,449,184 | B2 | 11/2008 | Allison et al. | |
| 7,485,302 | B2 | 2/2009 | Adams et al. | |
| 7,745,391 | B2 | 6/2010 | Mintz et al. | |
| 8,008,431 | B2 | 8/2011 | Weinschenk et al. | |
| 8,211,634 | B2 * | 7/2012 | DePinho | A61P 43/00 435/6.14 |
| 8,709,418 | B2 | 4/2014 | Okano et al. | |
| 8,828,398 | B2 | 9/2014 | Kobayashi et al. | |
| 8,911,740 | B2 | 12/2014 | Saito et al. | |
| 8,937,160 | B2 | 1/2015 | Kobayashi et al. | |
| 9,115,200 | B2 | 8/2015 | Okano et al. | |
| 9,175,074 | B2 | 11/2015 | Okano et al. | |
| 9,180,187 | B2 | 11/2015 | Ido et al. | |
| 9,180,188 | B2 | 11/2015 | Kobayashi et al. | |
| 9,181,334 | B2 | 11/2015 | Kobayashi et al. | |
| 9,181,348 | B2 | 11/2015 | Kobayashi et al. | |
| 9,260,513 | B2 | 2/2016 | Kobayashi et al. | |
| 9,266,958 | B2 | 2/2016 | Kobayashi et al. | |
| 9,273,128 | B2 | 3/2016 | Okano et al. | |
| 9,273,130 | B2 | 3/2016 | Kobayashi et al. | |
| 9,409,993 | B2 | 8/2016 | Minamida et al. | |
| 9,416,191 | B2 | 8/2016 | Kobayashi et al. | |
| 9,416,192 | B2 | 8/2016 | Okano et al. | |
| 9,416,193 | B2 | 8/2016 | Saito et al. | |
| 9,428,581 | B2 | 8/2016 | Saito et al. | |
| 9,573,993 | B2 | 2/2017 | Okano et al. | |
| 9,753,038 | B2 | 9/2017 | Ido et al. | |
| 9,772,332 | B2 | 9/2017 | Ido et al. | |
| 9,862,774 | B2 | 1/2018 | Okano et al. | |
| 9,982,059 | B2 | 5/2018 | Okano et al. | |
| 2003/0118599 | A1 | 6/2003 | Algate et al. | |
| 2003/0190640 | A1 | 10/2003 | Faris et al. | |
| 2004/0029114 | A1 | 2/2004 | Mack et al. | |
| 2004/0236091 | A1 | 11/2004 | Chicz et al. | |
| 2004/0258678 | A1 | 12/2004 | Bodary et al. | |
| 2005/0003390 | A1 * | 1/2005 | Axenovich | C12Q 1/6886 435/5 |
| 2005/0032113 | A1 | 2/2005 | Tanaka et al. | |

(Continued)

FOREIGN PATENT DOCUMENTS

| | | | |
|---|---|---|---|
| CA | 2788720 | A1 | 8/2011 |
| CN | 1678338 | A | 10/2005 |

(Continued)

OTHER PUBLICATIONS

HUGO Human Gene Nomenclature Committee, "CAPRIN1" printed Nov. 3, 2012.*
R&D Systems "IHC Products & Protocol Guide" (printed Jan. 9, 2014).*
NCBI Reference Sequence: NP_005889 for human CAPRIN-1, printed Apr. 2017.*
European Search Report No. 09 80 5010 dated Aug. 26, 2011 issued for corresponding International Application PCT/JP2009/063883.
International Search Report, dated Sep. 8, 2009, issued in corresponding International Application PCT/JP2009/063883.
Katsafanas et al., "Colocalization of Transcription and Translation within Cytoplasmic Poxvirus Factories Coordinates Viral Expression and Subjugates Host Functions", Ceil Host & Microbe, Oct. 2007, vol. 2, No. 4, pp. 221-228.

(Continued)

*Primary Examiner* — Laura B Goddard
(74) *Attorney, Agent, or Firm* — Birch, Stewart, Kolasch & Birch, LLP

(57) ABSTRACT

The present invention relates to a method for detecting cancer, comprising measuring the expression of a polypeptide having a reactivity of binding to an antibody against a CAPRIN-1 protein having an amino acid sequence shown in any one of the even-numbered SEQ ID NOS: 2-30 in the Sequence Listing via an antigen-antibody reaction in a sample separated from a living organism, and, a reagent for detecting a cancer comprising the CAPRIN-1 protein or a fragment thereof, an antibody against the CAPRIN-1 protein or a fragment thereof, or a polynucleotide encoding the CAPRIN-1 protein or a fragment thereof.

16 Claims, 4 Drawing Sheets

Specification includes a Sequence Listing.

(56) References Cited

U.S. PATENT DOCUMENTS

| | | | |
|---|---|---|---|
| 2005/0129690 | A1 | 6/2005 | Bowdish et al. |
| 2005/0244413 | A1 | 11/2005 | Guenther et al. |
| 2006/0019256 | A1 | 1/2006 | Clarke et al. |
| 2006/0069054 | A1 | 3/2006 | Houghton et al. |
| 2006/0275305 | A1 | 12/2006 | Bryant |
| 2007/0048301 | A1 | 3/2007 | Bodary-Winter et al. |
| 2007/0083334 | A1 | 4/2007 | Mintz et al. |
| 2007/0154931 | A1 | 7/2007 | Radich et al. |
| 2008/0075722 | A1 | 3/2008 | DePinho et al. |
| 2008/0107668 | A1 | 5/2008 | Philip et al. |
| 2008/0161293 | A1 | 7/2008 | Yoshinaga et al. |
| 2008/0306018 | A1 | 12/2008 | Croce et al. |
| 2010/0029573 | A1 | 2/2010 | Weinschenk et al. |
| 2010/0068724 | A1 | 3/2010 | Fung et al. |
| 2011/0123492 | A1 | 5/2011 | Okano et al. |
| 2011/0136121 | A1 | 6/2011 | Okano et al. |
| 2011/0189700 | A1 | 8/2011 | Moses et al. |
| 2011/0256144 | A1 | 10/2011 | Okano et al. |
| 2012/0171699 | A1 | 7/2012 | Goodman et al. |
| 2012/0214975 | A1 | 8/2012 | Sandig et al. |
| 2012/0294860 | A1 | 11/2012 | Ido et al. |
| 2012/0301471 | A1 | 11/2012 | Kobayashi et al. |
| 2012/0301476 | A1 | 11/2012 | Okano et al. |
| 2012/0321641 | A1 | 12/2012 | Okano et al. |
| 2013/0045210 | A1 | 2/2013 | Kobayashi et al. |
| 2013/0071398 | A1 | 3/2013 | Saito et al. |
| 2014/0154261 | A1 | 6/2014 | Okano et al. |
| 2014/0178373 | A1 | 6/2014 | Kobayashi et al. |
| 2014/0186359 | A1 | 7/2014 | Okano et al. |
| 2014/0193434 | A1 | 7/2014 | Kobayashi et al. |
| 2014/0199311 | A1 | 7/2014 | Kobayashi et al. |
| 2014/0308283 | A1 | 10/2014 | Minamida et al. |
| 2015/0004171 | A1 | 1/2015 | Kobayashi et al. |
| 2015/0017172 | A1 | 1/2015 | Kobayashi et al. |
| 2015/0044221 | A1 | 2/2015 | Kobayashi et al. |
| 2015/0050283 | A1 | 2/2015 | Okano et al. |
| 2015/0218285 | A1 | 8/2015 | Saito et al. |
| 2016/0297889 | A1 | 10/2016 | Okano et al. |

FOREIGN PATENT DOCUMENTS

| | | | |
|---|---|---|---|
| CN | 1705876 | A | 12/2005 |
| CN | 101120252 | A | 2/2006 |
| CN | 101189516 | A | 5/2008 |
| CN | 101836116 | A | 9/2010 |
| CN | 102170907 | A | 8/2011 |
| CN | 102171570 | A | 8/2011 |
| EP | 1557172 | A1 | 7/2005 |
| EP | 2 207 037 | A1 | 7/2010 |
| EP | 2270149 | A2 | 1/2011 |
| EP | 2 325 648 | A1 | 5/2011 |
| EP | 2322221 | | 5/2011 |
| EP | 2 532 367 | A1 | 12/2012 |
| EP | 2 532 743 | A1 | 12/2012 |
| EP | 2 740 794 | A1 | 6/2014 |
| EP | 2 832 365 | A1 | 2/2015 |
| EP | 2 832 366 | A1 | 2/2015 |
| JP | 2002-540790 | A | 12/2002 |
| JP | 2003-528587 | A | 9/2003 |
| JP | 2006-316040 | A | 11/2006 |
| JP | 2013-502205 | A | 1/2013 |
| JP | 2013-505028 | A | 2/2013 |
| RU | 2161042 | C2 | 12/2000 |
| RU | 2234942 | C2 | 2/2003 |
| RU | 2244720 | C2 | 1/2005 |
| RU | 2306952 | C2 | 9/2007 |
| RU | 2319709 | C2 | 3/2008 |
| RU | 2006137060 | A | 4/2008 |
| RU | 2391982 | C2 | 6/2010 |
| WO | WO 96/09551 | A1 | 3/1996 |
| WO | WO 00/04149 | A2 | 1/2000 |
| WO | WO 00/05268 | A1 | 2/2000 |
| WO | WO 00/60077 | A2 | 10/2000 |
| WO | WO 01/32910 | A2 | 5/2001 |
| WO | WO 01/72295 | A2 | 10/2001 |
| WO | WO 02/078524 | A2 | 10/2002 |
| WO | WO 02/083070 | A2 | 10/2002 |
| WO | WO 02/092001 | A2 | 11/2002 |
| WO | WO 03/007889 | A2 | 1/2003 |
| WO | WO 2004/076682 | * | 9/2004 |
| WO | WO 2004/076682 | A2 | 9/2004 |
| WO | WO 2004/097051 | A2 | 11/2004 |
| WO | WO 2005/007830 | A2 | 1/2005 |
| WO | WO2005/100998 | * | 10/2005 |
| WO | WO 2005/100998 | A2 | 10/2005 |
| WO | WO 2005/116051 | A2 | 12/2005 |
| WO | WO 2005/116076 | A2 | 12/2005 |
| WO | WO 2006/002378 | A2 | 1/2006 |
| WO | WO 2007/150077 | A2 | 12/2007 |
| WO | WO 2008/031041 | A2 | 3/2008 |
| WO | WO 2008/059252 | A2 | 5/2008 |
| WO | WO 2008/073162 | A2 | 6/2008 |
| WO | WO 2008/088583 | A2 | 7/2008 |
| WO | WO 2009/113742 | A1 | 9/2009 |
| WO | WO 2009/117277 | A2 | 9/2009 |
| WO | WO 2010/016525 | A1 | 2/2010 |
| WO | WO 2010/016526 | A1 | 2/2010 |
| WO | WO 2010/016527 | A1 | 2/2010 |
| WO | WO 2011/096517 | A1 | 8/2011 |
| WO | WO 2011/096519 | A1 | 8/2011 |
| WO | WO 2011/096528 | A1 | 8/2011 |
| WO | WO 2011/096533 | A1 | 8/2011 |
| WO | WO 2011/096534 | A1 | 8/2011 |
| WO | WO 2011/096535 | A1 | 8/2011 |
| WO | WO 2012/005550 | A2 | 1/2012 |
| WO | WO 2012/013609 | A1 | 2/2012 |
| WO | WO 2013/018885 | A1 | 2/2013 |
| WO | WO 2013/018886 | A1 | 2/2013 |
| WO | WO 2013/018894 | A1 | 2/2013 |
| WO | WO 2013/147169 | A1 | 10/2013 |
| WO | WO 2013/147176 | A1 | 10/2013 |

OTHER PUBLICATIONS

Solomon et al., "Distinct Structural Features of Caprin-1 Mediate Its Interaction with G3BP-1 and Its Induction of Phosphorylation of Eukaryotic Translation Initiation Factor 2alpha, Entry to Cytoplasmic Stress Granules, and Selective Interaction with a Subset of mRNAs", Molecular and Cellular Biology, Mar. 2007, vol. 27, No. 6, pp. 2324-2342.

Akiyoshi, "Cancer Vaccine Therapy Using Peptides Derived from Tumor-rejection Antigens," Jpn. J. Cancer Chemother., vol. 24, No. 5, Mar. 1997, pp. 511-519, with English Abstract (p. 519).

Bodey et al., "Failure of Cancer Vaccines: The Significant Limitations of this Approach to Immunotherapy," Anticancer Research, vol. 20, 2000, pp. 2665-2676.

Brass et al., "Translation initiation factor eIF-4gamma is encoded by an amplified gene and induces an immune response in squamous cell lung carcinoma," Human Molecular Genetics, vol. 6, No. 1, 1997, pp. 33-39.

Chamberlain et al., "Innovations and strategies for the development of anticancer vaccines," Expert Opinion on Pharmacotherapy, vol. 1, No. 4, 2000, pp. 603-614.

Ellis et al., "Identification and Characterization of a Novel Protein (p137) Which Transcytoses Bidirectionally in Caco-2 Cells," The Journal of Biological Chemistry, vol. 270, No. 35, Sep. 1, 1995, pp. 20717-20723.

Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.

Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.

Gure et al., "SSX: A Multigene Family with Several Members Transcribed in Normal Testis and Human Cancer," Int. J. Cancer, vol. 72,1997, pp. 965-971.

Itoh et al., "HUB1 is an autoantigen frequently eliciting humoral immune response in patients with adult T cell leukemia," Int. J. Oncol., vol. 14, 1999, pp. 703-708 (Abstract only provided).

(56) References Cited

OTHER PUBLICATIONS

Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.
Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Katsafanas et al., "Vaccinia Virus Intermediate Stage Transcription is Complemented by Ras-GTPase-activating Protein SH3 Domain-binding Protein (G3BP). . . ," Jour. of Biol. Chem., vol. 279, No. 50, Dec. 10, 2004, p. 52210-52217.
Kolobova et al., "Microtubule-dependent association of AKAP350A and CCAR1 with RNA stress granules," Experimental Cell Research, vol. 315, 2009 (Available online Dec. 3, 2008), pp. 542-555.
Lu et al., "Identification of an immunological signature of tumor rejection in the neu transgenic mouse," 2007 AACR Annual Meeting, Proceedings Abstract No. 4131, Apr. 14-18, 2007 (Presentation conducted on Apr. 17, 2007) (Abstract only provided).
Müller-Pillasch et al., "Identification of a new tumour-associated antigen TM4SF5 and its expression in human cancer," Gene, vol. 208, 1998, pp. 25-30.
Rauch et al., "SEREX, Proteomex, AMIDA, and beyond: Serological screening technologies for target identification," Proteomics Clin. Appl., vol. 2, 2008, pp. 355-371.
Sahin et al., "Human neoplasms elicit multiple specific immune responses in the autologous host," Proc. Natl. Acad. Sci. USA, vol. 92, Dec. 1995, p. 11810-11813.
Scanlan et al., "Characterization of Human Colon Cancer Antigens Recognized by Autologous Antibodies," Int. J. Cancer, vol. 76, 1998, pp. 652-658.
Türeci et al., "The SSX-2 Gene, Which is Involved in the t(X; 18) Translocation of Synovial Sarcomas, Codes for the Human Tumor Antigen HOM-MEL-40," Cancer Research, vol. 56, Oct. 15, 1996, pp. 4766-4772.
Van Der Bruggen et al., "A Gene Encoding an Antigen Recognized by Cytolytic T Lymphocytes on a Human Melanoma," Science, vol. 254, No. 5038, Dec. 13, 1991, pp. 1643-1647 (Also published in J. Immunol., vol. 178, 2007, pp. 2617-2621).
Wang et al., "Absence of Caprin-1 Results in Defects in Cellular Proliferation," The Journal of Immunology, vol. 175, 2005, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92 (Abstract only provided).
GeneCards, "Cell Cycle Associated Protein 1—Biological research products for CAPRIN 1", updated Mar. 19, 2013, 10 pages.
Karauzum et al., "Caprin 1 is Frequently Overexpressed in Human Lymphomas," American Society of Human Genetics, Cancer Genetics, Program No. 1190W, Oct. 12, 2011, Abstract only.
United States Office Action, dated Jul. 1, 2013, for U.S. Appl. No. 13/577,212.
United States Office Action, dated Jul. 16, 2013, for U.S. Appl. No. 13/057,709.
Chinese Office Action dated Mar. 29, 2013 for Chinese Application No. 200980139037.
Lu et al., "Targeting serum antibody for cancer diagnosis: a focus on colorectal cancer," Oncologic, Endocrine & Metabolic, Expert Opinion on Therapeutic Targets, vol. 11, No. 2, Feb. 2007, pp. 235-244.
NCBI Reference Sequence, caprin-1 [Bos taurus], Feb. 23, 2013, Accession No. NP001069530, XP615677, 1 page.
NCB Reference Sequence, caprin-1 [Gallus galius], Feb. 22, 2013, Accession No. NP001026536, XP423820, 1 page.
NCBI Reference Sequence, caprin-1 isoform 1 [*Homo sapiens*], Mar. 17. 2013, Accession No. NP005889, 3 pages.
NCBI Reference Sequence, caprin-1 isoform 2 [*Homo sapiens*], Mar. 3, 2013, Accession No. NP976240, 3 pages.
NCBI Reference Sequence, caprin-1 isoform a [Mus musculus], Mar. 23, 2013, Accession No. NP058019, 3 pages.
NCBI Reference Sequence, caprin-1 isoform b [Mus musculus], Mar. 23, 2013. Accession No. NP001104760, 3 pages.
NCBI Reference Sequence, caprin-1 isoform c [Mus musculus]. Mar. 23, 2013, Accession No. NP001104761,4 pages.
NCBI Reference Sequence, Predicted: caprin-1 [Equus cabalius], Jun. 27, 2011, Accession No. XP001492799, 1 page.
NCBI Reference Sequence, Predicted: caprin-1 isoform 2 [Canis lupus famillaris], Dec. 2, 2011, i Accession No. XP858109, 1 page.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Chinese Office Action for Chinese Application No. 201180016730.5 dated May 9, 2013.
European Search Report for European Application No. 11739882.6 dated Aug. 13. 2013.
Evans et al., "Vaccine therapy for cancer—fact or fiction?", Q. J. Med., vol. 92, 1999, pp. 299-307.
Harlow et al., Antibodies A Laboratory Manual, Cold Spring Harbor Laboratory, Chapter 3, pp. 23-34, Cold Spring Harbor, New York, 11724, 1988.
Munodzana et al., "Conformational Dependence of Anaplasma Marginale Major Surface Protein 5 Surface-Exposed B-Cell Epitopes", Infection and Immunity, vol. 86, No. 6, Jun. 1998, pp. 2619-2624.
Office Action for U.S. Appl. No. 13/576,959 dated Oct. 15, 2013.
Office Action for U.S. Appl. No. 13/577,212 dated Oct. 21. 2013.
Okano et al., "Identfication of a novel target for antibody therapy of breast cancer", Cancer Research, vol. 72, No. 8, Apr. 15, 2012.
Polyak et al., "Alanin-170 and proline-172 are critical determinants tor extracellular CD20 epitopes; heterogeneity in the fine specificity of CD20 monoclonal antibodies is defined by additional requirements . . . ", Blood, vol. 99, No. 9, pp. 3256-3262, 2002.
Russian Notice of AJlowance for Russian Application No. 20111108260 dated Jun. 7, 2013.
Balmaña et al., "BRCA in breast cancer: ESMO Clinical Recommendations," Annals of Oncology (Supp 4):iv19-iv20, 2009.
Brand et al., "Prospect for Anti-HER2 Receptor Therapy in Breast Cancer," Anticancer Research 26:463-470 (2006).
European Search Report received Nov. 5, 2013 in European Patent Application 11739876.8.
Kataja and Castiglione, "Primary breast cancer: ESMO Clinical Recommendations for diagnosis, treatment and follow-up" Annals of Oncology 20 (Supp 4); iv10-iv14 2009.
Nelson et al., "Screening for Breast Cancer: An Update for the U.S. Preventive Services Task Force," Ann. Intern. Med. 2009;151:727-737.
Office Action dated Nov. 15, 2013 in U.S. Appl. No. 13/577,028, including Notice of References Cited.
Office Action dated Nov. 15, 2013, in U.S. Appl. No. 13/576,950, including Notice of References Cited.
Strome et al. "A Mechanistic Perspective of Monoclonal Antibodies in Cancer Therapy Beyond Target-Related Effects," The Oncologist 2007;12:1084-1095.
Russian Notice of Allowance, dated Jan. 24, 2014, for Russian Application No. 2011108258.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol. (2002), vol. 169, pp. 3076-3084.
Extended European Search Report dated Mar. 2, 2015, in European Patent Application No. 12819759.7.
Gong et al., "Caprin-1 is a novel microRNA-223 target for regulating the proliferation and invasion of human breast cancer cells," Biomedicine & Pharmacotherapy (2013), vol. 67, pp. 629-636.
Office Action dated Jan. 28, 2015, in Russian Patent Application No. 2012137502, with partial English translation.

(56) References Cited

OTHER PUBLICATIONS

Qui et al., "Targeting a ribonucleoprotein complex containing the caprin-1 protein and the c-Myc mRNA suppresses tumor growth in mice: an identification of a novel oncotarget," Oncotarget (2014), vol. 6, No. 4, pp. 2148-2163.
Riechmann et al., "Reshaping human antibodies for therapy," Nature (Mar. 24, 1988), vol. 332, pp. 323-327.
Sabile et al., "Caprin-1, a novel Cyr61-interacting protein, promotes osteosarcoma tumor growth and lung metastasis in mice," Biochimica et Biophysica Acta (2013), vol. 1832, pp. 1173-1182.
Vajdos et al,. "Comprehensive Functional Maps of the Antigen-bining Site of an Anti-ErbB2 Antibody Obtained with Shotgun Scanning Mutagenesis," J. Mol. Biol. (2002), vol. 320, pp. 415-428.
Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.
Chames et al., "Therapeutic Antibodies for the Treatment of Pancreatic Cancer," The Scientific World Journal (Jan. 1, 2010), vol. 10, pp. 1107-1120.
Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.
Esteva et al., "Chemotheraphy of Metastatic Breast Cancer: What to Expect in 2001 and Beyond," The Oncologist (2001), vol. 6, pp. 133-146.
Extended European Search Report dated Feb. 2, 2015, in European Patent Application No. 12819473.5.
Extended European Search Report dated Jan. 29, 2015, in European Patent Application No. 12819899.1.
Houghton, P. J. and J. A. Houghton, "Evaluation of Single-Agent Therapy in Human Colorectal Tumour Xenografts," Br. J. Cancer (1978), vol. 37, pp. 833-840.
Office Action dated Jan. 27, 2015, in Japanese Patent Application No. 2011-510197.
GenBack Accession No. NM_0405898, Feb. 11, 2008.
Office Action dated Sep. 28, 2014, in Chinese Patent Application No. 201280038464.0.
Bodey et al., "MAGE-1, a Cancer/Testis-Antigen, Expression tn Childhood Astrocytomas as an Indicator of Tumor Progression," in vivo (2002) vol. 16, pp. 583-588.
Corntesse et al., "Probing the human natural autoantibody repertoire using an immunoscreening approach," Clin. Exp. Immunol. (2000), vol. 121, p. 430-436.
International Search Report dated Nov. 18, 2014, in PCT International Application No. PCT/JP2014/071094.
Jager et al., "Identification of a Tissue-specific Putative Transcription Factor in Breast Tissue by Serological Screening of a Breast Cancer Library," Cancer Research (Mar. 1, 2001), vol. 61, pp. 2055-2061.
Jungbluth et al., "Immunohistochemical Analysis of NY-ESO-1 Antigen Expression in Normal and Malignant Human Tissues," Int. J. Cancer (2001), vol. 92, pp. 856-860.
Kohler et al., "Tumor antigen analysis in neuroblastoma by serological interrogation of bioinformatic data," Cancet Science (Nov. 2010). vol. 101, No. 11, pp. 2316-2324.
Nakamura et al. "Gene Expression profile of Metastatic Human Pancratic Cancer Cells Depends on the Organ Microenvironment," Cancer Research (Jan. 1, 2007), vol. 67, No. 1, pp. 139-148.
Non-Final Office Action dated Nov. 6, 2014. in U.S. Appl. No. 13/576,950.
Office Action dated Sep. 28, 2014, in Chinese Patent Application No. 2012080038464.0.
Office Action dated Sep. 29, 2014, in Chinese Patent Application No. 201280038490.3.
Pegram et al., "Rational Combinations of Trastuzumab with Chemotherapeutic Drugs Used in the Treatment of Breast Cancer," Journal of the National Cancer Institute (May 19, 2004), vol. 98, No. 10, pp. 739-749.
Punt et al., "Edrecolomab alone or in combination with fluorouracil and folinic acid in the adjuvant treatment of stage III colon cancer: a randomised study," Lancet (Aug. 31, 2002), vol. 360, No. 3334, pp. 671-677.
GenBank Accession No. AAU93399, Sep. 22, 2005.
GenBank Accession No. EAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_00111291, Feb. 10, 2008.
GenBank Accession No. NM_001111292, Feb. 11, 2008.
GenBank Accession No. NM_016739, Feb. 10, 2008.
GenBank. Accession No. NM_05898, Feb. 11, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.
Patent Examination Report No. 1 dated Oct. 14.2014, in Australian Patent Application No. 2009278387.
U.S. Office Action for U.S. Appl. No. 14/379,867, dated Jun. 24, 2015.
Extended European Search Report dated Mar. 18, 2015, in European Patent Application No. 12820225.6.
Extended European Search Report dated Mar. 23, 2015, in European Patent Application No. 12820596.0.
Non-Final Office Action dated Apr. 14, 2015, in U.S. Appl. No. 14/236,793.
Russian Notice of Allowance for Russian Application No. 2014108049/10, dated May 16, 2016, with an English translation.
Russian Decision on Grant for Russian Application No. 2012137504/10, dated Jun. 22, 2016, with an English translation.
Russian Office Action for Russian Application No. 2014138041/10, dated Jul. 5, 2016, with an English translation.
"*Homo sapiens* cell cycle associated protein 1, mRNA (cDNA clone MGC:1378 Image:3355481), complete cds", Genebank database, NCBI Accession No. BC001731, Sep. 11, 2007.
Carter, Paul J., "Potent antibody therapeutics by design", Nature Reviews Immunology, vol. 6, May 2006, pp. 343-357.
Extended European Search Report for Appl. No. 13820574.5 dated Jan. 11, 2016.
Huang, J. et al., "IgG Isotype Conversion of a Novel Human Anti-carcinoembryonic Antigen Antibody to Increase its Biological Activity," Anticancer Research, 2006, vol. 26, No. 2A, pp. 1057-1063.
Japanese Office Action for Appl. No. 2014-225640 dated Nov. 4, 2015.
Shibaguchi, H. et al, "New Human Antibody IgG Subclass Conversion for Enhancement of Tumor-Cytotoxic Activity," Research, 2006, vol. 11, No. 3, pp. 15-16.
Extended European Search Report for European Application No. 13767612.8, dated Sep. 22, 2015.
Extended European Search Report for European Application No. 13769665.4, dated Sep. 22, 2015.
U.S. Office Action for U.S. Appl. No. 14/415,090, dated May 19, 2016.
U.S. Office Action for U.S. Appl. No. 14/415,520, dated May 19, 2016.
Russian Office Action and Search Report for Russian Application No. 2014143784, dated Jan. 19, 2017, including a partial English translation.
Roitt et al., "NK cells and K cells use several different receptors on the surface, to identify their targets," Immunology, 2000, p. 181 (4 pages), with an English abstract.
Russian Office Action and English translation thereof, dated Apr. 17, 2017, for Russian Application No. 2014143785/10.
U.S. Non-Final Office Action, dated May 15, 2017, for U.S. Appl. No. 15/092,469.
Extended European Search Report dated Feb. 27, 2017, in European Patent Application No. 14834828.7.
Indian Examination Report dated Feb. 23, 2017, in Indian Patent Application No. 960/KOLNP/2011.

(56) References Cited

OTHER PUBLICATIONS

Russian Decision on Grant of Patent for Invention dated Mar. 13, 2017, in Russian Patent Application No. 2012137503, with English translation.
Russian Decision on Grant of Patent for Invention dated Mar. 29, 2017, in Russian Patent Application No. 2014108048, with English translation.
Chinese Office Action and Search Report, dated Jul. 2, 2018, for Chinese Application No. 201480044559.2.
Indian Office Action dated Jul. 30, 2018 for Application No. 2177/KOLNP/2012, with an English translation thereof.
Indian Office Action, dated Jan. 14, 2019, for Indian Application No. 1715/KOLNP/2014, along with an English translation.
Office Action issued in Canadian Patent Application No. 2,844,033 dated Mar. 6, 2019.
Spijker et al., "Stimulated Gene Expression Profiles as a Blood Marker of Major Depressive Disorder", Biol Psychiatry, 68, pp. 179-186, 2010.
Indian Hearing Notice for Indian Application No. 2268/KOLNP/2012, dated Jan. 7, 2020, with English translation.
Shiina et al., "A Novel RNA-Binding Protein in Neuronal RNA Granules: Regulatory Machinery for Local Translation," The Journal of Neuroscience, vol. 25, No. 17, Apr. 27, 2005, pp. 4420-4434.
Edwards et al., "The Remarkable Flexibility of the Human Antibody Repertoire; Isolation of Over One Thousand Different Antibodies to a Single Protein, BLyS", J. Mol. Biol., 334, 2003, pp. 103-118.
Marchalonis et al., "The antibody repertoire in evolution: Chance, selection, and continuity", Developmental and Comparative Immunology, 30, 2006, pp. 223-247.
Non-Final Office Action issued in U.S. Appl. No. 15/971,647 dated Jun. 2, 2020.
U.S. Appl. No. 13/057,709, filed Feb. 4, 2011.
U.S. Appl. No. 13/577,028, filed Aug. 3, 2012.
U.S. Appl. No. 13/576,969, filed Aug. 3, 2012.
U.S. Appl. No. 13/576,955, filed Aug. 3, 2012.
U.S. Appl. No. 13/577,212, filed Aug. 3, 2012.
U.S. Appl. No. 13/576,953, filed Aug. 3, 2012.
U.S. Appl. No. 13/576,950, filed Aug. 3, 2012.
Corada et al., "Monoclonal antibodies directed to different regions of vascular endothelial cadherin extracellular domain affect adhesion and clustering of the protein and modulate endothelial permeability," Blood (Mar. 15, 2001), vol. 97, No. 6, pp. 1679-1684.
Office Action dated Aug. 14, 2015, in U.S. Appl. No. 14/236,818.
Office Action dated Aug. 20, 2015, in U.S. Appl. No. 14/452,746.
Office Action dated Jul. 27, 2015, in Chinese Patent Application No. 201380038386.9.
Office Action dated Jul. 3, 2015, in Russian Patent Application No. 2012137503.
Office Action dated Sep. 15, 2015, in U.S. Appl. No. 14/389,266.
Padlan, E.A., "X-Ray Crystallography of Antibodies," Adv. Prot. Chem. (1996), vol. 49, pp. 57-133.
Saffari et al., "Identification of novel p53 target genes by cDNA AFLP in glioblastoma cells", Cancer Letters, 2009, No. 273, pp. 316-322.

* cited by examiner

Canine normal tissue
Muscle
Lung
Thymus gland
Spleen
Pancreas
Kidney
Liver
Eye
Heart
Testis
Peripheral blood
1
2
Canine breast cancer tissue
A
B
C
D
E
F
1
2
Human breast cancer cell line
A
B
C
D
E
F
G
H
1
2
Human cancer cell line
Brain tumor
A
B
C
D
Leukemia
A
B
C
Lung cancer
Esophageal cancer
A
B
1
2

```
                              SEQUENCE LISTING


<160> NUMBER OF SEQ ID NOS: 63

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)
<223> OTHER INFORMATION:

<400> SEQUENCE: 1

cagagggctg ctggctggct aagtccctcc cgctcccggc tctcgcctca ctaggagcgg     60

ctctcggtgc agcgggacag ggcgaagcgg cctgcgccca cggagcgcgc gacactgccc    120

ggaagggacc gccacccttg ccccctcagc tgcccactcg tgatttccag cggcctccgc    180

gcgcgcacg atg ccc tcg gcc acc agc cac agc ggg agc ggc agc aag tcg    231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
              35                  40                  45

ggc gct gtc cag acc gag gcc atg aag cag att ctc ggg gtg atc gac      375
Gly Ala Val Gln Thr Glu Ala Met Lys Gln Ile Leu Gly Val Ile Asp
          50                  55                  60

aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
      65                  70                  75

cag gaa cga atg aac aaa ggg gaa agg ctt aat caa gat cag ctg gat      471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca      567
Glu Leu Gln Arg Ser Phe Met Ala Leu Ser Gln Asp Ile Gln Lys Thr
              115                 120                 125

ata aag aag aca gca cgt cgg gag cag ctt atg aga gaa gaa gct gaa      615
Ile Lys Lys Thr Ala Arg Arg Glu Gln Leu Met Arg Glu Glu Ala Glu
          130                 135                 140

cag aaa cgt tta aaa act gta ctt gag cta cag tat gtt ttg gac aaa      663
Gln Lys Arg Leu Lys Thr Val Leu Glu Leu Gln Tyr Val Leu Asp Lys
      145                 150                 155

ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190
```

```
aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460

cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca     1719
Ala Gly Thr Ser Lys Pro Leu His Ser Ser Gly Ile Asn Val Asn Ala
```

-continued

```
495                 500                 505                 510

gct cca ttc caa tcc atg caa acg gtg ttc aat atg aat gcc cca gtt     1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag     1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa     1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat     1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct     1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat     2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg     2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt     2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct     2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat     2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc     2247
Gln Gln Asn Phe Lys Arg Gly Ser Gly Gln Ser Gly Pro Arg Gly Ala
                675                 680                 685

cca cga ggt cgt gga ggg ccc cca aga ccc aac aga ggg atg ccg caa     2295
Pro Arg Gly Arg Gly Gly Pro Pro Arg Pro Asn Arg Gly Met Pro Gln
            690                 695                 700

atg aac act cag caa gtg aat taa tctgattcac aggattatgt ttaatcgcca    2349
Met Asn Thr Gln Gln Val Asn
        705

aaaacacact ggccagtgta ccataatatg ttaccagaag agttattatc tatttgttct   2409

ccctttcagg aaacttattg taaagggact gttttcatcc cataaagaca ggactacaat   2469

tgtcagcttt ctattacctg gatatggaag gaaactattt ttactctgca tgttctgtcc   2529

taagcgtcat cttgagcctt gcacatgata ctcagattcc tcacccttgc ttaggagtaa   2589

aacaatatac tttacagggt gataataatc tccatagtta tttgaagtgg cttgaaaaag   2649

gcaagattga cttttatgac attggataaa atctacaaat cagccctcga gttattcaat   2709

gataactgac aaactaaatt atttccctag aaaggaagat gaaaggagtg gagtgtggtt   2769

tggcagaaca actgcatttc acagcttttc cagttaaatt ggagcactga acgttcagat   2829

gcataccaaa ttatgcatgg gtcctaatca cacatataag gctggctacc agctttgaca   2889

cagcactgtt catctggcca aacaactgtg gttaaaaaca catgtaaaat gctttttaac   2949

agctgatact gtataagaca aagccaagat gcaaaattag gctttgattg gcactttttg   3009

aaaaatatgc aacaaatatg ggatgtaatc cggatggccg cttctgtact taatgtgaaa   3069

tatttagata cctttttgaa cacttaacag tttctttgag acaatgactt ttgtaaggat   3129
```

-continued

```
tggtactatc tatcattcct tatgacatgt acattgtctg tcactaatcc ttggattttg   3189
ctgtattgtc acctaaattg gtacaggtac tgatgaaaat ctctagtgga taatcataac   3249
actctcggtc acatgttttt ccttcagctt gaaagctttt ttttaaaagg aaaagatacc   3309
aaatgcctgc tgctaccacc cttttcaatt gctatctttt gaaaggcacc agtatgtgtt   3369
ttagattgat ttccctgttt cagggaaatc acggacagta gtttcagttc tgatggtata   3429
agcaaaacaa ataaaacgtt tataaaagtt gtatcttgaa acactggtgt tcaacagcta   3489
gcagcttatg tgattcaccc catgccacgt tagtgtcaca aattttatgg tttatctcca   3549
gcaacatttc tctagtactt gcacttatta tcttttgtct aatttaacct taactgaatt   3609
ctccgtttct cctggaggca tttatattca gtgataattc cttcccttag atgcataggg   3669
agagtctcta aatttgatgg aaatggacac ttgagtagtg acttagcctt atgtactctg   3729
ttggaatttg tgctagcagt ttgagcacta gttctgtgtg cctaggaagt taatgctgct   3789
tattgtctca ttctgacttc atggagaatt aatcccacct ttaagcaaag gctactaagt   3849
taatggtatt ttctgtgcag aaattaaatt ttattttcag catttagccc aggaattctt   3909
ccagtaggtg ctcagctatt taaaaacaaa actattctca aacattcatc attagacaac   3969
tggagttttt gctggttttg taacctacca aaatggatag gctgttgaac attccacatt   4029
caaaagtttt gtagggtggt gggaaatggg ggatcttcaa tgtttatttt aaaataaaat   4089
aaaataagtt cttgactttt ctcatgtgtg gttgtggtac atcatattgg aagggttaac   4149
ctgttacttt ggcaaatgag tatttttttg ctagcacctc cccttgcgtg ctttaaatga   4209
catctgcctg ggatgtacca caaccatatg ttacctgtat cttaggggaa tggataaaat   4269
atttgtggtt tactgggtaa tccctagatg atgtatgctt gcagtcctat ataaaactaa   4329
atttgctatc tgtgtagaaa ataatttcat gacatttaca atcaggactg aagtaagttc   4389
ttcacacagt gacctctgaa tcagtttcag agaagggatg ggggagaaaa tgccttctag   4449
gttttgaact tctatgcatt agtgcagatg ttgtgaatgt gtaaaggtgt tcatagtttg   4509
actgtttcta tgtatgtttt ttcaaagaat tgttcctttt tttgaactat aatttttctt   4569
tttttggtta ttttaccatc acagtttaaa tgtatatctt ttatgtctct actcagacca   4629
tatttttaaa ggggtgcctc attatggggc agagaacttt tcaataagtc tcattaagat   4689
ctgaatcttg gttctaagca ttctgtataa tatgtgattg cttgtcctag ctgcagaagg   4749
ccttttgttt ggtcaaatgc atattttagc agagtttcaa ggaaatgatt gtcacacatg   4809
tcactgtagc ctcttggtgt agcaagctca catacaaaat acttttgtat atgcataata   4869
taaatcatct catgtggata tgaaacttct tttttaaaac ttaaaaaggt agaatgttat   4929
tgattacctt gattagggca gttttatttc cagatcctaa taattcctaa aaaatatgga   4989
aaagtttttt ttcaatcatt gtaccttgat attaaaacaa atatccttta agtatttcta   5049
atcagttagc ttctacagtt cttttgtctc cttttatatg cagctcttac gtgggagact   5109
tttccactta aaggagacat agaatgtgtg cttattctca gaaggttcat taactgaggt   5169
gatgagttaa caactagttg agcagtcagc ttcctaagtg ttttaggaca tttgttcatt   5229
atattttccg tcatataact agaggaagtg gaatgcagat aagtgccgaa ttcaaaccct   5289
tcattttatg tttaagctcc tgaatctgca ttccacttgg gttgttttta agcattctaa   5349
attttagttg attataagtt agatttcaca gaatcagtat tgcccttgat cttgtccttt   5409
ttatggagtt aacggggagg aagacccctc aggaaaacga aagtaaattg ttaaggctca   5469
```

-continued

```
tcttcatacc tttttccatt ttgaatccta caaaaatact gcaaaagact agtgaatgtt   5529

taaaattaca ctagattaaa taatatgaaa gtc                                5562


<210> SEQ ID NO 2
<211> LENGTH: 709
<212> TYPE: PRT
<213> ORGANISM: Homo sapiens

<400> SEQUENCE: 2

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
```

```
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705
```

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)
<223> OTHER INFORMATION:

<400> SEQUENCE: 3

-continued

```
cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac       375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac       423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat       471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa       519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca       567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa       615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa       663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga       711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat       759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag       807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa       855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag       903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat       951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac       999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa      1047
Gln Val Pro Glu Ala Glu Pro Glu Pro Ala Glu Glu Tyr Thr Glu Gln
                275                 280                 285
```

-continued

```
agt gaa gtt gaa tca aca gag tat gta aat aga cag ttc atg gca gaa      1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt      1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca      1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca      1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg      1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat      1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca      1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa      1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca      1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa      1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460

cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605
```

```
agt cgt ggt gtg tct cgt gga ggc tcc cgt ggt gct aga ggc ttg atg     2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt     2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct     2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat     2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc     2247
Gln Gln Asn Phe Lys Arg Gly Ser Gly Gln Ser Gly Pro Arg Gly Ala
                675                 680                 685

cca cga ggt aat att ttg tgg tgg tga tcctagctcc taagtggagc           2294
Pro Arg Gly Asn Ile Leu Trp Trp
            690

ttctgttctg gccttggaag agctgttaat agtctgcatg ttaggaatac atttatcctt   2354

tccagacttg ttgctaggga ttaaatgaaa tgctctgttt ctaaaactta atcttggacc   2414

caaattttaa tttttgaatg atttaatttt ccctgttact atataaactg tcttgaaaac   2474

tagaacatat tctcttctca gaaaaagtgt tttttccaact gaaaattatt tttcaggtcc   2534

taaaacctgc taaatgtttt taggaagtac ttactgaaac atttttgtaa gacatttttg   2594

gaatgagatt gaacatttat ataaatttat tattcctctt tcattttttt gaaacatgcc   2654

tattatattt tagggccaga caccctttaa tggccggata agccatagtt aacatttaga   2714

gaaccattta gaagtgatag aactaatgga atttgcaatg ccttttggac ctctattagt   2774

gatataaata tcaagttatt tctgactttt aaacaaaact cccaaattcc taacttattg   2834

agctatactt aaaaaaaatt acaggtttag agagtttttt gtttttcttt tactgttgga   2894

aaactacttc ccattttggc aggaagttaa cctatttaac aattagagct agcatttcat   2954

gtagtctgaa attctaaatg gttctctgat ttgagggagg ttaaacatca aacaggtttc   3014

ctctattggc cataacatgt ataaaatgtg tgttaaggag gaattacaac gtactttgat   3074

ttgaatacta gtagaaactg gccaggaaaa aggtacattt ttctaaaaat taatggatca   3134

cttgggaatt actgacttga ctagaagtat caaaggatgt ttgcatgtga atgtgggtta   3194

tgttctttcc caccttgtag catattcgat gaaagttgag ttaactgata gctaaaaatc   3254

tgttttaaca gcatgtaaaa agttatttta tctgttaaaa gtcattatac agttttgaat   3314

gttatgtagt ttctttttaa cagtttaggt aataaggtct gttttcattc tggtgctttt   3374

attaattttg atagtatgat gttacttact actgaaatgt aagctagagt gtacactaga   3434

atgtaagctc catgagagca ggtaccttgt ctgtcttctc tgctgtatct attcccaacg   3494

cttgatgatg gtgcctggca catagtaggc actcaataaa tatttgttga atgaatgaa    3553
```

<210> SEQ ID NO 4
<211> LENGTH: 694
<212> TYPE: PRT
<213> ORGANISM: Homo sapiens

<400> SEQUENCE: 4

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
```

-continued

```
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445
```

```
Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690


<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)
<223> OTHER INFORMATION:

<400> SEQUENCE: 5

gtcacaaata acttggagtt tgcaaaagaa ttacagagga gtttc atg gca tta agt      57
                                                  Met Ala Leu Ser
                                                  1

caa gat att cag aaa aca ata aag aag act gca cgt cgg gag cag ctt       105
Gln Asp Ile Gln Lys Thr Ile Lys Lys Thr Ala Arg Arg Glu Gln Leu
5                   10                  15                  20

atg aga gag gaa gcg gaa caa aaa cgt tta aaa act gta ctt gag ctc       153
Met Arg Glu Glu Ala Glu Gln Lys Arg Leu Lys Thr Val Leu Glu Leu
                25                  30                  35

cag tat gtt ttg gac aaa ttg gga gat gat gaa gtg aga act gac ctg       201
Gln Tyr Val Leu Asp Lys Leu Gly Asp Asp Glu Val Arg Thr Asp Leu
            40                  45                  50

aag caa ggt ttg aat gga gtg cca ata ttg tct gaa gaa gaa ttg tcg       249
Lys Gln Gly Leu Asn Gly Val Pro Ile Leu Ser Glu Glu Glu Leu Ser
```

-continued

```
        55                  60                  65

ttg ttg gat gaa ttc tac aaa tta gca gac cct gaa cgg gac atg agc      297
Leu Leu Asp Glu Phe Tyr Lys Leu Ala Asp Pro Glu Arg Asp Met Ser
    70                  75                  80

ttg agg ttg aat gag cag tat gaa cat gct tcc att cac ctg tgg gac      345
Leu Arg Leu Asn Glu Gln Tyr Glu His Ala Ser Ile His Leu Trp Asp
85                  90                  95                  100

ttg ctg gaa gga aag gaa aag tct gta tgt gga aca acc tat aaa gca      393
Leu Leu Glu Gly Lys Glu Lys Ser Val Cys Gly Thr Thr Tyr Lys Ala
                105                 110                 115

cta aag gaa att gtt gag cgt gtt ttc cag tca aat tac ttt gac agc      441
Leu Lys Glu Ile Val Glu Arg Val Phe Gln Ser Asn Tyr Phe Asp Ser
            120                 125                 130

act cac aac cac cag aat ggg cta tgt gag gaa gaa gag gca gcc tca      489
Thr His Asn His Gln Asn Gly Leu Cys Glu Glu Glu Glu Ala Ala Ser
        135                 140                 145

gca cct aca gtt gaa gac cag gta gct gaa gct gag cct gag cca gca      537
Ala Pro Thr Val Glu Asp Gln Val Ala Glu Ala Glu Pro Glu Pro Ala
    150                 155                 160

gaa gaa tac act gaa caa agt gaa gtt gaa tca aca gag tat gta aat      585
Glu Glu Tyr Thr Glu Gln Ser Glu Val Glu Ser Thr Glu Tyr Val Asn
165                 170                 175                 180

aga caa ttt atg gca gaa aca cag ttc agc agt ggt gaa aag gag cag      633
Arg Gln Phe Met Ala Glu Thr Gln Phe Ser Ser Gly Glu Lys Glu Gln
                185                 190                 195

gta gat gag tgg acg gtc gaa aca gtg gag gtg gtg aat tca ctc cag      681
Val Asp Glu Trp Thr Val Glu Thr Val Glu Val Val Asn Ser Leu Gln
            200                 205                 210

cag caa cct cag gct gcg tct cct tca gta cca gag ccc cac tct ttg      729
Gln Gln Pro Gln Ala Ala Ser Pro Ser Val Pro Glu Pro His Ser Leu
        215                 220                 225

act ccg gtg gct cag gca gat ccc ctt gtg aga aga cag cga gtc cag      777
Thr Pro Val Ala Gln Ala Asp Pro Leu Val Arg Arg Gln Arg Val Gln
    230                 235                 240

gac ctt atg gcg cag atg cag ggg ccc tat aat ttc ata cag gat tca      825
Asp Leu Met Ala Gln Met Gln Gly Pro Tyr Asn Phe Ile Gln Asp Ser
245                 250                 255                 260

atg ctg gat ttt gaa aac cag aca ctc gat cct gcc att gta tct gca      873
Met Leu Asp Phe Glu Asn Gln Thr Leu Asp Pro Ala Ile Val Ser Ala
                265                 270                 275

cag cct atg aat ccg aca caa aac atg gac atg ccc cag ctg gtt tgc      921
Gln Pro Met Asn Pro Thr Gln Asn Met Asp Met Pro Gln Leu Val Cys
            280                 285                 290

cct cca gtt cat tct gaa tct aga ctt gct caa cct aat caa gtt cct      969
Pro Pro Val His Ser Glu Ser Arg Leu Ala Gln Pro Asn Gln Val Pro
        295                 300                 305

gta caa cca gaa gct aca cag gtt cct ttg gtt tca tcc aca agt gag     1017
Val Gln Pro Glu Ala Thr Gln Val Pro Leu Val Ser Ser Thr Ser Glu
    310                 315                 320

ggg tat aca gca tct caa ccc ttg tac cag cct tct cat gct aca gag     1065
Gly Tyr Thr Ala Ser Gln Pro Leu Tyr Gln Pro Ser His Ala Thr Glu
325                 330                 335                 340

caa cga cca caa aag gaa cca att gac cag att cag gca aca atc tct     1113
Gln Arg Pro Gln Lys Glu Pro Ile Asp Gln Ile Gln Ala Thr Ile Ser
                345                 350                 355

tta aat aca gac cag act aca gcg tca tca tcc ctt ccg gct gct tct     1161
Leu Asn Thr Asp Gln Thr Thr Ala Ser Ser Ser Leu Pro Ala Ala Ser
            360                 365                 370

cag cct cag gta ttc cag gct ggg aca agc aaa cca tta cat agc agt     1209
```

```
Gln Pro Gln Val Phe Gln Ala Gly Thr Ser Lys Pro Leu His Ser Ser
        375                 380                 385

gga atc aat gta aat gca gct cca ttc caa tcc atg caa acg gtg ttc      1257
Gly Ile Asn Val Asn Ala Ala Pro Phe Gln Ser Met Gln Thr Val Phe
    390                 395                 400

aat atg aat gcc cca gtt cct cct gtt aat gaa cca gaa act ttg aaa      1305
Asn Met Asn Ala Pro Val Pro Pro Val Asn Glu Pro Glu Thr Leu Lys
405                 410                 415                 420

caa caa aat cag tac cag gcc agt tat aac cag agc ttt tct agt cag      1353
Gln Gln Asn Gln Tyr Gln Ala Ser Tyr Asn Gln Ser Phe Ser Ser Gln
                425                 430                 435

cct cac caa gta gaa caa aca gag gga tgc cgc aaa tga acactcagca      1402
Pro His Gln Val Glu Gln Thr Glu Gly Cys Arg Lys
            440                 445

agtgaattaa tctgattcac aggattatgt ttaaacgcca aaaacacact ggccagtgta   1462

ccataatatg ttaccagaag agttattatc tatttgttct ccctttcagg aaacttattg   1522

taaagggact gttttcatcc cataaagaca ggactacaat tgtcagcttt atattacctg   1582

gaaaaaaaaa aaaaaaaaaa aaa                                            1605


<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240
```

```
Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
        275                 280                 285

Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
        355                 360                 365

Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
        435                 440                 445


<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 7

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110
```

-continued

```
aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
```

-continued

```
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttgttct ccctttcagg aaacttattg taaagggact   2274

gttttcatcc cataaagaca ggactacaat tgtcagcttt atattacctg gatatggaag   2334
```

-continued

```
gaaactattt ttattctgca tgttcttcct aagcgtcatc ttgagccttg cacatgatac   2394

tcagattcct caccccttgct taggagtaaa acataataca ctttacaggg tgatatctcc   2454

atagttattt gaagtggctt ggaaaaagca agattaactt ctgacattgg ataaaaatca   2514

acaaatcagc cctagagtta ttcaaatggt aattgacaaa aactaaaata tttcccttcg   2574

agaaggagtg gaatgtggtt tggcagaaca actgcatttc acagcttttc cggttaaatt   2634

ggagcactaa acgtttagat gcataccaaa ttatgcatgg gcccttaata taaaaggctg   2694

gctaccagct ttgacacagc actattcatc ctctggccaa acaactgtgg ttaaacaaca   2754

catgtaaatt gctttttaac agctgatact ataataagac aaagccaaaa tgcaaaaatt   2814

gggctttgat tggcactttt tgaaaaatat gcaacaaata tgggatgtaa tctggatggc   2874

cgcttctgta cttaatgtga agtatttaga taccttttttg aacacttaac agtttcttct   2934

gacaatgact tttgtaagga ttggtactat ctatcattcc ttataatgta cattgtctgt   2994

cactaatcct cagatcttgc tgtattgtca cctaaattgg tacaggtact gatgaaaata   3054

tctaatggat aatcataaca ctcttggtca catgtttttc ctgcagcctg aaggttttta   3114

aaagaaaaag atatcaaatg cctgctgcta ccaccctttt aaattgctat cttttgaaaa   3174

gcaccagtat gtgttttaga ttgatttccc tattttaggg aaatgacaga cagtagtttc   3234

agttctgatg gtataagcaa aacaaataaa acatgtttat aaaagttgta tcttgaaaca   3294

ctggtgttca acagctagca gcttatgtgg ttcaccccat gcattgttag tgtttcagat   3354

tttatggtta tctccagcag ctgtttctgt agtacttgca tttatctttt gtctaaccct   3414

aatattctca cggaggcatt tatattcaaa gtggtgatcc cttcacttag acgcataggg   3474

agagtcacaa gtttgatgaa gaggacagtg tagtaattta tatgctgttg gaatttgtgc   3534

tagcagtttg agcactagtt ctgtgtgcct atgaacttaa tgctgcttgt catattccac   3594

tttgacttca tggagaatta atcccatcta ctcagcaaag gctatactaa tactaagtta   3654

atggtatttt ctgtgcagaa attgaatttt gttttattag catttagcta aggaattttt   3714

ccagtaggtg ctcagctact aaagaaaaac aaaaacaaga cacaaaacta ttctcaaaca   3774

ttcattgtta gacaactgga gtttttgctg gttttgtaac ctactaaaat ggataggctg   3834

ttgaacattc cacattcaaa agttttttgt agggtggtgg ggaagggggg gtgtcttcaa   3894

tgtttatttt aaaataaaat aagttcttga cttttctcat gtgtggttgt ggtacatcat   3954

attggaaggg ttatctgttt acttttgcaa atgagtattt ctcttgctag cacctcccgt   4014

tgtgcgcttt aaatgacatc tgcctgggat gtaccacaac catatgttag ctgtatttta   4074

tggggaatag ataaaatatt cgtggtttat tgggtaatcc ctagatgtgt atgcttacaa   4134

tcctatatat aaaactaaat                                               4154
```

```
<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45
```

```
His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460
```

Gln Arg Pro Gln Lys Glu Pro Ile Asp Gln Ile Gln Ala Thr Ile Ser
465 470 475 480

Leu Asn Thr Asp Gln Thr Thr Ala Ser Ser Ser Leu Pro Ala Ala Ser
485 490 495

Gln Pro Gln Val Phe Gln Ala Gly Thr Ser Lys Pro Leu His Ser Ser
500 505 510

Gly Ile Asn Val Asn Ala Ala Pro Phe Gln Ser Met Gln Thr Val Phe
515 520 525

Asn Met Asn Ala Pro Val Pro Pro Val Asn Glu Pro Glu Thr Leu Lys
530 535 540

Gln Gln Asn Gln Tyr Gln Ala Ser Tyr Asn Gln Ser Phe Ser Ser Gln
545 550 555 560

Pro His Gln Val Glu Gln Thr Asp Leu Gln Gln Glu Gln Leu Gln Thr
565 570 575

Val Val Gly Thr Tyr His Gly Ser Gln Asp Gln Pro His Gln Val Thr
580 585 590

Gly Asn His Gln Gln Pro Pro Gln Gln Asn Thr Gly Phe Pro Arg Ser
595 600 605

Ser Gln Pro Tyr Tyr Asn Ser Arg Gly Val Ser Arg Gly Gly Ser Arg
610 615 620

Gly Ala Arg Gly Leu Met Asn Gly Tyr Arg Gly Pro Ala Asn Gly Phe
625 630 635 640

Arg Gly Gly Tyr Asp Gly Tyr Arg Pro Ser Phe Ser Asn Thr Pro Asn
645 650 655

Ser Gly Tyr Thr Gln Ser Gln Phe Ser Ala Pro Arg Asp Tyr Ser Gly
660 665 670

Tyr Gln Arg Asp Gly Tyr Gln Gln Asn Phe Lys Arg Gly Ser Gly Gln
675 680 685

Ser Gly Pro Arg Gly Ala Pro Arg Gly Arg Gly Gly Pro Pro Arg Pro
690 695 700

Asn Arg Gly Met Pro Gln Met Asn Thr Gln Gln Val Asn
705 710 715

<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)
<223> OTHER INFORMATION:

<400> SEQUENCE: 9 atg ccg tcg gcc acc agc ctc agc gga agc ggc agc aag tcg tcg ggc 48
Met Pro Ser Ala Thr Ser Leu Ser Gly Ser Gly Ser Lys Ser Ser Gly
1 5 10 15 ccg ccg ccc ccg tcg ggt tcc tcc ggg agc gag gcg gcg gcg gcg gcg 96
Pro Pro Pro Pro Ser Gly Ser Ser Gly Ser Glu Ala Ala Ala Ala Ala
20 25 30 ggg gcg gcg ggg gcg gcg ggg gcc ggg gcg gct gcg ccc gcc tcc cag 144
Gly Ala Ala Gly Ala Ala Gly Ala Gly Ala Ala Ala Pro Ala Ser Gln
35 40 45 cac ccc gcg acc ggc acc ggc gct gtc cag acc gag gcc atg aag cag 192
His Pro Ala Thr Gly Thr Gly Ala Val Gln Thr Glu Ala Met Lys Gln
50 55 60 atc ctc ggg gtg atc gac aag aaa ctc cgg aac ctg gag aag aaa aag 240
Ile Leu Gly Val Ile Asp Lys Lys Leu Arg Asn Leu Glu Lys Lys Lys
65 70 75 80

-continued

```
ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
```

```
385                 390                 395                 400

cag cct atg aat ccg aca caa aac atg gac atg ccc cag ctg gtt tgc      1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag      1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
        675                 680                 685

agt gga cca cgg gga gcc cca cga ggt aat att ttg tgg tgg tga          2109
Ser Gly Pro Arg Gly Ala Pro Arg Gly Asn Ile Leu Trp Trp
    690                 695                 700

tcctagctcc taagtggagc ttctgttctg gccttggaag agctgttcca tagtctgcat    2169
```

```
gtaggttaca tgttaggaat acatttatca ttaccagact tgttgctagg gattaaatga   2229
aatgctctgt ttctaaaact tctcttgaac ccaaatttaa ttttttgaat gactttccct   2289
gttactatat aaattgtctt gaaaactaga acatttctcc tcctcagaaa aagtgttttt   2349
ccaactgcaa attatttttc aggtcctaaa acctgctaaa tgtttttagg aagtacttac   2409
tgaaacattt ttgtaagaca tttttggaat gagattgaac atttatataa atttattatt   2469
attcctcttt catttttgaa catgcatatt atattttagg gtcagaaatc ctttaatggc   2529
caaataagcc atagttacat ttagagaacc atttagaagt gatagaacta actgaaattt   2589
caatgccttt ggatcattaa tagcgatata aatttcaaat tgtttctgac ttttaaataa   2649
aacatccaaa atcctaacta acttcctgaa ctatatttaa aaattacagg tttaaggagt   2709
ttctggtttt ttttctctta ccataggaaa actgtttcct gtttggccag gaagtcaacc   2769
tgtgtaataa ttagaagtag catttcatat gatctgaagt tctaaatggt tctctgattt   2829
aagggaagtt aaattgaata ggtttcctct agttattggc cataacatgt ataaaatgta   2889
tattaaggag gaatacaaag tactttgatt tcaatgctag tagaaactgg ccagcaaaaa   2949
ggtgcatttt atttttaaat taatggatca cttgggaatt actgacttga agtatcaaag   3009
gatatttgca tgtgaatgtg ggttatgttc tttctcacct tgtagcatat tctatgaaag   3069
ttgagttgac tggtagctaa aaatctgttt taacagcatg taaaaagtta ttttatctgt   3129
tacaagtcat tatacaattt tgaatgttat gtagtttctt tttaacagtt taggtaacaa   3189
ggtctgtttt tcattctggt gcttttatta attttgatag tatgatgtta cttactactg   3249
aaatgtaagc tagagtgtac actagaatgt aagctccatg agagcaggta ccttgtctgt   3309
cttcactgct gtatctattt ccaacgcctg atgacagtgc ctgacacata gtaggcactc   3369
aataaatact tgttgaatga atgaatgaat gagtactggt ggaatactcc attagctcta   3429
ctcttctttt agctagagaa catgagcaaa tttgcgcatg acaacttcca ggacaggtga   3489
acactgaaga attgacctct taaacctaat aatgtggtga caagctgccc acatgcttct   3549
tgacttcaga tgaaaatctg cttgaaggca aagcaaataa tatttgaaag aaaaaccaaa   3609
tgccattttt gtcttctagg tcgtggaggg cccccaagac ccaacagagg gatgccgcaa   3669
atgaacactc agcaagtgaa ttaatctgat tcacaggatt atgtttaaac gccaaaaaca   3729
cactggccag tgtaccataa tatgttacca gaagagttat tatctatttg ttctcccttt   3789
caggaaactt attgtaaagg gactgttttc atcccataaa gacaggacta caattgtcag   3849
ctttatatta cctggatatg gaaggaaact atttttattc tgcatgttct tcctaagcgt   3909
catcttgagc cttgcacatg atactcagat tcctcaccct tgcttaggag taaaacataa   3969
tacactttac agggtgatat ctccatagtt atttgaagtg gcttggaaaa agcaagatta   4029
acttctgaca ttggataaaa atcaacaaat cagccctaga gttattcaaa tggtaattga   4089
caaaaactaa aatatttccc ttcgagaagg agtggaatgt ggtttggcag aacaactgca   4149
tttcacagct tttccggtta aattggagca ctaaacgttt agatgcatac caaattatgc   4209
atgggccctt aatataaaag gctggctacc agctttgaca cagcactatt catcctctgg   4269
ccaaacaact gtggttaaac aacacatgta aattgctttt taacagctga tactataata   4329
agacaaagcc aaaatgcaaa aattgggctt tgattggcac tttttgaaaa atatgcaaca   4389
aatatgggat gtaatctgga tggccgcttc tgtacttaat gtgaagtatt tagatacctt   4449
tttgaacact taacagtttc ttctgacaat gacttttgta aggattggta ctatctatca   4509
```

ttccttataa tgtacattgt ctgtcactaa tcctcagatc ttgctgtatt gtcacctaaa 4569 ttggtacagg tactgatgaa aatatctaat ggataatcat aacactcttg gtcacatgtt 4629 tttcctgcag cctgaaggtt tttaaaagaa aaagatatca aatgcctgct gctaccaccc 4689 ttttaaattg ctatcttttg aaaagcacca gtatgtgttt tagattgatt tccctatttt 4749 agggaaatga cagacagtag tttcagttct gatggtataa gcaaaacaaa taaaacatgt 4809 ttataaaagt tgtatcttga aacactggtg ttcaacagct agcagcttat gtggttcacc 4869 ccatgcattg ttagtgtttc agattttatg gttatctcca gcagctgttt ctgtagtact 4929 tgcatttatc 4939

<210> SEQ ID NO 10
<211> LENGTH: 702
<212> TYPE: PRT
<213> ORGANISM: Canis familiaris

<400> SEQUENCE: 10

Met Pro Ser Ala Thr Ser Leu Ser Gly Ser Gly Ser Lys Ser Ser Gly
1 5 10 15

Pro Pro Pro Pro Ser Gly Ser Ser Gly Ser Glu Ala Ala Ala Ala Ala
20 25 30

Gly Ala Ala Gly Ala Ala Gly Ala Gly Ala Ala Ala Pro Ala Ser Gln
35 40 45

His Pro Ala Thr Gly Thr Gly Ala Val Gln Thr Glu Ala Met Lys Gln
50 55 60

Ile Leu Gly Val Ile Asp Lys Lys Leu Arg Asn Leu Glu Lys Lys Lys
65 70 75 80

Gly Lys Leu Asp Asp Tyr Gln Glu Arg Met Asn Lys Gly Glu Arg Leu
85 90 95

Asn Gln Asp Gln Leu Asp Ala Val Ser Lys Tyr Gln Glu Val Thr Asn
100 105 110

Asn Leu Glu Phe Ala Lys Glu Leu Gln Arg Ser Phe Met Ala Leu Ser
115 120 125

Gln Asp Ile Gln Lys Thr Ile Lys Lys Thr Ala Arg Arg Glu Gln Leu
130 135 140

Met Arg Glu Glu Ala Glu Gln Lys Arg Leu Lys Thr Val Leu Glu Leu
145 150 155 160

Gln Tyr Val Leu Asp Lys Leu Gly Asp Asp Glu Val Arg Thr Asp Leu
165 170 175

Lys Gln Gly Leu Asn Gly Val Pro Ile Leu Ser Glu Glu Glu Leu Ser
180 185 190

Leu Leu Asp Glu Phe Tyr Lys Leu Ala Asp Pro Glu Arg Asp Met Ser
195 200 205

Leu Arg Leu Asn Glu Gln Tyr Glu His Ala Ser Ile His Leu Trp Asp
210 215 220

Leu Leu Glu Gly Lys Glu Lys Ser Val Cys Gly Thr Thr Tyr Lys Ala
225 230 235 240

Leu Lys Glu Ile Val Glu Arg Val Phe Gln Ser Asn Tyr Phe Asp Ser
245 250 255

Thr His Asn His Gln Asn Gly Leu Cys Glu Glu Glu Glu Ala Ala Ser
260 265 270

Ala Pro Thr Val Glu Asp Gln Val Ala Glu Ala Glu Pro Glu Pro Ala
275 280 285

Glu Glu Tyr Thr Glu Gln Ser Glu Val Glu Ser Thr Glu Tyr Val Asn

-continued

```
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Asn Ile Leu Trp Trp
    690                 695                 700
```

<210> SEQ ID NO 11

```
<211> LENGTH: 3306
<212> TYPE: DNA
<213> ORGANISM: Canis familiaris
<220> FEATURE:
<221> NAME/KEY: CDS
<222> LOCATION: (1)..(2040)
<223> OTHER INFORMATION:

<400> SEQUENCE: 11

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
```

-continued

```
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590
```

-continued

```
ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gga tgc cgc aaa tga acactcagca agtgaattaa tctgattcac    2070
Tyr Gln Arg Gly Cys Arg Lys
        675

aggattatgt ttaaacgcca aaaacacact ggccagtgta ccataatatg ttaccagaag   2130

agttattatc tatttgttct ccctttcagg aaacttattg taaagggact gttttcatcc   2190

cataaagaca ggactacaat tgtcagcttt atattacctg gatatggaag gaaactattt   2250

ttattctgca tgttcttcct aagcgtcatc ttgagccttg cacatgatac tcagattcct   2310

caccccttgct taggagtaaa acataataca ctttacaggg tgatatctcc atagttattt  2370

gaagtggctt ggaaaaagca agattaactt ctgacattgg ataaaaatca acaaatcagc   2430

cctagagtta ttcaaatggt aattgacaaa aactaaaata tttcccttcg agaaggagtg   2490

gaatgtggtt tggcagaaca actgcatttc acagcttttc cggttaaatt ggagcactaa   2550

acgtttagat gcataccaaa ttatgcatgg gcccttaata taaaaggctg gctaccagct   2610

ttgacacagc actattcatc ctctggccaa acaactgtgg ttaaacaaca catgtaaatt   2670

gctttttaac agctgatact ataataagac aaagccaaaa tgcaaaaatt gggctttgat   2730

tggcactttt tgaaaaatat gcaacaaata tgggatgtaa tctggatggc cgcttctgta   2790

cttaatgtga agtatttaga taccttttttg aacacttaac agtttcttct gacaatgact  2850

tttgtaagga ttggtactat ctatcattcc ttataatgta cattgtctgt cactaatcct   2910

cagatcttgc tgtattgtca cctaaattgg tacaggtact gatgaaaata tctaatggat   2970

aatcataaca ctcttggtca catgtttttc ctgcagcctg aaggttttta aaagaaaaag   3030

atatcaaatg cctgctgcta ccaccctttt aaattgctat cttttgaaaa gcaccagtat   3090

gtgttttaga ttgatttccc tattttaggg aaatgacaga cagtagtttc agttctgatg   3150

gtataagcaa aacaaataaa acatgtttat aaaagttgta tcttgaaaca ctggtgttca   3210

acagctagca gcttatgtgg ttcaccccat gcattgttag tgtttcagat tttatggtta   3270

tctccagcag ctgtttctgt agtacttgca tttatc                             3306


<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30
```

-continued

```
Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445
```

```
Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
        675


<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 13

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
```

```
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
```

-continued

```
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag      1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc      2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa              2154
Asn Arg Gly Met Pro Gln Met Asn Thr Gln Gln Val Asn
705                 710                 715
```

```
tctgattcac aggattatgt ttaaacgcca aaaacacact ggccagtgta ccataatatg   2214

ttaccagaag agttattatc tatttggact gttttcatcc cataaagaca ggactacaat   2274

tgtcagc                                                             2281


<210> SEQ ID NO 14
<211> LENGTH: 717
<212> TYPE: PRT
<213> ORGANISM: Canis familiaris

<400> SEQUENCE: 14

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350
```

```
Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715
```

<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)
<223> OTHER INFORMATION:

```
<400> SEQUENCE: 15

cgcgtctcgc cccgtccacc gattgactcg ccgctcttgt ccttcctccc gctctttctt      60

ctctcccctt acggtttcaa g atg cct tcg gcc acc agc cac agc gga agc       111
                        Met Pro Ser Ala Thr Ser His Ser Gly Ser
                        1               5                   10

ggc agc aag tcg tcc gga ccg cca ccg ccg tcg ggt tcc tcc ggg aat       159
Gly Ser Lys Ser Ser Gly Pro Pro Pro Pro Ser Gly Ser Ser Gly Asn
                15                  20                  25

gag gcg ggg gcc ggg gcc gcc gcg ccg gct tcc caa cac ccc atg acc       207
Glu Ala Gly Ala Gly Ala Ala Ala Pro Ala Ser Gln His Pro Met Thr
            30                  35                  40

ggc acc ggg gct gtc cag acc gag gcc atg aag cag att ctc ggg gtg       255
Gly Thr Gly Ala Val Gln Thr Glu Ala Met Lys Gln Ile Leu Gly Val
        45                  50                  55

atc gac aag aaa ctt cgg aac ctg gag aag aaa aag ggc aag ctt gat       303
Ile Asp Lys Lys Leu Arg Asn Leu Glu Lys Lys Lys Gly Lys Leu Asp
    60                  65                  70

gat tat cag gaa cga atg aac aaa ggg gaa agg ctt aat caa gat cag       351
Asp Tyr Gln Glu Arg Met Asn Lys Gly Glu Arg Leu Asn Gln Asp Gln
75                  80                  85                  90

ctg gat gcc gtg tct aag tac cag gaa gtc aca aat aac ttg gag ttt       399
Leu Asp Ala Val Ser Lys Tyr Gln Glu Val Thr Asn Asn Leu Glu Phe
                95                  100                 105

gca aaa gaa tta cag agg agt ttc atg gca tta agc caa gat att cag       447
Ala Lys Glu Leu Gln Arg Ser Phe Met Ala Leu Ser Gln Asp Ile Gln
            110                 115                 120

aaa aca ata aag aag aca gca cgt cgg gag cag ctt atg aga gag gaa       495
Lys Thr Ile Lys Lys Thr Ala Arg Arg Glu Gln Leu Met Arg Glu Glu
        125                 130                 135

gct gaa cag aaa cgt tta aaa aca gta ctt gag ctg cag tat gtt ttg       543
Ala Glu Gln Lys Arg Leu Lys Thr Val Leu Glu Leu Gln Tyr Val Leu
    140                 145                 150

gac aaa cta gga gat gat gaa gtg aga act gac ctg aag caa ggt ttg       591
Asp Lys Leu Gly Asp Asp Glu Val Arg Thr Asp Leu Lys Gln Gly Leu
155                 160                 165                 170

aat gga gtg cca ata ttg tct gaa gag gag ttg tcg ttg tta gat gag       639
Asn Gly Val Pro Ile Leu Ser Glu Glu Glu Leu Ser Leu Leu Asp Glu
                175                 180                 185

ttc tac aaa tta gca gac cct gaa cga gac atg agc ttg agg ttg aat       687
Phe Tyr Lys Leu Ala Asp Pro Glu Arg Asp Met Ser Leu Arg Leu Asn
            190                 195                 200

gag cag tat gaa cat gcc tcc att cac ctg tgg gac ttg ctg gaa gga       735
Glu Gln Tyr Glu His Ala Ser Ile His Leu Trp Asp Leu Leu Glu Gly
        205                 210                 215

aag gaa aaa cct gta tgt gga aca act tat aaa gct cta aag gaa att       783
Lys Glu Lys Pro Val Cys Gly Thr Thr Tyr Lys Ala Leu Lys Glu Ile
    220                 225                 230

gtt gag cgt gtt ttc cag tca aac tac ttt gac agc acc cac aac cac       831
Val Glu Arg Val Phe Gln Ser Asn Tyr Phe Asp Ser Thr His Asn His
235                 240                 245                 250

cag aat ggt ctg tgt gag gaa gag gag gca gcc tca gca cct aca gtt       879
Gln Asn Gly Leu Cys Glu Glu Glu Glu Ala Ala Ser Ala Pro Thr Val
                255                 260                 265

gaa gac cag gca gct gaa gct gaa cct gag cca gtg gaa gaa tat act       927
Glu Asp Gln Ala Ala Glu Ala Glu Pro Glu Pro Val Glu Glu Tyr Thr
            270                 275                 280

gaa caa aat gag gtt gaa tca aca gag tat gta aat aga caa ttt atg       975
Glu Gln Asn Glu Val Glu Ser Thr Glu Tyr Val Asn Arg Gln Phe Met
```

-continued

```
        285                 290                 295

gca gaa aca cag ttc agc agt ggt gaa aag gag cag gta gat gat tgg      1023
Ala Glu Thr Gln Phe Ser Ser Gly Glu Lys Glu Gln Val Asp Asp Trp
    300                 305                 310

aca gtt gaa aca gtt gag gtg gta aat tca ctc cag cag caa cct cag      1071
Thr Val Glu Thr Val Glu Val Val Asn Ser Leu Gln Gln Gln Pro Gln
315                 320                 325                 330

gct gca tct cct tca gta cca gaa ccc cac tct ttg acc cca gtg gct      1119
Ala Ala Ser Pro Ser Val Pro Glu Pro His Ser Leu Thr Pro Val Ala
            335                 340                 345

caa gcc gat ccc ctc gtg aga aga cag cga gta cag gac ctt atg gca      1167
Gln Ala Asp Pro Leu Val Arg Arg Gln Arg Val Gln Asp Leu Met Ala
            350                 355                 360

caa atg cag ggg ccc tat aat ttc ata cag gat tca atg ttg gat ttt      1215
Gln Met Gln Gly Pro Tyr Asn Phe Ile Gln Asp Ser Met Leu Asp Phe
        365                 370                 375

gaa aac cag aca ctt gat cct gcc att gta tct gca cag ccg atg aat      1263
Glu Asn Gln Thr Leu Asp Pro Ala Ile Val Ser Ala Gln Pro Met Asn
    380                 385                 390

cca gca cag aac atg gac ata ccc cag ctg gtt tgc cct cca gtt cat      1311
Pro Ala Gln Asn Met Asp Ile Pro Gln Leu Val Cys Pro Pro Val His
395                 400                 405                 410

tct gaa tct aga ctt gct caa cct aat caa gtt tct gta cag cca gaa      1359
Ser Glu Ser Arg Leu Ala Gln Pro Asn Gln Val Ser Val Gln Pro Glu
            415                 420                 425

gct aca cag gtt cct ttg gtt tca tcc aca agt gag gga tat aca gca      1407
Ala Thr Gln Val Pro Leu Val Ser Ser Thr Ser Glu Gly Tyr Thr Ala
            430                 435                 440

tct caa ccc ttg tac caa cct tct cat gct act gac caa cga cca caa      1455
Ser Gln Pro Leu Tyr Gln Pro Ser His Ala Thr Asp Gln Arg Pro Gln
        445                 450                 455

aag gaa ccg att gat cag att cag gcg acg atc tct tta aat aca gac      1503
Lys Glu Pro Ile Asp Gln Ile Gln Ala Thr Ile Ser Leu Asn Thr Asp
    460                 465                 470

cag act aca gca tca tca tcc ctt cct gct gct tct cag cct caa gtg      1551
Gln Thr Thr Ala Ser Ser Ser Leu Pro Ala Ala Ser Gln Pro Gln Val
475                 480                 485                 490

ttc cag gct ggg aca agc aaa cct tta cat agc agt gga atc aat gta      1599
Phe Gln Ala Gly Thr Ser Lys Pro Leu His Ser Ser Gly Ile Asn Val
            495                 500                 505

aat gca gct cca ttc caa tcc atg caa acg gta ttc aat atg aat gcc      1647
Asn Ala Ala Pro Phe Gln Ser Met Gln Thr Val Phe Asn Met Asn Ala
            510                 515                 520

cca gtt cct cct gtt aat gaa cca gaa act tta aaa cag caa aat cag      1695
Pro Val Pro Pro Val Asn Glu Pro Glu Thr Leu Lys Gln Gln Asn Gln
        525                 530                 535

tac cag gcc agt tac aac cag agc ttt tcc agt cag cct cac caa gta      1743
Tyr Gln Ala Ser Tyr Asn Gln Ser Phe Ser Ser Gln Pro His Gln Val
    540                 545                 550

gaa caa aca gag ctt cag caa gaa cag ctt caa aca gtg gtt ggc act      1791
Glu Gln Thr Glu Leu Gln Gln Glu Gln Leu Gln Thr Val Val Gly Thr
555                 560                 565                 570

tat cat ggt tct cag gac cag ccc cat caa gtg act ggt aac cac cag      1839
Tyr His Gly Ser Gln Asp Gln Pro His Gln Val Thr Gly Asn His Gln
            575                 580                 585

cag cct cct cag cag aac act gga ttt cca cgt agc aat cag ccc tat      1887
Gln Pro Pro Gln Gln Asn Thr Gly Phe Pro Arg Ser Asn Gln Pro Tyr
            590                 595                 600

tac aac agt cgt ggt gtg tct cgt gga ggt tcc cgt ggt gct aga ggc      1935
```

```
Tyr Asn Ser Arg Gly Val Ser Arg Gly Gly Ser Arg Gly Ala Arg Gly
        605                 610                 615

ttg atg aat gga tac aga gga cct gct aat gga ttc aga gga gga tat     1983
Leu Met Asn Gly Tyr Arg Gly Pro Ala Asn Gly Phe Arg Gly Gly Tyr
    620                 625                 630

gat ggt tac cgc cct tca ttc tct act aac act cca aac agt ggt tat     2031
Asp Gly Tyr Arg Pro Ser Phe Ser Thr Asn Thr Pro Asn Ser Gly Tyr
635                 640                 645                 650

aca caa tct caa ttc agt gct ccc cgg gac tac tct ggc tat cag cgg     2079
Thr Gln Ser Gln Phe Ser Ala Pro Arg Asp Tyr Ser Gly Tyr Gln Arg
                655                 660                 665

gat gga tat cag cag aat ttc aag cga ggc tct ggg cag agt gga cca     2127
Asp Gly Tyr Gln Gln Asn Phe Lys Arg Gly Ser Gly Gln Ser Gly Pro
            670                 675                 680

cgg gga gcc cca cga ggt cgt gga ggg ccc cca aga ccc aac aga ggg     2175
Arg Gly Ala Pro Arg Gly Arg Gly Gly Pro Pro Arg Pro Asn Arg Gly
        685                 690                 695

atg ccg caa atg aac act cag caa gtg aat taa tctgattcac aggattatgt   2228
Met Pro Gln Met Asn Thr Gln Gln Val Asn
    700                 705

ttaatcgcca aaaacacact ggccagtgta ccataatatg ttaccagaag agttattatc   2288

tatttgttct ccctttcagg aaacttattg taaagggact gttttcatcc cataaagaca   2348

ggactacaat tgtcagcttt atattacctg gatatggaag gaaactattt ttactctgca   2408

tgttctgtcc taagcgtcat cttgagcctt gcacatgata ctcagattcc tcacccttgc   2468

ttaggagtaa aacataatat actttaatgg ggtgatatct ccatagttat ttgaagtggc   2528

ttggataaag caagactgac ttctgacatt ggataaaatc tacaaatcag ccctagagtc   2588

attcagtggt aactgacaaa actaaaatat ttcccttgaa aggaagatgg aaggagtgga   2648

gtgtggtttg gcagaacaac tgcatttcac agcttttcca cttaaattgg agcactgaac   2708

atttagatgc ataccgaatt atgcatgggc cctaatcaca cagacaaggc tggtgccagc   2768

cttaggcttg acacggcagt gttcaccctc tggccagacg actgtggttc aagacacatg   2828

taaattgctt tttaacagct gatactgtat aagacaaagc caaaatgcaa aattaggctt   2888

tgattggcac ttttcgaaaa atatgcaaca attaagggat ataatctgga tggccgcttc   2948

tgtacttaat gtgaaatatt tagatacctt tcaaacactt aacagtttct ttgacaatga   3008

gttttgtaag gattggtagt aaatatcatt ccttatgacg tacattgtct gtcactaatc   3068

cttggatctt gctgtattgt cacctaaatt ggtacaggta ctgatgaaaa tctaatggat   3128

aatcataaca ctcttggtta catgtttttc ctgcagcctg aaagttttta taagaaaaag   3188

acatcaaatg cctgctgctg ccaccctttt aaattgctat cttttgaaaa gcaccagtat   3248

gtgttttaga ttgatttccc tattttaggg aaatgacagt cagtagtttc acttctgatg   3308

gtataagcaa acaaataaaa catgtttata aaaaaaaaaa aaaaaaaaaa aaaaaaaaaa   3368

aaaaaaaaaa aaaaaaaa                                                 3386


<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
```

-continued

```
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Glu Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445
```

```
Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
            660                 665                 670

Phe Lys Arg Gly Ser Gly Gln Ser Gly Pro Arg Gly Ala Pro Arg Gly
        675                 680                 685

Arg Gly Gly Pro Pro Arg Pro Asn Arg Gly Met Pro Gln Met Asn Thr
    690                 695                 700

Gln Gln Val Asn
705


<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)
<223> OTHER INFORMATION:

<400> SEQUENCE: 17

atg gag ggc aag ctc gat gat tac caa gag cga atg aac aaa gga gaa       48
Met Glu Gly Lys Leu Asp Asp Tyr Gln Glu Arg Met Asn Lys Gly Glu
1               5                   10                  15

agg ctt aat cag gat cag ctg gat gct gtg tct aag tac cag gaa gtc       96
Arg Leu Asn Gln Asp Gln Leu Asp Ala Val Ser Lys Tyr Gln Glu Val
            20                  25                  30

aca aat aac ttg gag ttt gcg aaa gaa ttg cag agg agt ttc atg gcg      144
Thr Asn Asn Leu Glu Phe Ala Lys Glu Leu Gln Arg Ser Phe Met Ala
        35                  40                  45

ttg agt cag gat att cag aaa aca ata aag aag acg gca cgt cgg gag      192
Leu Ser Gln Asp Ile Gln Lys Thr Ile Lys Lys Thr Ala Arg Arg Glu
    50                  55                  60
```

```
cag ctt atg aga gaa gaa gct gaa cag aaa cgt tta aaa act gta ctt      240
Gln Leu Met Arg Glu Glu Ala Glu Gln Lys Arg Leu Lys Thr Val Leu
65                  70                  75                  80

gag ctg cag tat gtt ttg gac aaa ttg gga gat gaa gaa gtg cga act      288
Glu Leu Gln Tyr Val Leu Asp Lys Leu Gly Asp Glu Glu Val Arg Thr
                85                  90                  95

gac ctg aaa caa ggt ttg aat gga gtg cca ata ctc tct gaa gaa gag      336
Asp Leu Lys Gln Gly Leu Asn Gly Val Pro Ile Leu Ser Glu Glu Glu
            100                 105                 110

ttg tcg ctg ttg gat gag ttc tac aag tta gca gac cct gta cgg gac      384
Leu Ser Leu Leu Asp Glu Phe Tyr Lys Leu Ala Asp Pro Val Arg Asp
        115                 120                 125

atg agc ttg agg ttg aat gag cag tat gag cat gcc tcc att cac ctg      432
Met Ser Leu Arg Leu Asn Glu Gln Tyr Glu His Ala Ser Ile His Leu
    130                 135                 140

tgg gac ttg ctg gaa ggg aag gaa aaa tct gtc tgt gga aca acc tat      480
Trp Asp Leu Leu Glu Gly Lys Glu Lys Ser Val Cys Gly Thr Thr Tyr
145                 150                 155                 160

aaa gct ctg agg gaa att gtt gag cgt gtt ttc cag tcc aac tac ttt      528
Lys Ala Leu Arg Glu Ile Val Glu Arg Val Phe Gln Ser Asn Tyr Phe
                165                 170                 175

gac agc acc cac aac cac cag aat ggg ctc tgt gag gag gaa gag gct      576
Asp Ser Thr His Asn His Gln Asn Gly Leu Cys Glu Glu Glu Glu Ala
            180                 185                 190

acc tca gct cca aca gct gaa gac cag gga gct gaa gct gaa cct gag      624
Thr Ser Ala Pro Thr Ala Glu Asp Gln Gly Ala Glu Ala Glu Pro Glu
        195                 200                 205

cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
    210                 215                 220

gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240

cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255

cag cag caa cct cag gct gca tct cct tca gta ccg gag ccc cac tct      816
Gln Gln Gln Pro Gln Ala Ala Ser Pro Ser Val Pro Glu Pro His Ser
            260                 265                 270

ttg act cca gtg gct cag gca gat ccc ctt gtg aga aga cag cga gta      864
Leu Thr Pro Val Ala Gln Ala Asp Pro Leu Val Arg Arg Gln Arg Val
        275                 280                 285

cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300

tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320

gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335

tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350

cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365

gag ggg tat aca gca tct cag ccc ttg tac cag cct tct cat gct aca     1152
Glu Gly Tyr Thr Ala Ser Gln Pro Leu Tyr Gln Pro Ser His Ala Thr
```

```
    370                 375                 380

gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400

tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415

tct cag cct cag gtg ttc cag gct ggg aca agc aaa cct tta cac agc     1296
Ser Gln Pro Gln Val Phe Gln Ala Gly Thr Ser Lys Pro Leu His Ser
            420                 425                 430

agt ggg atc aat gta aat gca gcg cca ttc cag tcc atg caa acg gtg     1344
Ser Gly Ile Asn Val Asn Ala Ala Pro Phe Gln Ser Met Gln Thr Val
        435                 440                 445

ttc aac atg aat gcc ccg gtt cct cct gtt aat gaa cca gaa act tta     1392
Phe Asn Met Asn Ala Pro Val Pro Pro Val Asn Glu Pro Glu Thr Leu
    450                 455                 460

aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480

ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495

acg gtg gtt ggt act tac cat gct tcc caa gac cag ccc cat caa gtg     1536
Thr Val Val Gly Thr Tyr His Ala Ser Gln Asp Gln Pro His Gln Val
            500                 505                 510

acc ggt aac cac cag cag cct ccc cag cag aac act ggg ttt cca cgt     1584
Thr Gly Asn His Gln Gln Pro Pro Gln Gln Asn Thr Gly Phe Pro Arg
        515                 520                 525

agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
    530                 535                 540

cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
545                 550                 555                 560

ttc aga gga gga tat gat ggt tac cgc cct tcg ttc tct aac act cca     1728
Phe Arg Gly Gly Tyr Asp Gly Tyr Arg Pro Ser Phe Ser Asn Thr Pro
                565                 570                 575

aac agc ggt tac aca cag tct cag ttc agt gct ccc cgg gac tac tct     1776
Asn Ser Gly Tyr Thr Gln Ser Gln Phe Ser Ala Pro Arg Asp Tyr Ser
            580                 585                 590

ggc tat cag cgg gat gga tat cag cag aat ttc aag cga ggc tct ggg     1824
Gly Tyr Gln Arg Asp Gly Tyr Gln Gln Asn Phe Lys Arg Gly Ser Gly
        595                 600                 605

cag agt gga ccc cgg gga gcc cca cga ggt cgt gga ggg ccc cca aga     1872
Gln Ser Gly Pro Arg Gly Ala Pro Arg Gly Arg Gly Gly Pro Pro Arg
    610                 615                 620

ccc aac aga ggg atg ccg caa atg aac act cag caa gtg aat taa         1917
Pro Asn Arg Gly Met Pro Gln Met Asn Thr Gln Gln Val Asn
625                 630                 635

tctgattcac aggattatct ttaatcgcca aaacacactg gccagtgtac cataatatgt   1977

taccagaaga gttattatct atttgttctc cctttcagga aacttattgt aaagggactg   2037

ttttcatccc ataaagacag gactacagtt gtcagcttta tattacctgg atatggaagg   2097

aaactatttt tactctgcat gttctgtcct aagcgtcatc ttgagccttg cacatgatac   2157

tcagattcct ttcccttgct taggagtaaa acataatata ctttatgggg tgataatatc   2217

tccatagtta tttgaagtgg cttggaaaaa gcaagattga cttttgacat tggataaaat   2277

ctacaaatca gccctagagt ttcatggtca ttcacaaaac taaaatattt cccttgaaag   2337
```

```
gaagatggaa ggactggagt gtggtttggc agaacaactg catttcacag cttttcctat   2397

taaattggag cactgaatgt taaatgcata ccaaattatg catgggccct taatcacaca   2457

tacatggcta ccagctttga cacagcacta ttcatcctct ggccaaacga ctgtggttaa   2517

aaacacgtgt aaattgcttt ttaacagctg atactgtaaa agacaaagct aaaatgcaaa   2577

attaggcttt cattggcact tttcgaaaaa tatgcaacaa atttgggatg taatctggat   2637

ggccacttct gtacttaatg tgaagtattt agataccttt ttgaacactt aacagtttct   2697

tcgacaatga cttttgtaag gattggtagt atatatcatt ccttatgaca tacattgtct   2757

gttgctaatc cttggatctt gctgtattgt cacctaaatt ggtacaggta ctgatgaaaa   2817

tctctcatgg ataaacctaa cactcttcgt cacatgtttt tcctgcagcc tgaaggtttt   2877

taaaaggaaa agatatcaaa tgcctgctgc taccaccctt ttaaattgct atcttttgaa   2937

aagcaccagt atgtgttttt agattgattt ccctatttta gggaaatgac agtcagtagt   2997

ttcagttctg atggtataag caaagcaaat aaaacgtgtt tataaaagtt gtatcttgaa   3057

acactggtgt tcaacagcta gcagcttctg tggttcaccc cctgccttgt tagtgttacc   3117

catttatggt tatctccagc agcaatttct cta                                3150


<210> SEQ ID NO 18
<211> LENGTH: 638
<212> TYPE: PRT
<213> ORGANISM: Equus caballus

<400> SEQUENCE: 18

Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala
        35                  40                  45

Leu Ser Gln Asp Ile Gln Lys Thr Ile Lys Lys Thr Ala Arg Arg Glu
    50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220
```

-continued

```
Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
        275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Pro Val Asn Glu Pro Glu Thr Leu
    450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Gly Pro Pro Arg
    610                 615                 620

Pro Asn Arg Gly Met Pro Gln Met Asn Thr Gln Gln Val Asn
625                 630                 635
```

```
<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)
<223> OTHER INFORMATION:

<400> SEQUENCE: 19

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc cccctcggc tgcccactcc agacgtccag cggctccgcg cgcgcacg       178

atg ccc tcg gcc acc agc cac agc gga agc ggc agc aaa tcg tcg gga      226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca      274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag      322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg      370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
```

```
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
            325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
            405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
            485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
```

-continued

```
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac      1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta      2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg      2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca      2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct      2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc      2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt cgt      2242
Lys Arg Gly Ser Gly Gln Ser Gly Pro Arg Gly Ala Pro Arg Gly Arg
        675                 680                 685

gga ggg ccc cca aga ccc aac aga ggg atg ccg caa atg aac act cag      2290
Gly Gly Pro Pro Arg Pro Asn Arg Gly Met Pro Gln Met Asn Thr Gln
    690                 695                 700

caa gtg aat taa tgtgatacac aggattatgt ttaatcgcca aaaacacact          2342
Gln Val Asn
705

ggccagtgta ccataatatg ttaccagaag agttattatc tatttgttct ccctttcagg    2402

aaacttattg taaagggact gttttcatcc cataaagaca ggactgcaat tgtcagcttt    2462

acattacctg gatatggaag gaaactattt ttattctgca tgttctgtcc taagcgtcat    2522

cttgagcctt gcacacaata caatactcag attcctcacc cttgcttagg agtaaaacat    2582

tatatactta tggggtgata atatctccat agttagttga agtggcttgg aaaaaaaatg    2642

caagattgaa tttttgacct tggataaaat ctacaatcag ccctagaact attcagtggt    2702

aattgacaaa gttaaagcat tttctttgaa aggaagatgg aaggagtgga gtgtggttta    2762

gcaaaactgc atttcatagc tttcccatta aattggagca ccgacagatt aaaagcatac    2822

caaattatgc atgggtcctt actcacacaa gtgaggctgg ctaccagcct tgacatagca    2882

ctcactagtc ttctggccaa acgactgtga ttaaaacaca tgtaaattgc tctttagtag    2942

tggatactgt gtaagacaaa gccaaattgc aaatcaggct ttgattggct cttctggaaa    3002

atatgcatca aatatggggg ataatctgga tgggctgctg ctgtgctcaa tgtgaactat    3062

ttagatacct ttggaacact taacagtttc tctgaacaat gacttacatg gggattggtc    3122

ctgtttgtca ttcctcacca taattgcatt gtcatcacta atccttggat cttgctgtat    3182

tgttactcaa attggtaata ggtactgatg gaaatcgcta atggatggat aatcataaca    3242

cttttggtca catgttttct cctgcagcct gaaagttctt aaagaaaaag atatcaaatg    3302

cctgctgcta ccaccctttt aaattgctat ctttagaaaa gcaccggtat gtgttttaga    3362

ttcatttccc tgttttaggg aaatgacagg cagtagtttc agttctgatg gcaaaacaaa    3422

taaaaacatg tttctaaaag ttgtatcttg aaacactggt gttcaacagc tagcagctaa    3482

agtaattcaa cccatgcatt gctagtgtca cagcctttgg ttatgtctag tagctgtttc    3542
```

```
tgaagtattt tcatttatct tttgtcaaat ttaaccctgt ttgaattctc tcctttcctc   3602
aaggagacac ttatgttcaa agtgttgatt ctttgcctta ggtgcataga gagtagacag   3662
tttggagatg gaaaggttag cagtgactta gccatatgtt ctgtgttgga atttgtgcta   3722
gcagtttgag cactagctct gcgtgcctat gaactgaatg ctgcttgtcc cattccattt   3782
tatgtcatgg agaaataatt ccacttggta acacaaaggc taagttaatg ttattttctg   3842
tacagaaatt aaattttact tttagccttt tgtaaacttt tttttttttt ttccaagccg   3902
gtatcagcta ctcaaaacaa ttctcagata ttcatcatta gacaactgga gtttttgctg   3962
gttttgtagc ctactaaaac tgctgaggct gttgaacatt ccacattcaa aagttttgta   4022
gggtggtgga taatggggaa gcttcaatgt ttattttaaa ataaataaaa taagttcttg   4082
acttttctca tgtgtggtta tggtacatca tattggaagg gttatctgtt tacttttgcc   4142
aagactattt tgccagcacc tacacttgtg tgctttaaaa gacaactacc tgggatgtac   4202
cacaaccata tgttaattgt attttattgg gatggataaa atgtttgtgg tttattggat   4262
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtcttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgccccccc   4802
ctcccccagg tagcatgcca ttgatgactt tttgcttagg gccattttat taccagggcc   4862
ttaatattcc taaaaagatg attttttttc atcctttctc ctcttttgat cattgtatct   4922
tgatattaaa aacatgacct tccaatgatt gtagtaaatt aacttctata gttcttttgt   4982
ctctatatgt attcatatat atgctattgt atagagactt caaggagaca tggagatgca   5042
tgcttattct caggttcatt cactaaggtg cttggcagac aaccagtttc taagtgcaga   5102
atgtagttaa gcagcttcat atatgtgcca ggcaatttgt tttgttaaat tttcatctac   5162
ttaaggaaat agggtattgt agcttaggct gatcataccc ttcatttcaa ccttaagctc   5222
tcaacctgca tccatccgac ttgagctatt aagtacttta gttttatcga gtataagtta   5282
acagaaaaag taaattaagc tttgccttta ctattttgaa tttatataca ttctggaaaa   5342
acttagaaac tgttgtatat ttcattagat taaattatat gaaaatgtga ttgtttatag   5402
caaagcctgt gagttgcata caccctaagg aaaactcctt aagtgctcct tgaagagaga   5462
agaaacaatt ctgggtctgg tctttttaag aacaaagcta gactactgta tgttagcact   5522
gtacattaat agtctgttgt gaagcttgag cagtttcctg catagccttg atccttcacc   5582
gttggcattg aaaatagcag tatccctgat gtacttaaaa cttaaagtca ggttttggta   5642
tatttatttg taagtcttaa tttcctctaa atactatatc tctttagcga gacaacctga   5702
aatttattag cacatttggg tatctcttgc ttggcattat ggccagtgtt aactattcag   5762
tggtgaaaaa attacccctc aagacactgg agtgacccca gatgtgtgta gtaagtggca   5822
tggttcaact gtgtggttaa tgataaatat atgacttagt cggtatgatc tggaaagact   5882
tgattgaaag ataattcagc tgacataagg atgagtgagg agtggcaaac tggataaaag   5942
```

```
agtcaagaga cctgtattcc agtgactcct gttttgttta agcattagca agatctgtct   6002

ggggaaactg gatagggcag ttttcttcca tgtttagttt ttgtctcaac atttggaagc   6062

tattgaaggt tttaaaatgg tgtgtattgt ttttttttgg ggggggggtg gccagaatag   6122

tgggtcatct aataaaactg ccatttaaaa gatcaaaaaa aaaaaaaaaa aaaaaaaaa    6181

<210> SEQ ID NO 20
<211> LENGTH: 707
<212> TYPE: PRT
<213> ORGANISM: Mus musculus

<400> SEQUENCE: 20

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335
```

```
Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705
```

<210> SEQ ID NO 21
<211> LENGTH: 6141
<212> TYPE: DNA
<213> ORGANISM: Mus musculus
<220> FEATURE:

<221> NAME/KEY: CDS
<222> LOCATION: (139)..(2262)
<223> OTHER INFORMATION:

<400> SEQUENCE: 21

```
cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt       651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag       747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa       795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt       843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa       891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag       939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag       987
```

-continued

```
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca      1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca      1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct      1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag      1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa      1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct      1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc      1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc      1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585
```

-continued

```
ccc cca cag cag aac act ggc ttt cca cgt agc agt cag cct tat tac     1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg     1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat     2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag     2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga     2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga     2187
Tyr Gln Gln Asn Phe Lys Arg Gly Ser Gly Gln Ser Gly Pro Arg Gly
        670                 675                 680

gcc cca cga ggt cgt gga ggg ccc cca aga ccc aac aga ggg atg ccg     2235
Ala Pro Arg Gly Arg Gly Gly Pro Pro Arg Pro Asn Arg Gly Met Pro
    685                 690                 695

caa atg aac act cag caa gtg aat taa tgtgatacac aggattatgt           2282
Gln Met Asn Thr Gln Gln Val Asn
700                 705

ttaatcgcca aaaacacact ggccagtgta ccataatatg ttaccagaag agttattatc   2342

tatttgttct ccctttcagg aaacttattg taaagggact gttttcatcc cataaagaca   2402

ggactgcaat tgtcagcttt acattacctg gatatggaag gaaactattt ttattctgca   2462

tgttctgtcc taagcgtcat cttgagcctt gcacacaata caatactcag attcctcacc   2522

cttgcttagg agtaaaacat tatatactta tggggtgata atatctccat agttagttga   2582

agtggcttgg aaaaaaaatg caagattgaa tttttgacct tggataaaat ctacaatcag   2642

ccctagaact attcagtggt aattgacaaa gttaaagcat tttctttgaa aggaagatgg   2702

aaggagtgga gtgtggttta gcaaaactgc atttcatagc tttcccatta aattggagca   2762

ccgacagatt aaaagcatac caaattatgc atgggtcctt actcacacaa gtgaggctgg   2822

ctaccagcct tgacatagca ctcactagtc ttctggccaa acgactgtga ttaaaacaca   2882

tgtaaattgc tctttagtag tggatactgt gtaagacaaa gccaaattgc aaatcaggct   2942

ttgattggct cttctggaaa atatgcatca aatatggggg ataatctgga tgggctgctg   3002

ctgtgctcaa tgtgaactat ttagatacct ttggaacact taacagtttc tctgaacaat   3062

gacttacatg gggattggtc ctgtttgtca ttcctcacca taattgcatt gtcatcacta   3122

atccttggat cttgctgtat tgttactcaa attggtaata ggtactgatg gaaatcgcta   3182

atggatggat aatcataaca cttttggtca catgttttct cctgcagcct gaaagttctt   3242

aaagaaaaag atatcaaatg cctgctgcta ccaccctttt aaattgctat ctttagaaaa   3302

gcaccggtat gtgttttaga ttcatttccc tgttttaggg aaatgacagg cagtagtttc   3362

agttctgatg gcaaaacaaa taaaaacatg tttctaaaag ttgtatcttg aaacactggt   3422

gttcaacagc tagcagctaa agtaattcaa cccatgcatt gctagtgtca cagcctttgg   3482

ttatgtctag tagctgtttc tgaagtattt tcatttatct tttgtcaaat ttaaccctgt   3542

ttgaattctc tcctttcctc aaggagacac ttatgttcaa agtgttgatt ctttgcctta   3602

ggtgcataga gagtagacag tttggagatg gaaaggttag cagtgactta gccatatgtt   3662

ctgtgttgga atttgtgcta gcagtttgag cactagctct gcgtgcctat gaactgaatg   3722
```

-continued

```
ctgcttgtcc cattccattt tatgtcatgg agaaataatt ccacttggta acacaaaggc   3782
taagttaatg ttattttctg tacagaaatt aaattttact tttagccttt tgtaaacttt   3842
ttttttttt ttccaagccg gtatcagcta ctcaaaacaa ttctcagata ttcatcatta   3902
gacaactgga gtttttgctg gttttgtagc ctactaaaac tgctgaggct gttgaacatt   3962
ccacattcaa aagttttgta gggtggtgga taatggggaa gcttcaatgt ttattttaaa   4022
ataaataaaa taagttcttg acttttctca tgtgtggtta tggtacatca tattggaagg   4082
gttatctgtt tacttttgcc aagactattt tgccagcacc tacacttgtg tgctttaaaa   4142
gacaactacc tgggatgtac cacaaccata tgttaattgt attttattgg gatggataaa   4202
atgtttgtgg tttattggat aatccctaga tggtgtgtta cgtgtgtaga atataatttt   4262
atgatagtaa gaaagcaaaa ttgaagaaaa taagtttagt attgaatttg agttctgaag   4322
tgaattcagg gaatgtctca cgtttcgggc ttctacccaa agtgtagggc agaaggtgta   4382
aaagttgttt gtagtttgac ttgtttattt tttaagttgc ttattccttt caacagcaac   4442
atatcattag ctgtcattct accattgcag ttctagtgag ttttaacgtc tgcattcaag   4502
actgttttaa aagcaacctc actggacaga gaactgctaa agtcttttcc ttaagatctg   4562
agtctttgtt actcagtatc ttctataata tgcaaatgct tgtctagagg cagaagacct   4622
tttgtttggt caagtgtgta ttttaccaga gtacagggaa ctgatggtcc tacatgtctc   4682
ttagtgtagt aagactataa aatcttttgt acatgcacaa ttcacagtat gtttagatac   4742
cacgtgtata atgccccccc ctcccccagg tagcatgcca ttgatgactt tttgcttagg   4802
gccattttat taccagggcc ttaatattcc taaaaagatg atttttttc atcctttctc   4862
ctcttttgat cattgtatct tgatattaaa aacatgacct tccaatgatt gtagtaaatt   4922
aacttctata gttcttttgt ctctatatgt attcatatat atgctattgt atagagactt   4982
caaggagaca tggagatgca tgcttattct caggttcatt cactaaggtg cttggcagac   5042
aaccagtttc taagtgcaga atgtagttaa gcagcttcat atatgtgcca ggcaatttgt   5102
tttgttaaat tttcatctac ttaaggaaat agggtattgt agcttaggct gatcataccc   5162
ttcatttcaa ccttaagctc tcaacctgca tccatccgac ttgagctatt aagtacttta   5222
gttttatcga gtataagtta acagaaaaag taaattaagc tttgccttta ctattttgaa   5282
tttatataca ttctggaaaa acttagaaac tgttgtatat ttcattagat taaattatat   5342
gaaaatgtga ttgtttatag caaagcctgt gagttgcata caccctaagg aaaactcctt   5402
aagtgctcct tgaagagaga agaaacaatt ctgggtctgg tctttttaag aacaaagcta   5462
gactactgta tgttagcact gtacattaat agtctgttgt gaagcttgag cagtttcctg   5522
catagccttg atccttcacc gttggcattg aaaatagcag tatccctgat gtacttaaaa   5582
cttaaagtca ggttttggta tatttatttg taagtcttaa tttcctctaa atactatatc   5642
tctttagcga gacaacctga aatttattag cacatttggg tatctcttgc ttggcattat   5702
ggccagtgtt aactattcag tggtgaaaaa attacccctc aagacactgg agtgacccca   5762
gatgtgtgta gtaagtggca tggttcaact gtgtggttaa tgataaatat atgacttagt   5822
cggtatgatc tggaaagact tgattgaaag ataattcagc tgacataagg atgagtgagg   5882
agtggcaaac tggataaaag agtcaagaga cctgtattcc agtgactcct gttttgttta   5942
agcattagca agatctgtct ggggaaactg gatagggcag ttttcttcca tgtttagttt   6002
ttgtctcaac atttggaagc tattgaaggt tttaaaatgg tgtgtattgt tttttttgg    6062
```

```
ggggggggtg gccagaatag tgggtcatct aataaaactg ccatttaaaa gatcaaaaaa   6122

aaaaaaaaaa aaaaaaaaa                                                 6141


<210> SEQ ID NO 22
<211> LENGTH: 707
<212> TYPE: PRT
<213> ORGANISM: Mus musculus

<400> SEQUENCE: 22

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
```

-continued

```
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)
<223> OTHER INFORMATION:

<400> SEQUENCE: 23
```

```
cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc     171
                    Met Pro Ser Ala Thr Ser His Ser Gly Ser Gly
                    1               5                   10

agc aaa tcg tcg gga ccg ccg ccg ccg tcc ggt tcc tcc ggg agt gag     219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc     267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc     315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat     363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg     411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca     459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa     507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca     555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat     603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt     651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc     699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag     747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa     795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt     843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa     891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag     939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag     987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca    1035
Gln Ser Glu Val Glu Ser Thr Glu Tyr Val Asn Arg Gln Phe Met Ala
```

```
    285                 290                 295

gaa aca cag ttc agc agt ggt gag aag gag caa gtg gat gag tgg aca      1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct      1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag      1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa      1227
Ser Asp Pro Leu Val Arg Arg Gln Arg Val Gln Asp Leu Met Ala Gln
        350                 355                 360

atg caa ggg ccc tat aat ttc ata cag acg ctt gat cct gcc att gta      1275
Met Gln Gly Pro Tyr Asn Phe Ile Gln Thr Leu Asp Pro Ala Ile Val
    365                 370                 375

tcc gca cag cct atg aac cct acc cag aac atg gat atg cct cag ctg      1323
Ser Ala Gln Pro Met Asn Pro Thr Gln Asn Met Asp Met Pro Gln Leu
380                 385                 390                 395

gtt tgc cct cag gtt cat tct gaa tct aga ctt gcc caa tct aat caa      1371
Val Cys Pro Gln Val His Ser Glu Ser Arg Leu Ala Gln Ser Asn Gln
                400                 405                 410

gtt cct gta caa cca gaa gcc aca cag gtt cct ttg gtt tca tcc aca      1419
Val Pro Val Gln Pro Glu Ala Thr Gln Val Pro Leu Val Ser Ser Thr
            415                 420                 425

agt gag ggg tat aca gca tct cag ccc ttg tac cag cca tct cat gct      1467
Ser Glu Gly Tyr Thr Ala Ser Gln Pro Leu Tyr Gln Pro Ser His Ala
        430                 435                 440

acg gag cag cgg ccg cag aaa gag cca atg gat cag att cag gca aca      1515
Thr Glu Gln Arg Pro Gln Lys Glu Pro Met Asp Gln Ile Gln Ala Thr
    445                 450                 455

ata tct ttg aat aca gac cag act aca gca tcc tca tcc ctt cct gct      1563
Ile Ser Leu Asn Thr Asp Gln Thr Thr Ala Ser Ser Ser Leu Pro Ala
460                 465                 470                 475

gct tct cag cct caa gtg ttc cag gct ggg aca agt aaa cct ttg cac      1611
Ala Ser Gln Pro Gln Val Phe Gln Ala Gly Thr Ser Lys Pro Leu His
                480                 485                 490

agc agt gga atc aat gta aat gca gct cca ttc cag tcc atg caa acg      1659
Ser Ser Gly Ile Asn Val Asn Ala Ala Pro Phe Gln Ser Met Gln Thr
            495                 500                 505

gtg ttc aat atg aat gct cca gtc cct cct gct aat gaa cca gaa acg      1707
Val Phe Asn Met Asn Ala Pro Val Pro Pro Ala Asn Glu Pro Glu Thr
        510                 515                 520

tta aaa caa cag agt cag tac cag gcc act tat aac cag agt ttt tcc      1755
Leu Lys Gln Gln Ser Gln Tyr Gln Ala Thr Tyr Asn Gln Ser Phe Ser
    525                 530                 535

agt cag cct cac caa gtg gaa caa aca gag ctt caa caa gac caa ctg      1803
Ser Gln Pro His Gln Val Glu Gln Thr Glu Leu Gln Gln Asp Gln Leu
540                 545                 550                 555

caa acg gtg gtt ggc act tac cat gga tcc cag gac cag cct cat caa      1851
Gln Thr Val Val Gly Thr Tyr His Gly Ser Gln Asp Gln Pro His Gln
                560                 565                 570

gtg cct ggt aac cac cag caa ccc cca cag cag aac act ggc ttt cca      1899
Val Pro Gly Asn His Gln Gln Pro Pro Gln Gln Asn Thr Gly Phe Pro
            575                 580                 585

cgt agc agt cag cct tat tac aac agt cgt ggg gta tct cga gga ggg      1947
Arg Ser Ser Gln Pro Tyr Tyr Asn Ser Arg Gly Val Ser Arg Gly Gly
        590                 595                 600

tct cgt ggt gcc aga ggc ttg atg aat gga tac agg ggc cct gcc aat      1995
```

-continued

```
Ser Arg Gly Ala Arg Gly Leu Met Asn Gly Tyr Arg Gly Pro Ala Asn
    605                 610                 615

gga ttt aga gga gga tat gat ggt tac cgc cct tca ttc tcg aac act     2043
Gly Phe Arg Gly Gly Tyr Asp Gly Tyr Arg Pro Ser Phe Ser Asn Thr
620                 625                 630                 635

cca aac agt ggt tat tca cag tct cag ttc act gct ccc cgg gac tac     2091
Pro Asn Ser Gly Tyr Ser Gln Ser Gln Phe Thr Ala Pro Arg Asp Tyr
                640                 645                 650

tct ggt tac cag cgg gat gga tat cag cag aat ttc aag cga ggc tct     2139
Ser Gly Tyr Gln Arg Asp Gly Tyr Gln Gln Asn Phe Lys Arg Gly Ser
            655                 660                 665

ggg cag agt gga cca cgg gga gcc cca cga ggt cgt gga ggg ccc cca     2187
Gly Gln Ser Gly Pro Arg Gly Ala Pro Arg Gly Arg Gly Gly Pro Pro
        670                 675                 680

aga ccc aac aga ggg atg ccg caa atg aac act cag caa gtg aat taa     2235
Arg Pro Asn Arg Gly Met Pro Gln Met Asn Thr Gln Gln Val Asn
    685                 690                 695

tgtgatacac aggattatgt ttaatcgcca aaaacacact ggccagtgta ccataatatg   2295

ttaccagaag agttattatc tatttgttct ccctttcagg aaacttattg taaagggact   2355

gttttcatcc cataaagaca ggactgcaat tgtcagcttt acattacctg gatatggaag   2415

gaaactattt ttattctgca tgttctgtcc taagcgtcat cttgagcctt gcacacaata   2475

caatactcag attcctcacc cttgcttagg agtaaaacat tatatactta tggggtgata   2535

atatctccat agttagttga agtggcttgg aaaaaaaatg caagattgaa tttttgacct   2595

tggataaaat ctacaatcag ccctagaact attcagtggt aattgacaaa gttaaagcat   2655

tttctttgaa aggaagatgg aaggagtgga gtgtggttta gcaaaactgc atttcatagc   2715

tttcccatta aattggagca ccgacagatt aaaagcatac caaattatgc atgggtcctt   2775

actcacacaa gtgaggctgg ctaccagcct tgacatagca ctcactagtc ttctggccaa   2835

acgactgtga ttaaaacaca tgtaaattgc tctttagtag tggatactgt gtaagacaaa   2895

gccaaattgc aaatcaggct ttgattggct cttctggaaa atatgcatca aatatggggg   2955

ataatctgga tgggctgctg ctgtgctcaa tgtgaactat ttagatacct ttggaacact   3015

taacagtttc tctgaacaat gacttacatg gggattggtc ctgtttgtca ttcctcacca   3075

taattgcatt gtcatcacta atccttggat cttgctgtat tgttactcaa attggtaata   3135

ggtactgatg gaaatcgcta atggatggat aatcataaca cttttggtca catgttttct   3195

cctgcagcct gaaagttctt aaagaaaaag atatcaaatg cctgctgcta ccaccctttt   3255

aaattgctat ctttagaaaa gcaccggtat gtgttttaga ttcatttccc tgttttaggg   3315

aaatgacagg cagtagtttc agttctgatg gcaaaacaaa taaaaacatg tttctaaaag   3375

ttgtatcttg aaacactggt gttcaacagc tagcagctaa agtaattcaa cccatgcatt   3435

gctagtgtca cagcctttgg ttatgtctag tagctgtttc tgaagtattt tcatttatct   3495

tttgtcaaat ttaaccctgt ttgaattctc tcctttcctc aaggagacac ttatgttcaa   3555

agtgttgatt ctttgcctta ggtgcataga gagtagacag tttggagatg gaaaggttag   3615

cagtgactta gccatatgtt ctgtgttgga atttgtgcta gcagtttgag cactagctct   3675

gcgtgcctat gaactgaatg ctgcttgtcc cattccattt tatgtcatgg agaaataatt   3735

ccacttggta acacaaaggc taagttaatg ttattttctg tacagaaatt aaattttact   3795

tttagccttt tgtaaacttt tttttttttt ttccaagccg gtatcagcta ctcaaaacaa   3855

ttctcagata ttcatcatta gacaactgga gtttttgctg gttttgtagc ctactaaaac   3915
```

-continued

```
tgctgaggct gttgaacatt ccacattcaa aagttttgta gggtggtgga taatggggaa   3975
gcttcaatgt ttattttaaa ataaataaaa taagttcttg acttttctca tgtgtggtta   4035
tggtacatca tattggaagg gttatctgtt tacttttgcc aagactattt tgccagcacc   4095
tacacttgtg tgctttaaaa gacaactacc tgggatgtac cacaaccata tgttaattgt   4155
attttattgg gatggataaa atgtttgtgg tttattggat aatccctaga tggtgtgtta   4215
cgtgtgtaga atataatttt atgatagtaa gaaagcaaaa ttgaagaaaa taagtttagt   4275
attgaatttg agttctgaag tgaattcagg gaatgtctca cgtttcgggc ttctacccaa   4335
agtgtagggc agaaggtgta aaagttgttt gtagtttgac ttgtttattt tttaagttgc   4395
ttattccttt caacagcaac atatcattag ctgtcattct accattgcag ttctagtgag   4455
ttttaacgtc tgcattcaag actgttttaa aagcaacctc actggacaga gaactgctaa   4515
agtcttttcc ttaagatctg agtctttgtt actcagtatc ttctataata tgcaaatgct   4575
tgtctagagg cagaagacct tttgtttggt caagtgtgta ttttaccaga gtacagggaa   4635
ctgatggtcc tacatgtctc ttagtgtagt aagactataa aatcttttgt acatgcacaa   4695
ttcacagtat gtttagatac cacgtgtata atgccccccc ctcccccagg tagcatgcca   4755
ttgatgactt tttgcttagg gccattttat taccagggcc ttaatattcc taaaaagatg   4815
atttttttc atcctttctc ctcttttgat cattgtatct tgatattaaa aacatgacct    4875
tccaatgatt gtagtaaatt aacttctata gttcttttgt ctctatatgt attcatatat   4935
atgctattgt atagagactt caaggagaca tggagatgca tgcttattct caggttcatt   4995
cactaaggtg cttggcagac aaccagtttc taagtgcaga atgtagttaa gcagcttcat   5055
atatgtgcca ggcaatttgt tttgttaaat tttcatctac ttaaggaaat agggtattgt   5115
agcttaggct gatcataccc ttcatttcaa ccttaagctc tcaacctgca tccatccgac   5175
ttgagctatt aagtacttta gttttatcga gtataagtta acagaaaaag taaattaagc   5235
tttgccttta ctattttgaa tttatataca ttctggaaaa acttagaaac tgttgtatat   5295
ttcattagat taaattatat gaaaatgtga ttgtttatag caaagcctgt gagttgcata   5355
caccctaagg aaaactcctt aagtgctcct tgaagagaga agaaacaatt ctgggtctgg   5415
tctttttaag aacaaagcta gactactgta tgttagcact gtacattaat agtctgttgt   5475
gaagcttgag cagtttcctg catagccttg atccttcacc gttggcattg aaaatagcag   5535
tatccctgat gtacttaaaa cttaaagtca ggttttggta tatttatttg taagtcttaa   5595
tttcctctaa atactatatc tctttagcga gacaacctga aatttattag cacatttggg   5655
tatctcttgc ttggcattat ggccagtgtt aactattcag tggtgaaaaa attacccctc   5715
aagacactgg agtgacccca gatgtgtgta gtaagtggca tggttcaact gtgtggttaa   5775
tgataaatat atgacttagt cggtatgatc tggaaagact tgattgaaag ataattcagc   5835
tgacataagg atgagtgagg agtggcaaac tggataaaag agtcaagaga cctgtattcc   5895
agtgactcct gttttgttta agcattagca agatctgtct ggggaaactg gatagggcag   5955
ttttcttcca tgtttagttt ttgtctcaac atttggaagc tattgaaggt tttaaaatgg   6015
tgtgtattgt ttttttttgg gggggggtg gccagaatag tgggtcatct aataaaactg    6075
ccatttaaaa gatcaaaaaa aaaaaaaaaa aaaaaaaaa                          6114
```

<210> SEQ ID NO 24
<211> LENGTH: 698
<212> TYPE: PRT
<213> ORGANISM: Mus musculus -continued

<400> SEQUENCE: 24

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
```

```
                405                 410                 415

Glu Ala Thr Gln Val Pro Leu Val Ser Ser Thr Ser Glu Gly Tyr Thr
            420                 425                 430

Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Ser Gln Pro His Gln
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
            660                 665                 670

Arg Gly Ala Pro Arg Gly Arg Gly Gly Pro Pro Arg Pro Asn Arg Gly
        675                 680                 685

Met Pro Gln Met Asn Thr Gln Gln Val Asn
    690                 695


<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)
<223> OTHER INFORMATION:

<400> SEQUENCE: 25

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
```

-continued

```
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag      322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg      370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335
```

-continued

```
cca gag ccc cac tct ttg act cca gtg gct cag tca gat cca ctt gtg      1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat      1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat      1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat      1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc      1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg      1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag      1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag      1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca      1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt      1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag      1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat      1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac      1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa      1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac      1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac      1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta      2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg      2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca      2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct      2146
Phe Ser Asn Thr Pro Asn Ser Gly Tyr Ser Gln Ser Gln Phe Thr Ala
                645                 650                 655
```

-continued

```
ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt aat     2242
Lys Arg Gly Ser Gly Gln Ser Gly Pro Arg Gly Ala Pro Arg Gly Asn
        675                 680                 685

ata ttg tgg tgg tga tcctagctcc tatgtggagc ttctgttctg gccttggaag     2297
Ile Leu Trp Trp
    690

aactgttcat agtccgcatg taggttacat gttaggaata catttatctt ttccagactt   2357

gttgctaaag attaaatgaa atgctctgtt tctaaaattt catcttgaat ccaaatttta   2417

atttttgaat gactttccct gctgttgtct tcaaaatcag aacattttct ctgcctcaga   2477

aaagcgtttt tccaactgga aatttatttt tcaggtctta aaacctgcta aatgttttta   2537

ggaagtacct actgaaactt tttgtaagac atttttggaa cgagcttgaa catttatata   2597

aatttattac cctctttgat ttttgaaaca tgcatattat atttaggctg agaagccctt   2657

caaatggcca gataagccac agttttagct agagaaccat ttagaattga cataactaat   2717

ctaaacttga acacttttag gaccaatgtt agtgttctaa ataccaacat atttctgatg   2777

tttaaacaga tctcccaaat tcttaggacc ttgatgtcat taaaatttag aatgacaagc   2837

ttaagaggct ttagtttcat ttgtttttca agtaatgaaa aataatttct tacatgggca   2897

gatagttaat ttgttgaaca attacaggta gcatttcatg taatctgatg ttctaaatgg   2957

ttctcttatt gaaggaggtt aaagaattag gtttcttaca gtttttggct ggccatgaca   3017

tgtataaaat gtatattaag gaggaattat aaagtacttt aatttgaatg ctagtggcaa   3077

ttgatcatta agaaagtact ttaaagcaaa aggttaatgg gtcatctggg aaaaatactg   3137

aagtatcaaa ggtatttgca tgtgaatgtg ggttatgttc ttctatccca ccttgtagca   3197

tattctatga aagttgagtt aaatgatagc taaaatatct gtttcaacag catgtaaaaa   3257

gttattttaa ctgttacaag tcattataca attttgaatg ttctgtagtt tctttttaac   3317

agtttaggta caaaggtctg ttttcattct ggtgcttttt attaattttg atagtatgat   3377

gtcacttcct attgaaatgt aagctagcgt gtaccttaga atgtgagctc catgagagca   3437

ggtaccttgt ttgtcttcac tgctgtatct attcccaacg cctcatgaca gtgcctggca   3497

catagtaggc actcaataaa tacttgttga atgaatgaaa aaaaaaaaaa a            3548


<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
```

-continued

```
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510
```

```
Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)
<223> OTHER INFORMATION:

<400> SEQUENCE: 27

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca       459
Asp Ala Val Ser Lys Tyr Gln Glu Val Thr Asn Asn Leu Glu Phe Ala
```

-continued

```
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa     1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct     1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct     1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc     1419
```

-continued

```
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc      1611
Thr Thr Ala Ser Ser Ser Leu Pro Ala Ala Ser Gln Pro Gln Val Phe
            480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
            560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
            640                 645                 650

tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680

gcc cca cga ggt aat ata ttg tgg tgg tga tcctagctcc tatgtggagc       2237
Ala Pro Arg Gly Asn Ile Leu Trp Trp
    685                 690

ttctgttctg gccttggaag aactgttcat agtccgcatg taggttacat gttaggaata   2297

catttatctt ttccagactt gttgctaaag attaaatgaa atgctctgtt tctaaaattt   2357

catcttgaat ccaaatttta atttttgaat gactttccct gctgttgtct tcaaaatcag   2417

aacattttct ctgcctcaga aaagcgtttt tccaactgga aatttatttt tcaggtctta   2477
```

-continued

```
aaacctgcta aatgttttta ggaagtacct actgaaactt tttgtaagac atttttggaa   2537

cgagcttgaa catttatata aatttattac cctctttgat ttttgaaaca tgcatattat   2597

atttaggctg agaagccctt caaatggcca gataagccac agttttagct agagaaccat   2657

ttagaattga cataactaat ctaaacttga acacttttag gaccaatgtt agtgttctaa   2717

ataccaacat atttctgatg tttaaacaga tctcccaaat tcttaggacc ttgatgtcat   2777

taaaatttag aatgacaagc ttaagaggct ttagtttcat ttgtttttca agtaatgaaa   2837

aataatttct tacatgggca gatagttaat ttgttgaaca attacaggta gcatttcatg   2897

taatctgatg ttctaaatgg ttctcttatt gaaggaggtt aaagaattag gtttcttaca   2957

gtttttggct ggccatgaca tgtataaaat gtatattaag gaggaattat aaagtacttt   3017

aatttgaatg ctagtggcaa ttgatcatta agaaagtact ttaaagcaaa aggttaatgg   3077

gtcatctggg aaaaatactg aagtatcaaa ggtatttgca tgtgaatgtg ggttatgttc   3137

ttctatccca ccttgtagca tattctatga aagttgagtt aaatgatagc taaaatatct   3197

gtttcaacag catgtaaaaa gttattttaa ctgttacaag tcattataca attttgaatg   3257

ttctgtagtt tctttttaac agtttaggta caaaggtctg ttttcattct ggtgcttttt   3317

attaatttg atagtatgat gtcacttcct attgaaatgt aagctagcgt gtaccttaga   3377

atgtgagctc catgagagca ggtaccttgt ttgtcttcac tgctgtatct attcccaacg   3437

cctcatgaca gtgcctggca catagtaggc actcaataaa tacttgttga atgaatgaaa   3497

aaaaaaaaaa a                                                        3508

<210> SEQ ID NO 28
<211> LENGTH: 692
<212> TYPE: PRT
<213> ORGANISM: Mus musculus

<400> SEQUENCE: 28

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190
```

-continued

```
Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605
```

```
Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)
<223> OTHER INFORMATION:

<400> SEQUENCE: 29

atg ccc tcg gct acc aac ggc acc atg gcg agc agc agc ggg aag gcg       48
Met Pro Ser Ala Thr Asn Gly Thr Met Ala Ser Ser Ser Gly Lys Ala
1               5                   10                  15

ggc ccg ggc ggc aac gag cag gcc ccg gcg gcg gca gcg gcg gcc ccg       96
Gly Pro Gly Gly Asn Glu Gln Ala Pro Ala Ala Ala Ala Ala Ala Pro
            20                  25                  30

cag gcg tcg ggc ggc agc atc acc tcg gtt cag acc gag gcc atg aag      144
Gln Ala Ser Gly Gly Ser Ile Thr Ser Val Gln Thr Glu Ala Met Lys
        35                  40                  45

cag atc ttg gga gtg atc gac aaa aag ctc cgc aac ctc gag aag aaa      192
Gln Ile Leu Gly Val Ile Asp Lys Lys Leu Arg Asn Leu Glu Lys Lys
    50                  55                  60

aag agc aaa ctt gac gat tac cag gaa cga atg aac aag ggg gaa cgt      240
Lys Ser Lys Leu Asp Asp Tyr Gln Glu Arg Met Asn Lys Gly Glu Arg
65                  70                  75                  80

cta aat caa gat caa ctg gat gca gtg tca aaa tac cag gaa gtg aca      288
Leu Asn Gln Asp Gln Leu Asp Ala Val Ser Lys Tyr Gln Glu Val Thr
                85                  90                  95

aat aac ctg gaa ttc gct aaa gaa ctg cag agg agc ttt atg gca ctg      336
Asn Asn Leu Glu Phe Ala Lys Glu Leu Gln Arg Ser Phe Met Ala Leu
            100                 105                 110

agc caa gat atc cag aaa aca ata aaa aag acg gct cgc agg gag cag      384
Ser Gln Asp Ile Gln Lys Thr Ile Lys Lys Thr Ala Arg Arg Glu Gln
        115                 120                 125

ctg atg aga gaa gag gct gag cag aag cgt tta aag act gtg cta gag      432
Leu Met Arg Glu Glu Ala Glu Gln Lys Arg Leu Lys Thr Val Leu Glu
    130                 135                 140

ctg cag ttc att ttg gac aag ttg ggt gac gat gaa gtg cgc agt gac      480
Leu Gln Phe Ile Leu Asp Lys Leu Gly Asp Asp Glu Val Arg Ser Asp
145                 150                 155                 160

ttg aaa caa gga tca aat gga gta ccg gta ctg aca gag gag gaa ctg      528
Leu Lys Gln Gly Ser Asn Gly Val Pro Val Leu Thr Glu Glu Glu Leu
                165                 170                 175

aca atg ctg gat gaa ttt tac aag cta gtt tac cct gaa agg gac atg      576
Thr Met Leu Asp Glu Phe Tyr Lys Leu Val Tyr Pro Glu Arg Asp Met
            180                 185                 190

aac atg agg ttg aat gag cag tat gag caa gca tct gtt cac ctg tgg      624
```

-continued

```
Asn Met Arg Leu Asn Glu Gln Tyr Glu Gln Ala Ser Val His Leu Trp
        195                 200                 205

gac tta ctg gaa ggg aag gaa aaa ccc gtt tgt gga aca acc tat aaa      672
Asp Leu Leu Glu Gly Lys Glu Lys Pro Val Cys Gly Thr Thr Tyr Lys
    210                 215                 220

gcc ctg aag gag gtt gtt gaa cgt att ctt caa act agt tac ttt gat      720
Ala Leu Lys Glu Val Val Glu Arg Ile Leu Gln Thr Ser Tyr Phe Asp
225                 230                 235                 240

agc acc cat aac cat cag aac ggg tta tgt gag gaa gaa gag gca gca      768
Ser Thr His Asn His Gln Asn Gly Leu Cys Glu Glu Glu Glu Ala Ala
                245                 250                 255

ccc aca cct gca gta gaa gac act gta gca gaa gct gag cct gat cca      816
Pro Thr Pro Ala Val Glu Asp Thr Val Ala Glu Ala Glu Pro Asp Pro
            260                 265                 270

gca gaa gaa ttt act gaa cct act gaa gtt gaa tcg act gag tat gta      864
Ala Glu Glu Phe Thr Glu Pro Thr Glu Val Glu Ser Thr Glu Tyr Val
        275                 280                 285

aac aga caa ttc atg gca gag act cag ttc agc agt agt gag aag gaa      912
Asn Arg Gln Phe Met Ala Glu Thr Gln Phe Ser Ser Ser Glu Lys Glu
    290                 295                 300

cag gta gat gag tgg aca gtt gaa acg gtt gag gtt gta aat tca ctg      960
Gln Val Asp Glu Trp Thr Val Glu Thr Val Glu Val Val Asn Ser Leu
305                 310                 315                 320

cag caa caa aca caa gct aca tct cct cca gtt cct gaa cct cat aca     1008
Gln Gln Gln Thr Gln Ala Thr Ser Pro Pro Val Pro Glu Pro His Thr
                325                 330                 335

ctc act act gtg gct caa gca gat cct ctt gtt aga aga cag aga gta     1056
Leu Thr Thr Val Ala Gln Ala Asp Pro Leu Val Arg Arg Gln Arg Val
            340                 345                 350

cag gac ctt atg gcc cag atg cag ggt cca tat aac ttc atg cag gac     1104
Gln Asp Leu Met Ala Gln Met Gln Gly Pro Tyr Asn Phe Met Gln Asp
        355                 360                 365

tct atg ctg gag ttt gag aac cag aca ctt gat cct gcc att gta tct     1152
Ser Met Leu Glu Phe Glu Asn Gln Thr Leu Asp Pro Ala Ile Val Ser
    370                 375                 380

gca cag ccc atg aat cca gca cag aat ttg gac atg ccg caa atg gtc     1200
Ala Gln Pro Met Asn Pro Ala Gln Asn Leu Asp Met Pro Gln Met Val
385                 390                 395                 400

tgc cct cca gtt cat act gag tca aga ctt gcc cag cct aat caa gtt     1248
Cys Pro Pro Val His Thr Glu Ser Arg Leu Ala Gln Pro Asn Gln Val
                405                 410                 415

cct gtg caa cca gaa gct acg cag gtt ccc ttg gtt tca tct aca agt     1296
Pro Val Gln Pro Glu Ala Thr Gln Val Pro Leu Val Ser Ser Thr Ser
            420                 425                 430

gag gga tat aca gcc tcc cag ccc atg tat cag cct tct cat acc aca     1344
Glu Gly Tyr Thr Ala Ser Gln Pro Met Tyr Gln Pro Ser His Thr Thr
        435                 440                 445

gag caa cgg cca cag aag gaa tcc att gac cag att cag gct tca atg     1392
Glu Gln Arg Pro Gln Lys Glu Ser Ile Asp Gln Ile Gln Ala Ser Met
    450                 455                 460

tca ctg aat gca gac cag acc ccg tca tca tca tca ctt ccc act gca     1440
Ser Leu Asn Ala Asp Gln Thr Pro Ser Ser Ser Ser Leu Pro Thr Ala
465                 470                 475                 480

tcc cag ccg caa gtt ttc caa gct gga tct agc aaa cct ttg cat agc     1488
Ser Gln Pro Gln Val Phe Gln Ala Gly Ser Ser Lys Pro Leu His Ser
                485                 490                 495

agc gga atc aat gtt aat gca gct cca ttc caa tcc atg caa aca gta     1536
Ser Gly Ile Asn Val Asn Ala Ala Pro Phe Gln Ser Met Gln Thr Val
            500                 505                 510
```

-continued

```
ttc aac atg aat gca cct gtt cct cct gtt aat gag cca gaa gcc ctt      1584
Phe Asn Met Asn Ala Pro Val Pro Pro Val Asn Glu Pro Glu Ala Leu
        515                 520                 525

aag caa caa aat cag tac cag gcc agt tac aac cag agt ttc tcc aat      1632
Lys Gln Gln Asn Gln Tyr Gln Ala Ser Tyr Asn Gln Ser Phe Ser Asn
    530                 535                 540

cag cca cac caa gta gaa caa tca gat ctt cag caa gaa cag ctc cag      1680
Gln Pro His Gln Val Glu Gln Ser Asp Leu Gln Gln Glu Gln Leu Gln
545                 550                 555                 560

aca gtg gtt ggt act tac cat ggt tct ccg gac cag acc cat caa gtg      1728
Thr Val Val Gly Thr Tyr His Gly Ser Pro Asp Gln Thr His Gln Val
                565                 570                 575

gca gga aac cac cag caa cct ccc cag cag aat act gga ttt cca cgc      1776
Ala Gly Asn His Gln Gln Pro Pro Gln Gln Asn Thr Gly Phe Pro Arg
            580                 585                 590

aac agt cag cct tat tac aac agt cgg gga gtg tct cgt ggt gga tca      1824
Asn Ser Gln Pro Tyr Tyr Asn Ser Arg Gly Val Ser Arg Gly Gly Ser
        595                 600                 605

cgt ggg act cgt gga ttg atg aat ggt tac agg gga cct gca aat gga      1872
Arg Gly Thr Arg Gly Leu Met Asn Gly Tyr Arg Gly Pro Ala Asn Gly
    610                 615                 620

ttt aga gga gga tat gat ggc tac cgt cct tca ttt tcc aac act ccg      1920
Phe Arg Gly Gly Tyr Asp Gly Tyr Arg Pro Ser Phe Ser Asn Thr Pro
625                 630                 635                 640

aac agt ggt tac acg cag ccc caa ttt aat gct cct cga gat tat tca      1968
Asn Ser Gly Tyr Thr Gln Pro Gln Phe Asn Ala Pro Arg Asp Tyr Ser
                645                 650                 655

aac tac cag cgg gat gga tat cag cag aac ttc aaa cgt ggt tct gga      2016
Asn Tyr Gln Arg Asp Gly Tyr Gln Gln Asn Phe Lys Arg Gly Ser Gly
            660                 665                 670

caa agt ggg cct cgg gga gct cct cga ggt cgt gga ggg ccc cca aga      2064
Gln Ser Gly Pro Arg Gly Ala Pro Arg Gly Arg Gly Gly Pro Pro Arg
        675                 680                 685

cca aac aga ggg atg cct caa atg aac gct cag caa gtg aat taa          2109
Pro Asn Arg Gly Met Pro Gln Met Asn Ala Gln Gln Val Asn
    690                 695                 700


<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125
```

-continued

```
Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Glu Ala Ala
                245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Ser Glu Lys Glu
    290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
        355                 360                 365

Ser Met Leu Glu Phe Glu Asn Gln Thr Leu Asp Pro Ala Ile Val Ser
    370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
        435                 440                 445

Glu Gln Arg Pro Gln Lys Glu Ser Ile Asp Gln Ile Gln Ala Ser Met
    450                 455                 460

Ser Leu Asn Ala Asp Gln Thr Pro Ser Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
            500                 505                 510

Phe Asn Met Asn Ala Pro Val Pro Pro Val Asn Glu Pro Glu Ala Leu
        515                 520                 525

Lys Gln Gln Asn Gln Tyr Gln Ala Ser Tyr Asn Gln Ser Phe Ser Asn
    530                 535                 540
```

```
Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
        595                 600                 605

Arg Gly Thr Arg Gly Leu Met Asn Gly Tyr Arg Gly Pro Ala Asn Gly
    610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
                645                 650                 655

Asn Tyr Gln Arg Asp Gly Tyr Gln Gln Asn Phe Lys Arg Gly Ser Gly
            660                 665                 670

Gln Ser Gly Pro Arg Gly Ala Pro Arg Gly Arg Gly Gly Pro Pro Arg
        675                 680                 685

Pro Asn Arg Gly Met Pro Gln Met Asn Ala Gln Gln Val Asn
    690                 695                 700


<210> SEQ ID NO 31
<211> LENGTH: 20
<212> TYPE: DNA
<213> ORGANISM: Artificial
<220> FEATURE:
<223> OTHER INFORMATION: T3 primer

<400> SEQUENCE: 31

aattaaccct cactaaaggg                                                   20


<210> SEQ ID NO 32
<211> LENGTH: 19
<212> TYPE: DNA
<213> ORGANISM: Artificial
<220> FEATURE:
<223> OTHER INFORMATION: T7 primer

<400> SEQUENCE: 32

taatacgact cactatagg                                                    19


<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33

aaggtttgaa tggagtgc                                                     18


<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34

tgctcctttt caccactg                                                     18
```

-continued

<210> SEQ ID NO 35
<211> LENGTH: 18
<212> TYPE: DNA
<213> ORGANISM: Artificial
<220> FEATURE:
<223> OTHER INFORMATION: GAPDH primer

<400> SEQUENCE: 35
gggctgcttt taactctg 18

<210> SEQ ID NO 36
<211> LENGTH: 18
<212> TYPE: DNA
<213> ORGANISM: Artificial
<220> FEATURE:
<223> OTHER INFORMATION: GAPDH primer

<400> SEQUENCE: 36
ccaggaaatg agcttgac 18

<210> SEQ ID NO 37
<211> LENGTH: 27
<212> TYPE: DNA
<213> ORGANISM: Artificial
<220> FEATURE:
<223> OTHER INFORMATION: primer

<400> SEQUENCE: 37
catatggcat taagtcaaga tattcag 27

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
ggtacctttg cggcatccct ctg 23

<210> SEQ ID NO 39
<211> LENGTH: 21
<212> TYPE: DNA
<213> ORGANISM: Artificial
<220> FEATURE:
<223> OTHER INFORMATION: primer

<400> SEQUENCE: 39
catatgccgt cggccaccag c 21

<210> SEQ ID NO 40
<211> LENGTH: 22
<212> TYPE: DNA
<213> ORGANISM: Artificial
<220> FEATURE:
<223> OTHER INFORMATION: primer

<400> SEQUENCE: 40
ggtaccattc acttgctgag tg 22

<210> SEQ ID NO 41
<211> LENGTH: 23
<212> TYPE: DNA
<213> ORGANISM: Artificial
<220> FEATURE:
<223> OTHER INFORMATION: primer

```
<400> SEQUENCE: 41

gagctcatgc cctcggccac cag                                              23


<210> SEQ ID NO 42
<211> LENGTH: 23
<212> TYPE: DNA
<213> ORGANISM: Artificial
<220> FEATURE:
<223> OTHER INFORMATION: primer

<400> SEQUENCE: 42

ctcgagttaa ttcacttgct gag                                              23


<210> SEQ ID NO 43
<211> LENGTH: 14
<212> TYPE: PRT
<213> ORGANISM: Homo sapiens

<400> SEQUENCE: 43

Arg Asn Leu Glu Lys Lys Lys Gly Lys Leu Asp Asp Tyr Gln
1               5                   10


<210> SEQ ID NO 44
<211> LENGTH: 148
<212> TYPE: PRT
<213> ORGANISM: Mus musculus

<400> SEQUENCE: 44

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145


<210> SEQ ID NO 45
<211> LENGTH: 132
<212> TYPE: PRT
<213> ORGANISM: Mus musculus

<400> SEQUENCE: 45

Ala Val Leu Arg Cys Ser Arg Gly Leu Leu Val Ile Trp Ile Ser Asp
1               5                   10                  15

Ile Gln Leu Thr Gln Ser Pro Ser Ser Leu Ala Val Thr Ala Gly Glu
            20                  25                  30
```

```
Lys Val Thr Met Ser Cys Lys Ser Ser Gln Ser Leu Leu Trp Ser Val
        35                  40                  45

Asn Gln Lys Asn Tyr Leu Ser Trp Tyr Gln Gln Lys Gln Arg Gln Pro
    50                  55                  60

Pro Lys Leu Leu Ile Tyr Gly Ala Ser Ile Arg Glu Ser Trp Val Pro
65                  70                  75                  80

Asp Arg Phe Thr Gly Ser Gly Ser Gly Thr Asp Phe Thr Leu Thr Ile
                85                  90                  95

Ser Asn Val His Ala Glu Asp Leu Ala Val Tyr Tyr Cys Gln His Asn
            100                 105                 110

His Gly Ser Phe Leu Pro Ser Arg Ser Glu Gln Val Pro Ser Trp Arg
        115                 120                 125

Ser Asn Asn Arg
    130


<210> SEQ ID NO 46
<211> LENGTH: 117
<212> TYPE: PRT
<213> ORGANISM: Mus musculus

<400> SEQUENCE: 46

Arg Thr Thr Ser His Met Asp Ser Asp Ile Gln Leu Thr Gln Ser Pro
1               5                   10                  15

Ala Ser Leu Ser Ala Ser Val Gly Glu Thr Val Thr Ile Thr Cys Arg
            20                  25                  30

Ala Ser Gly Asn Ile His Asn Tyr Leu Ala Trp Tyr Gln Gln Lys Gln
        35                  40                  45

Gly Lys Ser Pro Gln Leu Leu Val Tyr Asn Ala Lys Thr Leu Ala Asp
    50                  55                  60

Gly Val Pro Ser Arg Phe Ser Gly Ser Gly Ser Gly Thr Gln Tyr Ser
65                  70                  75                  80

Leu Lys Ile Asn Ser Leu Gln Pro Glu Asp Phe Gly Ser Tyr Tyr Cys
                85                  90                  95

Gln His Phe Trp Ser Thr Leu Thr Phe Gly Gly Gly Thr Lys Leu Glu
            100                 105                 110

Ile Lys Gln Ser Asp
        115


<210> SEQ ID NO 47
<211> LENGTH: 94
<212> TYPE: PRT
<213> ORGANISM: Mus musculus

<400> SEQUENCE: 47

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Ala Gly Thr Lys Leu Glu Ile Lys Gln
                85                  90
```

<210> SEQ ID NO 48
<211> LENGTH: 105
<212> TYPE: PRT
<213> ORGANISM: Mus musculus

<400> SEQUENCE: 48

```
Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Arg Ser Asn
            100                 105
```

<210> SEQ ID NO 49
<211> LENGTH: 100
<212> TYPE: PRT
<213> ORGANISM: Mus musculus

<400> SEQUENCE: 49

```
Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100
```

<210> SEQ ID NO 50
<211> LENGTH: 90
<212> TYPE: PRT
<213> ORGANISM: Mus musculus

<400> SEQUENCE: 50

```
Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
            20                  25                  30

Tyr Leu Ala Ser Asn Arg Asp Thr Gly Leu Pro Asp Arg Phe Pro Gly
        35                  40                  45

Arg Gly Ser Gly Thr Asp Phe Thr Leu Asn Ile Thr Asn Val Gln Ser
    50                  55                  60

Glu Asp Leu Glu Asp Tyr Phe Cys Leu Gln His Cys Asn Tyr Pro Asn
```

```
65                  70                  75                  80

Glu Phe Arg Gly Cys Thr Lys Val Pro Ile
                85                  90


<210> SEQ ID NO 51
<211> LENGTH: 116
<212> TYPE: PRT
<213> ORGANISM: Mus musculus

<400> SEQUENCE: 51

Leu Gln Glu Ser Gly Ala Glu Leu Ala Arg Pro Gly Ala Ser Val Lys
1               5                   10                  15

Leu Ser Cys Lys Ala Ser Gly Tyr Thr Phe Thr Ser Tyr Trp Met Gln
            20                  25                  30

Trp Val Lys Gln Arg Pro Gly Gln Gly Leu Glu Trp Ile Gly Ala Ile
        35                  40                  45

Tyr Pro Gly Asp Gly Asp Thr Arg Tyr Thr Gln Lys Phe Lys Gly Lys
    50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95

Glu Tyr Gly Asn Tyr Phe Ala Tyr Trp Gly Gln Gly Thr Thr Val Thr
            100                 105                 110

Val Ser Ser Asn
        115


<210> SEQ ID NO 52
<211> LENGTH: 100
<212> TYPE: PRT
<213> ORGANISM: Mus musculus

<400> SEQUENCE: 52

Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
            20                  25                  30

Lys Ser Pro Lys Thr Leu Ile Tyr Arg Ala Asn Arg Leu Val Asp Gly
        35                  40                  45

Val Pro Ser Arg Phe Ser Gly Ser Gly Ser Gly Gln Asp Tyr Ser Leu
    50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys
            100


<210> SEQ ID NO 53
<211> LENGTH: 108
<212> TYPE: PRT
<213> ORGANISM: Mus musculus

<400> SEQUENCE: 53

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
            20                  25                  30
```

-continued

```
Trp Ile Gly Arg Ile Asp Pro Ala Asn Gly Asn Thr Lys Tyr Asp Pro
        35                  40                  45

Lys Phe Gln Gly Lys Ala Thr Ile Thr Ala Asp Thr Ser Ser Asn Thr
    50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Tyr Gly Ser Ser Leu Ala Tyr
                85                  90                  95

Trp Gly Gln Gly Thr Thr Val Thr Val Ser Ser Lys
            100                 105


<210> SEQ ID NO 54
<211> LENGTH: 104
<212> TYPE: PRT
<213> ORGANISM: Mus musculus

<400> SEQUENCE: 54

Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
            20                  25                  30

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100


<210> SEQ ID NO 55
<211> LENGTH: 109
<212> TYPE: PRT
<213> ORGANISM: Mus musculus

<400> SEQUENCE: 55

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105


<210> SEQ ID NO 56
<211> LENGTH: 94
<212> TYPE: PRT
<213> ORGANISM: Mus musculus
```

<400> SEQUENCE: 56

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90

<210> SEQ ID NO 57
<211> LENGTH: 111
<212> TYPE: PRT
<213> ORGANISM: Mus musculus

<400> SEQUENCE: 57

Pro Ala Cys Leu Pro Gly Gly Ser Leu Arg Leu Ser Cys Ala Thr Ser
1               5                   10                  15

Gly Phe Thr Phe Thr Asp Tyr Tyr Met Ser Trp Val Arg Gln Pro Pro
            20                  25                  30

Gly Lys Ala Leu Glu Trp Leu Gly Phe Ile Arg Asn Lys Ala Asn Gly
        35                  40                  45

Tyr Thr Thr Glu Tyr Ser Ala Ser Val Lys Gly Arg Phe Thr Ile Ser
    50                  55                  60

Arg Asp Asn Ser Gln Ser Ile Leu Tyr Leu Gln Met Asn Thr Leu Arg
65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
            100                 105                 110

<210> SEQ ID NO 58
<211> LENGTH: 102
<212> TYPE: PRT
<213> ORGANISM: Mus musculus

<400> SEQUENCE: 58

Arg Leu Pro Phe Tyr Ser Leu Glu Gln Arg Ala Thr Ile Ser Tyr Arg
1               5                   10                  15

Ala Ser Lys Asn Val Ser Thr Ser Gly Tyr Ser Tyr Met His Trp Asn
            20                  25                  30

Gln Gln Lys Pro Gly Gln Pro Pro Lys Leu Leu Ile Tyr Leu Val Ser
        35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Glu Asp Ala Ala
65                  70                  75                  80

Thr Tyr Tyr Cys Gln His Ile Arg Glu Leu Thr Arg Ser Glu Leu Val
                85                  90                  95

Pro Ser Trp Lys Ser Asn
            100

<210> SEQ ID NO 59
<211> LENGTH: 101
<212> TYPE: PRT
<213> ORGANISM: Mus musculus

<400> SEQUENCE: 59

```
Val Ser Cys Lys Ala Ser Gly Tyr Thr Phe Thr Ser Tyr Trp Met His
1               5                   10                  15

Trp Val Lys Gln Arg Pro Gly Gln Gly Leu Glu Trp Ile Gly Met Ile
            20                  25                  30

Asp Pro Ser Asn Ser Glu Thr Arg Leu Asn Gln Lys Phe Lys Asp Lys
        35                  40                  45

Ala Thr Leu Asn Val Asp Lys Ser Ser Asn Thr Ala Tyr Met Gln Leu
    50                  55                  60

Ser Ser Leu Thr Ser Glu Asp Ser Ala Val Tyr Tyr Cys Ala Arg Gly
65                  70                  75                  80

Leu Arg His Tyr Trp Tyr Phe Asp Val Trp Gly Gln Gly Thr Thr Val
                85                  90                  95

Thr Val Ser Ser Lys
            100
```

<210> SEQ ID NO 60
<211> LENGTH: 99
<212> TYPE: PRT
<213> ORGANISM: Mus musculus

<400> SEQUENCE: 60

```
Thr Ile Leu Trp Arg Glu Gly Pro Phe Ser Tyr Arg Ala Ser Lys Ser
1               5                   10                  15

Val Ser Thr Ser Gly Tyr Ser Tyr Met His Trp Asn Gln Gln Lys Pro
            20                  25                  30

Gly Gln Pro Pro Arg Leu Leu Ile Tyr Leu Val Ser Asn Leu Glu Ser
        35                  40                  45

Gly Val Pro Ala Arg Phe Ser Gly Ser Gly Ser Gly Thr Asp Phe Thr
    50                  55                  60

Leu Asn Ile His Pro Val Glu Glu Glu Asp Ala Ala Thr Tyr Tyr Cys
65                  70                  75                  80

Gln His Ile Arg Glu Leu Thr Arg Ser Glu Glu Val Pro Ser Trp Arg
                85                  90                  95

Ser Asn Lys
```

<210> SEQ ID NO 61
<211> LENGTH: 58
<212> TYPE: PRT
<213> ORGANISM: Homo sapiens

<400> SEQUENCE: 61

```
Val Phe Gln Ser Asn Tyr Phe Asp Ser Thr His Asn His Gln Asn Gly
1               5                   10                  15

Leu Cys Glu Glu Glu Glu Ala Ala Ser Ala Pro Ala Val Glu Asp Gln
            20                  25                  30

Val Pro Glu Ala Glu Pro Glu Pro Ala Glu Glu Tyr Thr Glu Gln Ser
        35                  40                  45

Glu Val Glu Ser Thr Glu Tyr Val Asn Arg
    50                  55
```

<210> SEQ ID NO 62

-continued

```
<211> LENGTH: 15
<212> TYPE: PRT
<213> ORGANISM: Homo sapiens

<400> SEQUENCE: 62

Tyr Thr Glu Gln Ser Glu Val Glu Ser Thr Glu Tyr Val Asn Arg
1               5                   10                  15


<210> SEQ ID NO 63
<211> LENGTH: 11
<212> TYPE: PRT
<213> ORGANISM: Homo sapiens

<400> SEQUENCE: 63

Ser Glu Val Glu Ser Thr Glu Tyr Val Asn Arg
1               5                   10
```

METHOD FOR DETECTING CANCER USING CAPRIN-1 AS A MARKER

TECHNICAL FIELD

The present invention relates to a method for detecting cancer using CAPRIN-1 as a tumor marker.

BACKGROUND ART

Cancer is the leading cause of death. Treatment currently performed for cancer is mainly symptomatic therapy that mostly consists of surgical therapy with a combination of radiation therapy and chemotherapy. Owing to advancements in medical technology, cancer is now almost a curable disease if it can be detected early. Hence, a method for detecting cancer, by which detection can be conveniently performed using serum, urine, or the like without imposing physical or economic burdens on cancer patients, is now required.

As a cancer diagnostic method using blood or urine, a method for measuring a tumor product such as a tumor marker has recently become popular. The term "tumor product" refers to a tumor-associated antigen, an enzyme, a specific protein, a metabolite, a tumor gene, a tumor gene product, a tumor suppressor gene, and the like. Carcinoembryonic antigen CEA, glycoprotein CA19-9, CA125, prostate-specific antigen PSA, calcitonin, which are peptide hormones produced in the thyroid and the like are used as tumor markers for diagnosis of some cancer types. However, tumor markers useful for cancer diagnosis are absent for many cancer types. Also, most currently known tumor markers are present in only trace amounts (on roughly a pg/mL order) in body fluids. Therefore, highly sensitive measurement methods or special techniques are required for detecting such tumor markers. Under the current circumstances, it is expected that provision of a new cancer testing means capable of detecting various types of cancer with high sensitivity involving a convenient procedure creates diagnostic applications for various types of cancer.

Also, such cancer testing means is very useful if it is capable of not only detecting cancer but also diagnosing cancer having developed in a location invisible to the naked eye, the extent of cancer, the malignancy or postoperative course of cancer, recurrence, metastasis, and the like.

Specifically, if diagnosis of cancer that has developed in a location invisible to the naked eye becomes possible, such cancer testing means would be useful for early detection of cancer within a location such as an intraperitoneal part that is difficult to recognize. Also, a tumor that does not have a grossly visible size such as cancer that is undetectable even by ultrasonography, CT (computer tomography), or MRI (nuclear magnetic resonance imaging) can be detected.

Additionally, the extent of cancer is classified based on the degree to which a tumor spreads at the primary site and the presence or the absence of metastasis to regional lymph nodes or distant organs. In general, there are 5 disease stages (each referred to as "stage"), and higher stage numbers indicate more advanced stages of the disease. Strictly, the definition of stage differs depends on organs. However, for example, cancer at stage 0 is cancer that remains intraepithelial and cancer at stage IV is cancer that has metastasized to a distant location. If such extent of cancer is found, decisions about appropriate treatment courses as well as diagnosis of the therapeutic effects of an anticancer agent become possible. As specific examples of decisions about treatment courses, in the case of prostate cancer and the like, there is a type requiring no treatment because it has very low malignancy and will almost never progress. In contrast, there is a type requiring treatment because it is progressive and metastasizes to bone or the like and causes patients to die painfully. Therapies such as hormone therapy and extirpative surgery are each associated with an adverse reaction. Thus, therapies should be appropriately determined and decided upon. Also, if evaluation concerning the selection of an anticancer agent can be appropriately made or if timing or the like for the termination of administration of an anticancer agent can be appropriately determined, physical and economical burdens on patients can also be reduced. Therefore, it is important to be able to diagnose the extent of cancer.

One of the characteristics of cancer cells is that they undergo blastogenesis; that is, dedifferentiation. Except for some cancer types, poorly differentiated or undifferentiated cancer cells with a low degree of differentiation rapidly grow after metastasis and result in poor prognosis after therapy. Such cancer is said to have high malignancy. Conversely, highly differentiated cancer cells with a high degree of differentiation retain the structural and functional characteristics of affected organs. Such cancer can be said to have relatively low malignancy. If the malignancy of cancer can be determined, the following measures can be taken. Even if the tumor is small, a wide surgical margin can be secured upon tumor removal, when the malignancy is high. Moreover, follow-up is possible while paying attention to a wide range of peripheral tissue.

If diagnosis of postoperative courses including recurrence and metastasis is possible, diagnosis of whether or not a tumor can be completely removed by surgery becomes possible. Incomplete tumor removal likely results in recurrence. Hence, such diagnosis can provide criteria for determining to more carefully perform follow-up at short intervals or to perform early reoperation if necessary. Also, if recurrence takes place, there is a high possibility of early detection. Detection is often delayed when distant metastasis takes place. However, if diagnosis of metastasis becomes possible, it becomes possible to provide criteria by which the range of testing can be broadened to include areas other than the site of removal and the periphery thereof.

It is known that dogs grow old 7 times faster than humans. Recently, companion animals are being raised as family members and often have lifestyle habits similar to those of their owners. Therefore, it is predictable that an owner's risk of developing cancer would be high when his or her companion animal develops cancer. If convenient and precise cancer diagnosis becomes possible for companion animals, it would be expected to provide clues for preventing cancer of owners.

Currently, the number of domestic dogs in Japan is said to be about 6,700,000, and the same figure for the U.S. is said to be about 17,640,000. Quintuple, septuple, and octuple combined vaccines and the like have become prevalent, in addition to rabies shots, and thereby highly lethal infectious diseases have decreased, such as canine parvovirus infection, canine distemper virus infection, canine parainfluenza (kennel cough), canine adenovirus-2 infection (kennel cough), infectious canine hepatitis, canine coronavirus infection, and leptospirosis. Therefore, the average life span of dogs has increased. Elderly dogs, which are seven years old or older, account for 35.5% of all domestic dogs. Causes of death of domestic dogs are also similar to those of humans, such as cancer, hypertension, and cardiac disease, which are on the rise. In the U.S., about 4,000,000 dogs are diagnosed with cancer annually. Also in Japan, it is said that about 1,600,000 dogs are potentially affected with tumors.

However, convenient cancer diagnostic agents for animals have been absent. Furthermore, in animal medical care, testing methods that involve photographing or filming using X-rays, CT scans, MRI scans, or the like have not been prevalent. After palpation, a simple blood test, and testing using X-ray photography are performed, diagnosis currently depends significantly on the experience of veterinarians. Testing methods using serum have been partially begun, but the methods use human tumor markers since no canine tumor marker has been discovered.

Precise cancer diagnosis requires abdominal surgery that imposes significant physical burdens on dogs and cost burdens on owners. If cancer diagnosis can be conveniently made for companion animals such as dogs and cats, it would lead to early detection or precise diagnosis of cancer and would be expected to be useful for cancer therapy for companion animals. Also, if such convenient cancer diagnosis using serum becomes possible, it would be expected not only to enable cancer diagnosis but also to significantly contribute to periodic health examinations, preoperative diagnosis, and decisions about therapeutic strategy.

Health examination for companion animals, unlike the case of humans, is not prevalent. Hence, detection of cancer often occurs too late, such that an owner finds out the disease and then comes to a hospital only after the tumor has become large in many cases. If such tumor that has increased in size is malignant, it often results in treatment that is too late, even when surgical therapy such as surgery or medication using an anticancer agent or the like is performed. Hence, when a veterinarian determines that the tumor is malignant, anticancer agent treatment is generally performed without surgery. If surgery is performed, measures during surgery, such as determination of the size of margin to be secured, determination of the amount of blood required during surgery, and measures against cell scattering should also be strictly taken. It is desired that anticancer agent treatment is initiated immediately after surgery and that follow-up is performed at short intervals. Incorporation of the above cancer diagnosis into dog health checkups that are recently increasingly prevalent and are referred to as complete medical checkups for dogs is expected to lead to early cancer detection.

On the other hand, in the case of a benign tumor, surgery can be advised even if a tumor is large. After surgery, only resected areas need care without requiring any expensive anticancer agent treatment and without any need for apprehensions concerning follow-ups.

Under the current situation, provision of a convenient means for detecting cancer with high sensitivity, which is applicable to cancer diagnosis for animals, enables precise and efficient treatment and results in a number of advantages for both owners and veterinarians.

Cytoplasmic- and proliferation-associated protein 1 (CAPRIN-1) is an intracellular protein that is expressed when normal cells in resting phase are activated or undergo cell division. CAPRIN-1 is also known to be involved in mRNA transport through intracellular formation of intracellular stress grains with RNA and translation control, for example. Meanwhile, CAPRIN-1 has many different names. Examples of such names include GPI-anchored membrane protein 1 and membrane component surface marker 1 protein (M11S1), as if the protein has been known to be a membrane protein. These different names are derived from a report (J Biol Chem. 270: 20717-20723 (1995)) that the gene sequence of CAPRIN-1 originally has a GPI-binding region and CAPRIN-1 is a membrane protein expressed in large bowel-derived cell lines. It has been later reported that: the CAPRIN-1 gene sequence in this report is an error; frame shift takes place by deletion of 1 nucleotide from the CAPRIN-1 gene sequence currently registered with GenBank or the like, so that 80 amino acids are deleted from the C terminus and the resulting artifact (74 amino acids) corresponds to the GPI binding portion of the previous report; and an error is also present on the 5' side of the gene sequence and deletion of 53 amino acids from the N terminus has been proven (J Immunol. 172: 2389-2400 (2004)). Also, it has been reported that a protein encoded by the CAPRIN-1 gene sequence currently registered with GenBank or the like is not a cell membrane protein (J Immunol. 172: 2389-2400 (2004)).

In addition, based on the report of J Biol Chem. 270: 20717-20723 (1995) that CAPRIN-1 is a cell membrane protein, US2008/0075722 and WO2005/100998 disclose that CAPRIN-1 under the name of M11S1 can be a target for cancer therapy as a cell membrane protein (not mentioned in the Examples). However, as reported in J Immunol. 172: 2389-2400 (2004), it has been accepted from the time of filing of US2008/0075722 and WO2005/100998 up to now that CAPRIN-1 is not expressed on cell surfaces. It is obvious that the content of US2008/0075722 and WO2005/100998 based only on misinformation to the effect that CAPRIN-1 is a cell membrane protein should not be understood as technical commonsense of persons skilled in the art. Moreover, it has never been reported that CAPRIN-1 is expressed at higher levels in breast cancer cells or the like than in normal cells.

SUMMARY OF THE INVENTION

Problem to be Resolved by the Invention

An object of the present invention is to provide a means for detecting cancer that is useful for cancer diagnosis.

Means for Resolving the Problem

As a result of intensive studies, the present inventors have obtained cDNA encoding a protein that binds to an antibody existing in cancer-bearing living organism-derived serum by a SEREX method using a canine testis-derived cDNA library and the serum of a cancer-bearing dog, and thus they have prepared canine CAPRIN-1 proteins having the amino acid sequences shown in SEQ ID NOS: 6, 8, 10, 12, and 14 based on the cDNA. Also, the present inventors have prepared human CAPRIN-1 proteins having the amino acid sequences shown in SEQ ID NOS: 2 and 4 based on human genes homologous to the obtained genes. The present inventors have further discovered that: genes encoding these proteins are specifically expressed in canine and human testes and malignant cancer cells (see Example 1 described later); recombinant polypeptides prepared based on the amino acid sequences of these proteins specifically react only with sera from cancer-bearing living organisms; and CAPRIN-1 can be specifically detected from a cancer-bearing living organism using antibodies prepared using the recombinant polypeptides. Thus, the present inventors have completed that present invention.

Specifically, the present invention provides a method for detecting cancer comprising measuring CAPRIN-1 expression, which is performed for samples separated from living organisms. Also, the present invention provides a reagent for detecting cancer comprising an antibody that is induced in vivo against CAPRIN-1 and a polypeptide that undergoes an antigen-antibody reaction. Furthermore, the present invention provides a reagent for detecting cancer comprising an antibody that undergoes an antigen-antibody reaction with CAPRIN-1 or an antigen-binding fragment thereof. Furthermore, the present invention provides a reagent for detecting cancer comprising a polynucleotide that specifically hybridizes to a partial sequence of 15 or more nucleotides, preferably 20 to 25 or more nucleotides, and more preferably 30 or more nucleotides in the nucleotide sequence shown in SEQ ID NO: 1, 3, 5, 7, 9, 11, 13, or the like in the Sequence Listing.

Specifically, the present invention has the following characteristics.

(1) A method for detecting a cancer, comprising measuring the expression of a polypeptide having a reactivity of binding via an antigen-antibody reaction to an antibody against a CAPRIN-1 protein having any one of the amino acid sequences shown in the even-numbered SEQ ID NOS: 2-30 in the Sequence Listing, in a sample separated from a living organism.

(2) The method according to (1) above, wherein the polypeptide to be measured is a CAPRIN-1 protein having any one of the amino acid sequences shown in the even-numbered SEQ ID NOS: 2-30 (i.e., SEQ ID NOS: 2, 4, 6, 8, . . . 30) or a polypeptide having 85% or more sequence identity with the CAPRIN-1 protein.

(3) The method according to (1) or (2) above, wherein the living organism is a human, a dog, or a cat.

(4) The method according to (3) above, wherein the living organism is a dog and the polypeptide to be measured has an amino acid sequence shown in any one of the even-numbered SEQ ID NOS: 2-30.

(5) The method according to (4) above, wherein the living organism is a dog and the polypeptide to be measured has the amino acid sequence shown in SEQ ID NO: 6, 8, 10, 12, or 14.

(6) The method according to (3) above, wherein the living organism is a human and the polypeptide to be measured has the amino acid sequence shown in SEQ ID NO: 2 or 4.

(7) The method according to any one of (1) to (6) above, wherein the expression of the polypeptide is measured by immunoassay of an antibody that can be contained in the sample and is induced in viva against the polypeptide to be measured.

(8) The method according to any one of (1) to (7) above, wherein the sample is serum, blood plasma, ascite, or pleural effusion.

(9) The method according to any one of (1) to (6) above, wherein the expression of the polypeptide is measured by measuring mRNA encoding the polypeptide, which is contained in the sample.

(10) The method according to (9) above, comprising examining the existing amount of the mRNA in the sample using a polynucleotide that specifically hybridizes to a partial sequence of 15 or more nucleotides, preferably 20 to 25 or more nucleotides, and more preferably 30 or more nucleotides in the nucleotide sequence of the above mRNA.

(11) The method according to (10) above, wherein the above living organism is a dog and the above polynucleotide is a polynucleotide specifically hybridizing to a partial sequence of 15 or more nucleotides, preferably 20 to 25 or more nucleotides, and more preferably 30 or more nucleotides in the nucleotide sequence shown in SEQ ID NO: 5, 7, 9, 11, or 13.

(12) The method according to (10) above, wherein the above living organism is a human and the above polynucleotide is a polynucleotide specifically hybridizing to a partial sequence of 15 or more nucleotides, preferably 20 to 25 or more nucleotides, and more preferably 30 or more nucleotides in the nucleotide sequence shown in SEQ ID NO: 1 or 3.

(13) The method according to any one of (9) to (12) above, wherein the above sample is a tissue or a cell.

(14) The method according to any one of (1) to (13) above, wherein the cancer is at least one type of cancer selected from the group consisting of brain tumor, squamous cell carcinoma of the head, neck, lung, uterus, or esophagus, melanoma, adenocarcinoma of the lung or uterus, renal cancer, malignant mixed tumor, hepatocellular carcinoma, basal cell carcinoma, acanthoma-like gingival tumor, tumor of the oral cavity, perianal adenocarcinoma, anal sac tumor, anal sac apocrine adenocarcinoma, sertoli cell carcinoma, cancer of vaginal vestibule, sebaceous adenocarcinoma, sebaceous epithelioma, sebaceous adenoma, sweat gland carcinoma, intranasal adenocarcinoma, nasal adenocarcinoma, thyroid cancer, large-bowel cancer, bronchial adenocarcinoma, adenocarcinoma, ductal carcinoma, breast adenocarcinoma, composite type breast adenocarcinoma, malignant mammary mixed tumor, intraductal papillary adenocarcinoma, fibrosarcoma, hemangiopericytoma, osteosarcoma, chondrosarcoma, soft tissue sarcoma, histiocytic sarcoma, myxosarcoma, undifferentiated sarcoma, lung cancer, mastocytoma, cutaneous leiomyoma, intraperitoneal leiomyoma, leiomyoma, chronic lymphocytic leukemia, lymphoma, gastrointestinal lymphoma, digestive lymphoma, small-cell-to-medium-cell lymphoma, adrenomedullary tumor, granulosa cell tumor, and pheochromocytoma.

(15) The method according to any one of (1) to (14) above, comprising further detecting the malignancy of cancer based on the fact that the malignancy of a cancer is high when the expression level of the above polypeptide is higher than that of a control.

(16) The method according to any one of (1) to (15) above, comprising further detecting the progression of cancer on the basis of the indicator that the extent of cancer is advanced when the expression level of the above polypeptide is higher than that of a control.

(17) A reagent for detecting a cancer, comprising a polypeptide that has a reactivity of binding via an antigen-antibody reaction to an antibody that is induced in vivo against a CAPRIN-1 protein having any one of the amino acid sequences shown in the even-numbered SEQ ID NOS: 2-30 in the Sequence Listing.

(18) A reagent for detecting a cancer, comprising an antibody or an antigen-binding fragment thereof that undergoes an antigen-antibody reaction with a polypeptide, wherein the polypeptide has a reactivity of binding via an antigen-antibody reaction to an antibody against a CAPRIN-1 protein having any one of the amino acid sequences shown in the even-numbered SEQ ID NOS: 2-30 in the Sequence Listing and is produced in vivo (or in a living body).

(19) The reagent for detecting cancer according to (18), wherein the antibody or antigen-binding fragment thereof that undergoes an antigen-antibody reaction with the polypeptide is an antibody or antigen-binding fragment thereof that binds to the surface of a cancer cell.

(20) The reagent for detecting cancer according to (18) or (19), wherein the antibody or antigen-binding fragment thereof that undergoes an antigen-antibody reaction with the polypeptide has an immunological reactivity with:

a polypeptide comprising an amino acid sequence of 7 or more continuous amino acid residues within the region of amino acid residue Nos. 50-98 or amino acid residue Nos. 233-305 in any one of the amino acid sequences shown in the even-numbered SEQ IDS NO: 2-30 excluding SEQ ID NO: 6 and SEQ ID NO: 18 or a polypeptide comprising the polypeptide as a partial sequence.

(21) The reagent for detecting a cancer according to any one of (18) to (20), wherein the antibody or antigen-binding fragment thereof that undergoes an antigen-antibody reaction with the polypeptide is an antibody or antigen-binding fragment thereof which binds to SEQ ID NO: 43, a monoclonal antibody or antigen-binding fragment thereof having the amino acid sequences of SEQ ID NOS: 44 and 45, a monoclonal antibody or antigen-binding fragment thereof having the amino acid sequences of SEQ ID NOS: 44 and 46, a monoclonal antibody or antigen-binding fragment thereof having the amino acid sequences of SEQ ID NOS: 44 and 47, a monoclonal antibody or antigen-binding fragment thereof having the amino acid sequences of SEQ ID NOS: 44 and 48, a monoclonal antibody an antigen-binding fragment thereof having the amino acid sequences of SEQ ID NOS: 49 and 50, a monoclonal antibody or antigen-binding fragment thereof having the amino acid sequences of SEQ ID NOS: 51 and 52, a monoclonal antibody or antigen-binding fragment thereof having the amino acid sequences of SEQ ID NOS: 53 and 54, a monoclonal antibody or antigen-binding fragment thereof having the amino acid sequences of SEQ ID NOS: 55 and 56, a monoclonal antibody or antigen-binding fragment thereof having the amino acid sequences of SEQ ID NOS: 57 and 58, or a monoclonal antibody or antigen-binding fragment thereof having the amino acid sequences of SEQ ID NOS: 59 and 60.

(22) A reagent for detecting a cancer, comprising a polynucleotide that specifically hybridizes to a partial sequence of 15 or more nucleotides, preferably 20 to 25 or more nucleotides, and more preferably 30 or more nucleotides in any one of the nucleotide sequences shown in the odd-numbered SEQ ID NOS: 1-29 (i.e., SEQ ID NOS: 1, 3, 5, 7, . . . 29) in the Sequence Listing.

Advantage of the Invention

According to the present invention, a new method for detecting a cancer is provided. As specifically described in Examples given later, a recombinant polypeptide prepared based on the amino acid sequence of CAPRIN-1 (or also referred to as Caprin-1) reacts with an antibody that specifically exists in the serum of a patient with cancer. Therefore, the cancer existing in a living body can be detected by measuring the antibody in a sample by the method of the present invention. Also, the cancer existing in a living body can be detected by measuring CAPRIN-1 itself. According to the method of the present invention, small-size cancer invisible to the naked eye or cancer in a deep part in vivo can be detected. Hence, the method of the present invention is useful for early detection of cancer at the time of health examination or the like. Furthermore, recurrent cancer can be detected early by the use of the method of the present invention for the follow-up of a patient after cancer treatment. Moreover, according to the method of the present invention, the extent of cancer can also be diagnosed, such as tumor increase, infiltration to the peripheral tissue, and cancer metastasis to a lymph node and a distant organ. Also, the serum antibody level is higher in a patient with highly malignant cancer than in a patient with low-malignant cancer. According to the method of the present invention, the malignancy of cancer can also be diagnosed. Also, as described in Examples below, mRNA encoding CAPRIN-1 is specifically expressed at high levels in testes and cancer cells. Therefore, cancers can also be detected by measuring the mRNA.

BEST MODE OF CARRYING OUT THE INVENTION

Figure 1:
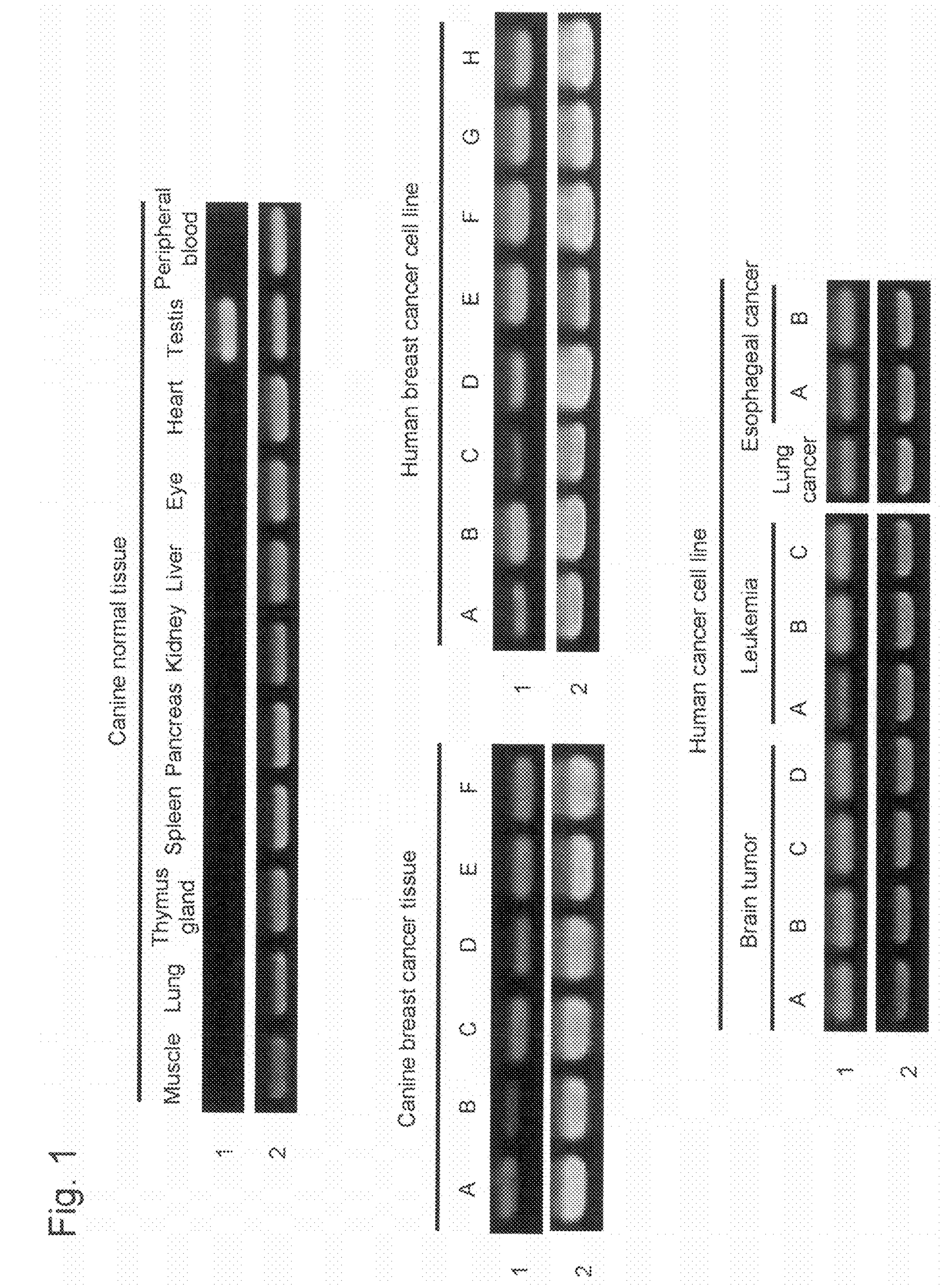
FIG. 1 shows the expression patterns of the gene encoding a CAPRIN-1 protein in normal tissues and tumor cell lines. Reference No. 1 indicates the expression patterns of the gene encoding the CAPRIN-1 protein. Reference No. 2 indicates the expression patterns of the GAPDH gene.

According to the method of the present invention, CAPRIN-1 expression is measured using a sample separated from a living organism. Examples of a method for measuring CAPRIN-1 expression include a method ($1^{st}$ method) that involves immunoassay for an antibody against CAPRIN-1 contained in a sample, a method ($2^{nd}$ method) that involves immunoassay for CAPRIN-1 itself contained in a sample, and a method ($3^{rd}$ method) that involves measurement of mRNA encoding CAPRIN-1 contained in a sample. In the method of the present invention, CAPRIN-1 expression may be measured by any of these methods. In the present invention, the term "measurement" refers to any of detection, qualitative determination, quantitative determination, and semi-quantitative determination.

The amino acid sequence shown in SEQ ID NO: 6, 8, 10, 12, or 14 is the amino acid sequence of canine CAPRIN-1. Canine CAPRIN-1 having the amino acid sequence was identified as a polypeptide binding to an antibody specifically existing in the cancer-bearing dog-derived serum by the SEREX method using a canine testis-derived cDNA library and the serum of a cancer-bearing dog (see Example 1). Specifically, an antibody against CAPRIN-1 having the amino acid sequence shown in SEQ ID NO: 6, 8, 10, 12, or 14 is specifically induced in vivo in a cancer-bearing dog. Therefore, canine cancer can be detected by measuring the above antibody against CAPRIN-1 having the amino acid sequence shown in SEQ ID NO: 6, 8, 10, 12, or 14 using the above $1^{st}$ method (see Examples 3 and 4). Canine cancer can also be detected by measuring CAPRIN-1 itself as an antigen shown in SEQ ID NO: 6, 8, 10, 12, or 14 using the above $2^{nd}$ method (see Examples 5 and 6). Also, canine cancer can be detected, as described in the following Examples, by measuring mRNA encoding CAPRIN-1 since the mRNA is expressed at significantly high levels in testes and cancer cells (see Example 1).

The term "having an amino acid sequence" as used herein refers to amino acid residues being aligned in the relevant order. Therefore, for example, the expression "polypeptide having the amino acid sequence shown in SEQ ID NO: 2" refers to a polypeptide having 709 amino acid residues, which consists of the amino acid sequence of Met Pro Ser Ala . . . (abbreviated) . . . Gln Gln Val Asn shown in SEQ ID NO: 2. Also, for example, the expression "polypeptide having the amino acid sequence shown in SEQ ID NO: 2" may also be abbreviated as "the polypeptide of SEQ ID NO: 2." The same applies to the expression "having a/the nucleotide sequence." In this case, the term "having" may be substituted with the expressions "consisting of."

Also, the term "polypeptide" as used herein refers to a molecule that is formed via peptide bonding of a plurality of amino acids. Examples of such molecule include not only polypeptide molecules with a large number of constituent amino acids, but also low-molecular-weight molecules (oligopeptides) with small number of amino acids and full-length proteins. The present invention further encompasses full-length CAPRIN-1 proteins each having an amino acid sequence shown in an even-numbered sequence ID from among SEQ ID NOS: 2-30.

In the method of the present invention, not only canine CAPRIN-1 of SEQ ID NO: 6, 8, 10, 12, or 14, but also CAPRIN-1 of other mammals (hereinafter, may also be referred to as "homolog" for canine CAPRIN-1. When simply referred to as "CAPRIN-1," CAPRIN-1 from not only a dog but also from another mammal is also encompassed herein) are also subjected to measurement. As specifically described in the following Examples, mRNA encoding human CAPRIN-1 is significantly expressed at a high level in human testis and cancer cells, as in the case of canine CAPRIN-1 of SEQ ID NO: 6, 8, 10, 12 or 14. However, no antibody against the human CAPRIN-1 is detected in a healthy human body. Also, an antibody against feline CAPRIN-1 is not detected in a healthy cat body, but is detected in a cancer-bearing cat alone. Therefore, cancer of a mammal other than a dog can be detected by measuring CAPRIN-1 expression in the mammal. Examples of CAPRIN-1 of mammals other than dogs, which are measurement subjects in the method of the present invention, include, but are not limited to, human CAPRIN-1 and feline CAPRIN-1. A nucleotide sequence encoding human CAPRIN-1 and the amino acid sequence thereof are as separately shown in SEQ ID NO: 1 and 3, and 2 and 4, respectively, in the Sequence Listing. Sequence identity with canine CAPRIN-1 is 94% in terms of nucleotide sequence and is 98% in terms of amino acid sequence. Even dogs and humans which are genetically distant mammals share as very high as 98% sequence identity in terms of the amino acid sequence of CAPRIN-1. Therefore, it is thought that a dog and a mammal other than a human; that is, canine CAPRIN-1 and homolog thereof share sequence identity as high as about 85% or more. Therefore, CAPRIN-1, the expression of which is measured in the method of the present invention, has preferably 85% or more and more preferably 95% or more sequence identity with the amino acid sequence of canine CAPRIN-1 shown in SEQ ID NO: 6, 8, 10, 12, or 14. However, such examples are not particularly limited thereto.

In the 1$^{st}$ method above, the above antibody that can be present in a sample can be easily measured by immunoassay using an antigenic substance that undergoes an antigen-antibody reaction with the antibody. Immunoassay itself is a known conventional method as specifically described below. As an antigenic substance for immunoassay, the canine CAPRIN-1 of SEQ ID NO: 6, 8, 10, 12, or 14 that causes the induction of the antibody within a cancer-bearing dog body can be used. Furthermore, an antibody has cross-reactivity. Thus, even a molecule other than an antigenic substance actually having served as an immunogen can bind to an antibody induced against the immunogen via an antigen-antibody reaction, as long as a structure analogous to the epitope of the immunogen is present on the molecule. In particular, a protein from a mammal and homolog thereof from another mammal share high amino acid sequence identity and often have epitope structures analogous to each other. As specifically described in the following Examples, the canine CAPRIN-1 of SEQ ID NO: 6, 8, 10, 12, or 14 undergoes an antigen-antibody reaction not only with an antibody induced against the canine CAPRIN-1 within a cancer-bearing dog body, but also with an antibody induced against feline CAPRIN-1 within a cancer-bearing cat body. Moreover, human CAPRIN-1 undergoes an antigen-antibody reaction with the above antibody induced within cancer-bearing dog or cancer-bearing cat bodies. Accordingly, in the 1$^{st}$ method of the present invention, CAPRIN-1 from any mammal can be used as an antigen for immunoassay.

In general, when an antigenic substance is a protein or the like having a complicated structure and high molecular weight, a plurality of sites having different structures are present on the molecule. Therefore, a plurality of types of antibody capable of recognizing and binding to different sites of such antigenic substances are produced in vivo. Specifically, an antibody that is produced in vivo against an antigenic substance such as protein is a polyclonal antibody that is a mixture of a plurality of types of antibody. An antibody discovered by the present inventors is also a polyclonal antibody. It is specifically present in cancer-bearing living organism-derived serum and specifically binds to a recombinant CAPRIN-1 protein via an antigen-antibody reaction. The term "polyclonal antibody" used in the present invention refers to an antibody that exists in serum from a living organism containing an antigenic substance therein and is induced in vivo against the antigenic substance.

In Examples described later, polypeptides of SEQ ID NO: 6 and SEQ ID NO: 8 (canine CAPRIN-1) and the polypeptide of SEQ ID NO: 2 (human CAPRIN-1) were prepared as antigens for immunoassay of specific antibodies in the cancer-bearing living animals. Then reactivity between these polypeptides and the above antibody in serum from a cancer-bearing living organism was confirmed. However, the above antibody is a polyclonal antibody, so that it naturally binds to a polypeptide consisting of the homolog of SEQ ID NO: 6, 8, or 2. Even in the case of a fragment of said polypeptides, it can bind to the above antibody contained in serum from a cancer-bearing living organism, since the polyclonal antibody can contain an antibody capable of recognizing the structure of the relevant fragment. That is, either a polypeptide (that is, full-length CAPRIN-1 protein) of the homolog of SEQ ID NO: 6, 8, or 2 or a fragment thereof can be similarly used for measurement of the above polyclonal antibody contained specifically in serum of a cancer-bearing living organism and is useful for cancer detection. Therefore, examples of a polypeptide to be used as an antigen for immunoassay in the 1$^{st}$ method of the present invention include, not only a polypeptide that consists of the full-length region of CAPRIN-1 (e.g., SEQ ID NO: 6, 8, or 2), but also a polypeptide fragment that consists of continuous 7 or more, preferably continuous 8 or more, 9 or more, or 10 or more amino acids in the amino acid sequence of CAPRIN-1 and undergoes an antigen-antibody reaction with a polyclonal antibody against CAPRIN-1 (hereinafter, may be conveniently referred to as "a specifically reactive partial polypeptide"). It is known in the art that a polypeptide of about 7 or more amino acid residues exerts antigenicity. However, if the number of amino acid residues constituting a polypeptide is too low, such polypeptide highly likely cross-reacts with antibodies, which exists in the sample, against proteins other than CAPRIN-1. Accordingly, in view of increasing the accuracy of immunoassay, the desirable number of amino acid residues of a polypeptide fragment may be preferably 30 or more or 50 or more, further preferably 100 or more or 150 or more, further preferably 300 or more, even more preferably 600 or more, and further preferably 1000 or more and 1500 or more.

Specific preferable examples of the polypeptides to be used as antigens are the polypeptides of the even-numbered SEQ ID NOS: 2-30 or fragments thereof.

Nucleotide sequences of polynucleotides encoding proteins consisting of the amino acid sequences of the even-numbered SEQ ID NOS: 2-30 (that is, SEQ ID NOS: 2, 4, 6 . . . 28, 30) are shown in the odd-numbered SEQ ID NOS: 1-29 (that is, SEQ ID NOS: 1, 3, 5 . . . 27, 29).

In general, it is broadly known by persons skilled in the art concerning protein antigens such that even when few amino acid residues have been substituted, deleted, added, or inserted in the amino acid sequence of the protein, the resultant may retain antigenicity almost equivalent to that of the original protein. Therefore, a polypeptide: having a sequence that has a substitution, a deletion, and/or an insertion of a few (preferably one or several) amino acid residues with respect to the amino acid sequence of CAPRIN-1 and has 80% or more, 85% or more, preferably 90% or more, more preferably 95% or more, and further preferably 98% or more sequence identity with the original sequence; and specifically binding to a polyclonal antibody against CAPRIN-1 via an antigen-antibody reaction (hereinafter, may be conveniently referred to as "specifically reactive modified polypeptide") can be used for cancer detection in a manner similar to that for the above polypeptides. Preferably, the specifically reactive modified polypeptide has an amino acid sequence that has a substitution, a deletion, an addition, and/or an insertion of one or several amino acid residues with respect to the amino acid sequence of CAPRIN-1. The term "several" as used herein refers to an integer of 2-10, preferably an integer of 2-6, and further preferably an integer of 2-4.

The term "sequence identity (of amino acid sequences)" as used herein is obtained by aligning two amino acid sequences to be compared so that amino acid residues match as many as possible, subtracting the number of amino acid residues that have matched from the total number of amino acid residues, and then expressing the result in percentage form. Upon the above alignment, if necessary, gaps are appropriately inserted into one of or both sequences to be compared. Such sequence alignment can be performed using a known program such as BLAST, FASTA, or CLUSTAL W (Karlin and Altschul, Proc. Natl. Acad. Sci. U.S.A., 87: 2264-2268, 1993; Altschul et al., Nucleic Acids Res., 25: 3389-3402, 1997).

Twenty types of amino acid constituting natural proteins can be grouped into neutral amino acids having side chains with low polarity (Gly, Ile, Val, Leu, Ala, Met, and Pro), neutral amino acids having hydrophilic side chains (Asn, Gln, Thr, Ser, Tyr, and Cys), acidic amino acids (Asp and Glu), basic amino acids (Arg, Lys, and His), and aromatic amino acids (Phe, Tyr, Trp, and His) in which the members of each group have properties analogous to each other. It is known that substitution among these amino acids (that is, conservative substitution) rarely alters the properties of the resulting polypeptide. Therefore, when amino acid residues of CAPRIN-1 are substituted, substitution is performed between members of the same group so that a possibility of maintaining binding with the corresponding antibody becomes higher. However, in the present invention, the above variant may involve non-conservative substitution, as long as immune-inducing activity equivalent to or almost equivalent to that of a non-variant is imparted.

A polypeptide (hereinafter, may conveniently be referred to as "specifically reactive addition polypeptide") that contains as a partial sequence the above polypeptide to be used in the present invention (that is, prepared by addition of another (poly)peptide to one end or both ends of a polypeptide to be used in the present invention) and specifically binds to a polyclonal antibody against CAPRIN-1 via an antigen-antibody reaction can also be used for cancer detection in a manner similar to that for the above polypeptides.

The above polypeptides to be used in the present invention can be synthesized according to a chemical synthesis method such as an Fmoc method (fluorenylmethyloxycarbonyl method) and a tBoc method (t-butyloxy-carbonyl method) (Ed., The Japanese Biochemical Society, Seikagaku Jikken Koza (Biochemical Experimental Lecture Series) 1, Protein Chemistry IV, Chemical Modification and Peptide Synthesis, TOKYO KAGAKU DOZIN CO., LTD (Japan), 1981). Also, the polypeptides can also be synthesized by a conventional method using various commercially available peptide synthesizers. Alternatively, the polypeptides can be easily prepared using known genetic engineering techniques (Sambrook et al., Molecular Cloning, 2nd Edition, Current Protocols in Molecular Biology (1989), Cold Spring Harbor Laboratory Press, Ausubel et al., Short Protocols in Molecular Biology, 3rd Edition, A Compendium of Methods from Current Protocols in Molecular Biology (1995), John Wiley & Sons, and the like). For example, from RNA extracted from a tissue expressing a gene encoding the human CAPRIN-1 of SEQ ID NO: 2 or a homolog thereof, cDNA of the gene is prepared by RT-PCR. The full-length sequence or a desired partial sequence of the cDNA is incorporated into an expression vector and then the vector is introduced into host cells, so that a polypeptide of interest can be obtained. The nucleotide sequences of cDNAs encoding canine CAPRIN-1 of SEQ ID NOS: 6, 8, 10, 12, and 14 are shown in SEQ ID NOS: 5, 7, 9, 11, and 13, respectively. The human factors homolog thereof; that is, the nucleotide sequences of cDNAs encoding human CAPRIN-1 of SEQ ID NOS: 2 and 4 are shown in SEQ ID NOS: 1 and 3, respectively. Hence, primers to be used for RT-PCR can be easily designed in reference to these nucleotide sequences. Also, as described later, a gene encoding CAPRIN-1 of a non-human mammal can be amplified using primers designed in reference to the nucleotide sequences of the odd-numbered SEQ ID NOS: 1-29. For example, cDNA encoding feline CAPRIN-1 can be easily prepared by techniques similar to the above techniques. RNA extraction, RT-PCR, cDNA incorporation into a vector, and introduction of a vector into host cells can be performed by known methods as described below, for example. Also, vectors and host cells to be used herein are also known and various vectors and host cells are commercially available.

The above host cells may be any cells, as long as they can express the above polypeptides. Examples of prokaryotic host cells include *Escherichia coli* and the like. Examples of eukaryotic host cells include mammalian cultured cells such as monkey kidney cells (COS1), Chinese hamster ovary cells (CHO), the human embryonic kidney cell line (HEK293), and the mouse embryonic skin cell line (NIH3T3), budding yeast, fission yeast, silkworm cells, and Xenopusoocytes.

When prokaryotic cells are used as host cells, an expression vector having a replication origin in prokaryotic cells, a promoter, a ribosome-binding site, a multi-cloning site, a terminator, a drug-resistance gene, an auxotrophic complementary gene, and the like are used. As expression vectors for *Escherichia coli*, pUC vectors, pBluescriptII, pET expression systems, pGEX expression systems, and the like can be exemplified. A DNA encoding the above polypeptide is incorporated into such an expression vector, prokaryotic host cells are transformed with the vector, and then the thus obtained transformant is cultured, so that the polypeptide encoded by the DNA can be expressed in the prokaryotic host cells. At this time, the polypeptide can also be expressed as a fusion protein with another protein. A DNA encoding the above polypeptide can be obtained by preparing a cDNA by RT-PCR as described above, for example. Moreover, such DNA encoding the above polypeptide can be also synthesized by a conventional method using a commercially available nucleic acid synthesizer as described below. The nucleotide sequences of cDNAs of the genes encoding CAPRIN-1 of SEQ ID NOS: 2 and 4 are shown in SEQ ID NOS: 1 and 3, respectively, in the Sequence Listing.

When eukaryotic cells are used as host cells, expression vectors for eukaryotic cells having a promoter, a splicing region, a poly(A) additional site, and the like are used. Examples of such expression vectors include pKA1, pCDM8, pSVK3, pMSG, pSVL, pBK-CMV, pBK-RSV, EBV vector, pRS, pcDNA3, and pYES2. Similarly to the above, a DNA encoding a polypeptide to be used in the present invention is incorporated into such an expression vector, eukaryotic host cells are transformed with the vector, and then the thus obtained transformant is cultured, so that the polypeptide encoded by the above DNA can be expressed in eukaryotic host cells. When pIND/V5-His, pFLAG-CMV-2, pEGFP-N1, pEGFP-Cl, or the like is used as an expression vector, the above polypeptide can be expressed as a fusion protein with various tags, such as a His tag (e.g., $(His)_6$ to $(His)_{10}$), a FLAG tag, a myc tag, a HA tag, and GFP.

For introduction of an expression vector into a host cell, known methods can be employed such as electroporation, a calcium phosphate method, a liposome method, a DEAE dextran method, microinjection, viral infection, lipofection, and binding with a cell-membrane-permeable peptide.

Isolation and purification of a polypeptide of interest from host cells can be performed using known isolation techniques in combination. Examples of such known techniques include treatment using a denaturing agent such as urea or a surfactant, ultrasonication, enzymatic digestion, salting-out, solvent fractionation and precipitation, dialysis, centrifugation, ultrafiltration, gel filtration, SDS-PAGE, isoelectric focusing, ion exchange chromatography, hydrophobic chromatography, affinity chromatography, and reverse phase chromatography.

Polypeptides obtained by the above methods include polypeptides in the form of fusion proteins with any other proteins. An example of such a fusion protein include a fusion protein with glutathione-S-transferase (GST), a His tag, or the like. Polypeptides in the form of such fusion proteins are also examples of the above-described specifically reactive addition polypeptides and can be used for the $1^{st}$ detection method of the present invention. Furthermore, a polypeptide expressed in transformed cells may be subjected to various types of modification within cells after translation. Such polypeptide that is modified after translation can be used in the $1^{st}$ detection method of the present invention, as long as it is capable of binding to a polyclonal antibody against CAPRIN-1. Examples of such post-translation modification include the removal of N-terminal methionine, N-terminal acetylation, glycosylation, limited proteolysis by intracellular protease, myristoylation, isoprenylation, and phosphorylation.

An antibody in a sample can be easily measured by immunoassay using the above polypeptide as an antigen. Immunoassay itself is known in the art. Immunoassay is classified into a sandwich method, a competition method, an agglutination method, Western blot method, and the like based on types of reaction. Also, immunoassay is classified based on labels into radioimmunoassay, fluorescence immunoassay, enzyme immunoassay, and biotin immunoassay, for example. Immunoassay of the above antibody can be performed using any of these methods. Sandwich ELISA or the agglutination method are preferably applicable as an immunoassay technique for the above antibody in the method of the present invention, since the procedures of these methods are convenient and require no extensive apparatus and the like. But the techniques are not limited to them. When an enzyme is used as a label for an antibody, such enzyme is not particularly limited, as long as it satisfies conditions such that: the turn over number is high; it remains stable even if it is bound to an antibody, it specifically causes the color development of the substrate, and the like. Examples of enzymes that can be used for general enzyme immunoassay include peroxidase, β-galactosidase, alkaline phosphatase, glucose oxidase, acetylcholine esterase, glucose-6-phosphorylation dehydrogenase, and malic acid dehydrogenase. Also, enzyme-inhibiting substances, coenzymes, and the like can be used. Binding of these enzymes with antibodies can be performed by known methods using a cross-linking agent such as a maleimide compound. As a substrate, a known substance can be used depending on the type of an enzyme to be used. For example, when peroxidase is used as an enzyme, 3,3',5,5'-tetramethylbenzidine can be used. Also when alkaline phosphatase is used as an enzyme, para-nitrophenol or the like can be used. As a radio isotope, a radio isotope that is generally used for radioimmunoassay, such as $^{125}I$ and $^{3}H$ can be used. As a fluorescent dye, a fluorescent dye that is used for general fluorescent antibody techniques, such as fluorescence isothiocyanate (FITC) and tetramethylrhodamine isothiocyanate (TRITC) can be used.

There is no need to explain the above immunoassay techniques in the Description, since they are well-known. However, when these immunoassay techniques are briefly described, the sandwich method involves immobilizing the above polypeptide to be used as an antigen to a solid phase, reacting it with a sample such as serum, washing, reacting with an appropriate secondary antibody, washing, and then measuring the secondary antibody bound to the solid phase, for example. An unbound secondary antibody can be easily removed by immobilization of an antigen polypeptide to a solid phase. Hence, this is preferable as an embodiment of the method for detecting cancer of the present invention. As a secondary antibody, an anti-canine IgG antibody can be used if a sample is derived from a dog. A secondary antibody is labeled in advance with a labeling substance exemplified above, so that the secondary antibody binding to a solid phase can be measured. The thus measured amount of the secondary antibody corresponds to the amount of the above antibody in the serum sample. When an enzyme is used as a labeling substance, the amount of the antibody can be measured by adding a substrate that is digested to develop color by enzymatic action and then optically measuring the amount of the substrate degraded. When a radio isotope is used as a labeling substance, the amount of radiation from the radio isotope can be measured using a scintillation counter or the like.

In the $2^{nd}$ method of the present invention, CAPRIN-1 that can be contained in a sample from a living organism is measured. As described above, among cancer patients, the amount of an antibody that undergoes an antigen-antibody reaction with CAPRIN-1 of a dog, a human, or the like is significantly high. This indicates that the amount of CAPRIN-1 accumulated as an antigen is significantly high in cancer cells. Cancer can also be detected by directly measuring CAPRIN-1, as specifically described in Examples below. Therefore, cancer can be detected in vivo by measuring CAPRIN-1 itself similarly to the $1^{st}$ method above.

A polypeptide in a sample can be easily measured by well-known immunoassay techniques. Specifically, for example, an antibody or an antigen-binding fragment thereof, which undergoes an antigen-antibody reaction with CAPRIN-1, is prepared, immunoassay is performed using the antibody or its antigen-binding fragment thereof, and then CAPRIN-1 that may be present in the sample can be measured. As described above, an antibody has cross-reactivity. Hence, for example, through the use of an antibody or the antigen-binding fragment thereof, which undergoes an antigen-antibody reaction with the canine CAPRIN-1 of SEQ ID NO: 6, not only the canine CAPRIN-1 of SEQ ID NO: 6, but also its homolog in other mammals (e.g., the human CAPRIN-1 of SEQ ID NO: 2 or 4 and feline CAPRIN-1) can be measured. An immunoassay technique itself is a known conventional technique as described above.

This examination revealed that CAPRIN-1 is a cell membrane protein that is expressed on the surfaces of cancer cells. A living organism with cancer contains many kinds of proteases. Specifically, in a living organism with cancer, an extracellularly expressed portion of the CAPRIN-1 sequence is separated from the cancer cells by degradation, so that such portion exists at a level higher than an intracellularly expressed portion of the CAPRIN-1 sequence. Therefore, when an antibody against CAPRIN-1 or an antigen-binding fragment thereof to be used in this measurement, which binds to the surface of the cancer cell, is used, CAPRIN-1 can be detected at higher levels and cancer can be diagnosed with higher sensitivity. Therefore, in the present invention, antibodies binding to a portion of the CAPRIN-1 protein existing on the surfaces of cancer cells, are preferably used. An example of a partial peptide of the CAPRIN-1 protein existing on the surfaces of cancer cells, is a polypeptide comprising a sequence of continuous 7 or more amino acid residues within the region of amino acid residue Nos. (aa) 50-98 or amino acid residue Nos. (aa) 233-305 in the amino acid sequences shown in the even-numbered SEQ ID NOS: 2-30 in the Sequence Listing excluding SEQ ID NO: 6 and SEQ ID NO: 18. A specific example thereof is the amino acid sequence shown in SEQ ID NO: 43 or SEQ ID NO: 61 (in the amino acid sequence shown in SEQ ID NO: 61, a region of the amino acid sequence shown in SEQ ID NO: 62 or SEQ ID NO: 63 is preferred) or an amino acid sequence having 80% or more, preferably 85% or more, more preferably 90% or more, further preferably 95% or more sequence identity with the relevant amino acid sequence. Examples of an antibody to be used in the present invention include all antibodies binding to these peptides. Specific examples of the antibody include an antibody or antigen-binding fragment thereof which binds to SEQ ID NO: 43, a monoclonal antibody or antigen-binding fragment thereof having the amino acid sequences of SEQ ID NOS: 44 and 45, a monoclonal antibody or antigen-binding fragment thereof having the amino acid sequences of SEQ ID NOS: 44 and 46, a monoclonal antibody or antigen-binding fragment thereof having the amino acid sequences of SEQ ID NOS: 44 and 47, a monoclonal antibody or antigen-binding fragment thereof having the amino acid sequences of SEQ ID NOS: 44 and 48, a monoclonal antibody an antigen-binding fragment thereof having the amino acid sequences of SEQ ID NOS: 49 and 50, a monoclonal antibody or antigen-binding fragment thereof having the amino acid sequences of SEQ ID NOS: 51 and 52, a monoclonal antibody or antigen-binding fragment thereof having the amino acid sequences of SEQ ID NOS: 53 and 54, a monoclonal antibody or antigen-binding fragment thereof having the amino acid sequences of SEQ ID NOS: 55 and 56, a monoclonal antibody or antigen-binding fragment thereof having the amino acid sequences of SEQ ID NOS: 57 and 58, or a monoclonal antibody or antigen-binding fragment thereof having the amino acid sequences of SEQ ID NOS: 59 and 60.

The term "antigen-binding fragment" as used herein refers to an antibody fragment capable of binding to an antigen such as a Fab fragment and a $F(ab')_2$ fragment contained in an antibody molecule. An antibody to be used herein may be a polyclonal antibody or a monoclonal antibody. For immunoassay and the like, a monoclonal antibody with high reproducibility is preferable. A method for preparing a polyclonal antibody and a monoclonal antibody using a polypeptide as an immunogen is known and can be easily performed by a conventional method. For example, CAPRIN-1 is bound to a carrier protein such as keyhole limpet hemocyanin (KLH), casein, or serum albumin and then an animal is immunized with the resultant as an immunogen together with an adjuvant, and thereby an antibody against CAPRIN-1 can be induced. Antibody-producing cells such as splenocytes or lymphocytes collected from the immunized animal are fused to myeloma cells to prepare hybridomas, and then hybridomas producing an antibody that binds to CAPRIN-1 are selected and then grown, so that a monoclonal antibody, whose the corresponding antigen is CAPRIN-1, can be obtained from the cultured supernatant. The above method is a known conventional method.

In the $3^{rd}$ method of the present invention, mRNA encoding CAPRIN-1 that can be contained in a sample obtained from a living organism is measured. As specifically described in Examples below, mRNA encoding the canine CAPRIN-1 of SEQ ID NO: 6, 8, 10, 12, or 14 or human CAPRIN-1 of SEQ ID NO: 2 or 4 is expressed at a significantly high level in cancer cells. Therefore, cancer can be detected in vivo by measuring such mRNA in a sample.

mRNA in a sample can be quantitatively determined by a conventional method such as real-time detection RT-PCR using the mRNA as a template, for example. Such mRNA can generally be quantitatively determined based on staining intensity or the like in Northern blot that is a conventional method. The cDNA sequences encoding CAPRIN-1 polypeptides of the even-numbered SEQ ID NOS: 2-30 are shown in the odd-numbered SEQ ID NOS: 1-29, respectively. Hence, based on these sequences, a polynucleotide specifically hybridizing to a partial region in the nucleotide sequence shown in any of the odd-numbered SEQ ID NOS: 1-29 (hereinafter, referred to as "polynucleotide for cancer detection") is prepared and then the amount of the mRNA in a sample can be measured using the polynucleotide as a probe or a primer for a nucleic acid amplification method. As described later, if it is a polynucleotide specifically hybridizing to a partial region in the nucleotide sequence shown in any of the odd-numbered SEQ ID NOS: 1-29, mRNA encoding CAPRIN-1 in mammals other than dogs and humans can also be determined. In addition, in the present invention, a polynucleotide may be RNA or DNA.

The term "specifically hybridizing to" as used herein refers to that under general hybridization conditions, a subject hybridizes to only a target partial region, but does not substantially hybridize to the other regions.

The term "(under) general hybridization conditions" as used herein refers to conditions employed for annealing in general PCR or detection using a probe. For example, in the case of PCR using Taq polymerase, the term refers to conditions under which a reaction is performed at an appropriate annealing temperature ranging from about 54° C. to 60° C. using a general buffer such as 50 mM KCl, 10 mM Tris-HCl (pH8.3-9.0), and 1.5 mM $MgCl_2$. Also, in the case of Northern hybridization, for example, the term refers to conditions under which a reaction is performed using a general hybridization solution such as 5×SSPE, 50% formamide, 5×Denhardt's solution, and 0.1% SDS-0.5% SDS, or 0.1-5×SSC and 0.1-0.5% SDS at an appropriate hybridization temperature ranging from about 42° C. to 65° C. Furthermore, after hybridization, washing is performed with 0.1-0.2×SSC and 0.1% SDS, for example. However, appropriate annealing temperatures or hybridization temperatures are not limited to the above examples, and are determined based on Tm value for a polynucleotide for cancer detection, which is used as a primer or a probe, and the empirical rule of experimenters. Persons skilled in the art can easily determine such temperature range.

The expression "does not substantially hybridize to" as used herein refers to that a subject does not really hybridize to a target partial region or a subject hybridizes to a target partial region in a significantly low amount; that is, in a relatively negligibly-small amount, even when it hybridizes to the target partial region. An example of a polynucleotide specifically hybridizing under such conditions is a polynucleotide having sequence identity at a level or more with the nucleotide sequence of a target partial region. A specific example of such polynucleotide has 70% or more, preferably 80% or more, 85% or more, more preferably 90% or more, further preferably 93% or more, further preferably 95% or more, and further more preferably 98% or more sequence identity. Most preferably, the polynucleotide has a nucleotide sequence identical to the nucleotide sequence of a target partial region. Sequence identity is defined in the same manner as that for the sequence identity of the above amino acid sequence. Even if a terminus of a polynucleotide for cancer detection contains a region not hybridizing to a subject, in the case of a probe, it can be used for detection as long as a hybridizing region occupies as much as about a half or more of the entire probe. Also, in the case of a primer, it can be used for detection as long as a hybridizing region occupies as much as about a half or more of the entire primer and is located on the 3' terminal side, since normal annealing and extension reaction can take place. As described above, when a terminus of a polynucleotide for cancer detection contains a non-hybridizing region, sequence identity with a target nucleotide sequence is calculated focusing on only a hybridizing region without taking non-hybridizing region into consideration.

The term "partial sequence" in the present invention refers to a partial sequence in the nucleotide sequences shown in the odd-numbered SEQ ID NOS: 1-29, specifically the partial sequence having a sequence of continuous 15 or more nucleotides, preferably continuous 18 or more nucleotides, more preferably continuous 20 or more nucleotides or 25 or more nucleotides, and further preferably continuous 30, 40, or 50 or more nucleotides. The expression "the nucleotide sequence shown in SEQ ID NO: 5" as used herein refers to, in addition to the nucleotide sequence actually shown in SEQ ID NO: 5, a sequence complementary to the sequence. Therefore, for example, the expression "a polynucleotide having the nucleotide sequence shown in SEQ ID NO: 5" refers to a single-stranded polynucleotide having the nucleotide sequence actually shown in SEQ ID NO: 5, a single-stranded polynucleotide having a nucleotide sequence complementary to that shown in SEQ ID NO: 5, and a double-stranded polynucleotide comprising them. When a polynucleotide to be used in the present invention is prepared or a polynucleotide encoding a polypeptide to be used in the present invention is prepared, any one nucleotide sequence is appropriately selected and this selection can be easily performed by persons skilled in the art.

The number of nucleotides in a polynucleotide for cancer detection is preferably 18 or more nucleotides in view of ensuring specificity. When used as a probe, the size of the polynucleotide is preferably 18 or more nucleotides, is further preferably 20 or more nucleotides and the full-length or less of the coding region. When used as a primer, the size of the polynucleotide is preferably 18 or more nucleotides and 50 or less nucleotides. A preferred example of the polynucleotide for cancer detection is a polynucleotide comprising continuous 18 or more nucleotides in a nucleotide sequence shown in any of the odd-numbered SEQ ID NOS: 1-29.

It is obvious for persons skilled in the art who refer this Description that: a polynucleotide specifically hybridizing to a partial region in SEQ ID NO: 5, 7, 9, 11, or 13 is used for measurement of the amount of mRNA encoding the canine CAPRIN-1 of SEQ ID NO: 6, 8, 10, 12, or 14, respectively; and a polynucleotide specifically hybridizing to a partial region in SEQ ID NO: 1 or 3 is used for measurement of the amount of mRNA encoding the human CAPRIN-1 of SEQ ID NO: 2 or 4, respectively. However, a protein from a mammal and a homolog thereof from another mammal generally share high sequence identity even at the nucleotide sequence level. Thus, the sequence identity among the sequences of the odd-numbered SEQ ID NOS: 1-13 also is as very high as 94% to 100%. Accordingly, a polynucleotide specifically hybridizing to a partial region of the sequence of SEQ ID NO: 5 can also specifically hybridize to a partial region corresponding to the relevant partial region of any of the odd-numbered SEQ ID NOs: 1-29.

Actually as described in Examples below, a pair of primers having the nucleotide sequences shown in SEQ ID NO: 33 and 34, respectively, specifically hybridizes to both a partial region of any of the sequences of the odd-numbered SEQ ID NOS: 1-29 and a partial region of the sequence of SEQ ID NO: 5, so that both mRNA encoding the canine CAPRIN-1 of SEQ ID NO: 6 and mRNA encoding a homolog thereof can be measured, for example. Accordingly, for example, with the use of a polynucleotide specifically hybridizing to a partial region of the sequence of SEQ ID NO: 5, not only mRNA encoding the canine CAPRIN-1 of SEQ ID NO: 6, but also mRNA encoding the human CAPRIN-1 of SEQ ID NO: 2 or 4 can be measured. Similarly, a mRNA encoding CAPRIN-1 of another mammal such as a cat can also be measured. When a polynucleotide for cancer detection is designed, it is desirable to select partial regions having a specifically high sequence identity between the SEQ ID numbers (odd-numbered SEQ ID NOS: 1-29) (preferably, the nucleotide sequences are the same). If a partial region having particularly high sequence identity between a dog and a human is present, a region having very high sequence identity with the region is expected to be present in a homologous gene of another animal species. Through selection of such partial regions, accuracy for measuring mRNA encoding CAPRIN-1 of an animal species other than dogs and humans can be increased.

A method itself for measuring a test nucleic acid using a polynucleotide specifically hybridizing to a partial region of the test nucleic acid as a primer or a probe for a nucleic acid amplification method such as PCR is well-known. Examples of such method include, in addition to RT-PCR that is specifically described in Examples below, Northern blot and In situ hybridization. When the amount of mRNA is measured in the present invention, all of these known measuring methods can be employed.

A nucleic acid amplification method itself such as PCR is well-known in the art and thus reagent kits and apparatuses therefor are commercially available, so that the method can be easily performed. Specifically, for example, denaturation, annealing, and extension steps are each performed using a test nucleic acid (e.g., the cDNA of a gene encoding a protein having an amino acid sequence shown in any of the even-numbered SEQ ID NOS: 2-30) as a template and a pair of polynucleotides (primers) for cancer detection in a known buffer in the presence of thermostable DNA polymerase such as Taq polymerase or Pfu polymerase and dNTP (here, N=A, T, C, or G) by varying the temperature of the reaction solution. In general, the denaturation step is performed at 90° C.-95° C., the annealing step is performed at or near the Tm of the template and the primers (preferably within ±4° C.), and the extension step is performed at 72° C. which is an optimum temperature for thermostable DNA polymerase such as Taq polymerase or Pfu polymerase or a temperature near the optimum temperature. Each step is performed for about 30 seconds to 2 minutes, as appropriately selected. This heating cycle is repeated about 25 to 40 times, for example, so that the template nucleic acid region flanked by a primer pair is amplified. A nucleic acid amplification method is not limited to PCR and any other nucleic acid amplification methods known in the art can be employed herein. As described above, when a nucleic acid amplification method is performed using a pair of polynucleotides for cancer detection as primers and a test nucleic acid as a template, the test nucleic acid is amplified. However, if no test nucleic acid is contained in a sample, amplification does not take place. Hence, through detection of amplification products, the presence or the absence of the test nucleic acid in a sample can be confirmed. An amplification product can be detected by a method that involves subjecting a reaction solution after amplification to electrophoresis, and then staining the band with ethidium bromide or the like or a method that involves immobilizing an amplification product after said electrophoresis onto a solid phase such as a nylon membrane, performing hybridization with a labeling probe that specifically hybridizes to a test nucleic acid, washing, and then detecting the label. Also, namely real-time detection PCR is performed using a quencher fluorescent dye and a reporter fluorescent dye, and thereby the amount of a test nucleic acid in a specimen can be quantitatively determined. Since kits for real-time detection PCR are commercially available, real-time detection PCR can be easily performed. Furthermore, semi-quantitative determination of a test nucleic acid is also possible based on electrophoresis band intensity. A test nucleic acid may be either mRNA or cDNA resulting from mRNA via reverse transcription. When mRNA is amplified as a test nucleic acid, a NASBA method (3SR method or TMA method) using the above primer pair can also be employed. The NASBA method itself is well-known and kits for the method are also commercially available, so that the method can be easily performed using the above primer pair.

As a probe, a labeled probe that is prepared by labeling a polynucleotide for cancer detection with a fluorescent label, a radiolabel, a biotin label, or the like can be used. A method for labeling a polynucleotide itself is well-known. The presence or the absence of a test nucleic acid in a sample can be examined by immobilizing a test nucleic acid or an amplification product thereof, performing hybridization with a labeled probe, washing, and then measuring the label bound to the solid phase. Alternatively, a polynucleotide for cancer detection is immobilized, a test nucleic acid is hybridized thereto, and then the test nucleic acid bound to the solid phase can be detected using the labeled probe or the like. In such a case, a polynucleotide for cancer detection bound to a solid phase is also referred to as a probe. A method for measuring a test nucleic acid using a polynucleotide probe is also known in the art. The method can be performed by causing, in a buffer, a polynucleotide probe to come into contact with a test nucleic acid at Tm or near Tm (preferably, within ±4° C.) for hybridization, washing, and then measuring the labeled probe that has hybridized or the template nucleic acid bound to the solid-phase probe. Examples of such method include well-known methods such as Northern blot, in situ hybridization, and Southern blot methods. In the present invention, any well-known method is applicable.

It is determined by the detection method of the present invention whether or not a subject animal has cancer based on the expression level of CAPRIN-1 measured as described above. Cancer can be detected only by measuring CAPRIN-1 expression in a subject animal. However, it is preferable in view of enhancing detection accuracy to examine the expression levels (antibody level, polypeptide level, or mRNA level) of CAPRIN-1 in one or a plurality of samples of healthy subjects so as to obtain a standard value of healthy subjects and then to compare the measured value of a subject animal with the standard value obtained from healthy subjects. To further enhance detection accuracy, CAPRIN-1 expression levels are examined for samples obtained from many patients found to have cancer so as to obtain a standard value of cancer patients and then the measured value of a subject animal may be compared with both the standard value of healthy subjects and the standard value of cancer patients. The above standard values can be determined by quantifying the CAPRIN-1 expression level in each sample and then calculating the mean value thereof, for example. A standard value of healthy subjects and the same of cancer patients can be determined in advance by examining CAPRIN-1 expression levels in many healthy subjects and cancer patients. Therefore, when comparison with a standard value is performed in the method of the present invention, a standard value determined in advance may be used.

In the detection method of the present invention, diagnosis based on other cancer antigens or cancer markers may be used in combination. Accordingly, cancer detection accuracy can be further increased. For example, when an antibody specifically existing in cancer patients is measured by the method of the present invention, another polypeptide that is often expressed in a cancer tissue can be used in combination as an antigen in a manner similar to that for polypeptides above. Also, the method of the present invention and diagnosis using a previously known cancer marker may be performed in combination.

Cancer can be detected in vivo according to the detection method of the present invention. Particularly, as described in Examples below, even a small-size tumor, which is invisible to the naked eye, or a tumor in a deep part in vivo can be detected according to the method of the present invention. Thus, the method of the present invention is useful for early cancer detection. Also, through application of the detection method of the present invention for a patient during follow-up after treatment of cancer, cancer can be detected early if a cancer recurrence has taken place.

Also, in a cancer-bearing living organism, as the number of cancer cells expressing CAPRIN-1 measured in the present invention increases, the amounts of the protein and its mRNA accumulated in the living organism increase and the production amount of the antibody against CAPRIN-1 in serum increases. Meanwhile, as the number of cancer cells decreases, the amounts of the protein and its mRNA accumulated in vivo decrease and the amount of the antibody against CAPRIN-1 in serum decreases. Therefore, when the expression level of CAPRIN-1 is higher than that of a control, it can be determined that a tumor increase or a cancer metastasis is occurring; that is, the extent of cancer is advanced. Actually, as specifically described in the Examples below, an increase in the above serum antibody level in a cancer-bearing living organism was observed in association with cancer progression (malignant) such as tumor increase and metastasis. As described above, the extent of cancer can also be detected by the method of the present invention.

Also, as described in Examples below, among tumors of the same type, the above antibody levels in malignant type tumors were significantly higher than those in benign type tumors. Accordingly, when the expression level of CAPRIN-1 is high, it can be determined that cancer malignancy is higher. Specifically, cancer malignancy can also be detected by the method of the present invention.

Cancer to be subjected to the method for detecting cancer of the present invention is cancer expressing CAPRIN-1. Examples of such cancer include, but are not limited to, brain tumor, squamous cell carcinoma of the head, neck, lung, uterus or esophagus, melanoma, adenocarcinoma of the lung or uterus, renal cancer, malignant mixed tumor, hepatocellular carcinoma, basal cell carcinoma, acanthoma-like gingival tumor, tumor of the oral cavity, perianal adenocarcinoma, anal sac tumor, anal sac apocrine adenocarcinoma, sertoli cell carcinoma, cancer of the vaginal vestibule, sebaceous adenocarcinoma, sebaceous epithelioma, sebaceous adenoma, sweat gland carcinoma, intranasal adenocarcinoma, nasal adenocarcinoma, thyroid cancer, large-bowel cancer, bronchial adenocarcinoma, adenocarcinoma, ductal carcinoma, breast adenocarcinoma, composite type breast adenocarcinoma, malignant mammary mixed tumor, intraductal papillary adenocarcinoma, fibrosarcoma, hemangiopericytoma, osteosarcoma, chondrosarcoma, soft tissue sarcoma, histiocytic sarcoma, myxosarcoma, undifferentiated sarcoma, lung cancer, mastocytoma, cutaneous leiomyoma, intraperitoneal leiomyoma, leiomyoma, chronic lymphocytic leukemia, lymphoma, gastrointestinal lymphoma, digestive lymphoma, small-cell-to-medium-cell lymphoma, adrenomedullary tumor, granulosa cell tumor, and pheochromocytoma. Also, a living organism to be subjected to the method of the present invention is a mammal and is preferably a human, a dog, or a cat.

Examples of a sample to be subjected to the method of the present invention include body fluids such as blood, serum, blood plasma, ascites, and pleural effusion, tissues, and cells. In particular, in the $1^{st}$ method and the $2^{nd}$ method above, serum, blood plasma, ascites, and pleural effusion can be preferably used and in the $3^{rd}$ method above for measurement of mRNA, tissue samples and cell samples are preferable.

The above polypeptides to be used as antigens for immunoassay in the $1^{st}$ method (that is, the canine CAPRIN-1 of SEQ ID NO: 2 and a homolog thereof, a specifically reactive partial polypeptide, a specifically reactive modified polypeptide, and a specifically reactive addition polypeptide) can be provided as reagents for cancer detection. The reagent may consist of only the above polypeptide or may contain various additives or the like, for example, useful for stabilization of the polypeptide. Also, the reagent can be provided in a form immobilized onto a solid phase such a plate or a membrane. Preferable examples of the polypeptide are as described above.

An antibody that undergoes an antigen-antibody reaction with CAPRIN-1 or an antigen-binding fragment thereof, which is used for immunoassay of CAPRIN-1 itself in the $2^{nd}$ method, can also be provided as a reagent for cancer detection. The reagent for cancer detection in this case may also consist of only the above antibody or an antigen-binding fragment thereof or may contain various additives or the like useful for stabilization and the like of the antibody or an antigen-binding fragment thereof. Also, the antibody or an antigen-binding fragment thereof may be in a form binding to a metal such as manganese or iron. When such metal-bound antibody or antigen-binding fragment thereof is administered to the body of a living organism, the metal-bound antibody or antigen-binding fragment thereof is accumulated at an increased level at a site where the antigen protein is present at a higher level. Therefore, the metal is measured by MRI or the like, and thereby the presence of cancer cells producing the antigen protein can be detected.

Furthermore, the above polynucleotide for cancer detection to be used for mRNA measurement in the $3^{rd}$ method can also be provided as a reagent for cancer detection. The reagent for cancer detection in this case may also consist of only the polynucleotide or may contain various additives and the like useful for stabilization and the like of the polynucleotide. The polynucleotide for cancer detection contained in the reagent is preferably a primer or a probe. Conditions and preferable examples of the polynucleotide for cancer detection are as described above.

EXAMPLES

The present invention will be described in more detail with reference to the examples set forth below; however, the technical scope of the present invention is not limited to the examples.

Example 1: Obtainment of New Cancer Antigen Protein by SEREX Method (1) Construction of cDNA Library Total RNA was extracted from a testis tissue of a healthy dog by an Acid guanidium-Phenol-Chloroform method and then a polyA RNA was purified using Oligotex-dT30 mRNA purification Kit (Takara Shuzo Co., Ltd.) according to protocols included with the kit.

A canine testis cDNA phage library was synthesized using the thus obtained mRNA (5 μg). The cDNA phage library was constructed using a cDNA Synthesis Kit, a ZAP-cDNA Synthesis Kit, and a ZAP-cDNA GigapackIII Gold Cloning Kit (STRATAGENE) according to protocols included with the kits. The size of the thus constructed cDNA phage library was $7.73\times10^5$ pfu/ml.

(2) Screening of cDNA Library Using Serum

Immunoscreening was performed using the above constructed canine testis cDNA phage library. Specifically, host *Escherichia coli* (XL1-Blue MRF') was infected with the phage on an NZY agarose plate (Φ90×15 mm) so as to obtain 2210 clones. *E. coli* cells were cultured at 42° C. for 3 to 4 hours to form plaques. The plate was covered with a nitrocellulose membrane (Hybond C Extra: GE Healthcare Bio-Science) impregnated with IPTG (isopropyl-β-D-thiogalactoside) at 37° C. for 4 hours, so that the protein was induced, expressed, and then transferred to the membrane. Subsequently, the membrane was collected and then immersed in TBS (10 mM Tris-HCl, 150 mM NaCl, and pH 7.5) containing 0.5% powdered skim milk, followed by overnight shaking at 4° C., thereby suppressing nonspecific reaction. The filter was reacted with a 500-fold diluted serum of a canine patient at room temperature for 2 to 3 hours.

As the above serum of a canine patient, a serum collected from a canine patient with breast cancer was used. These sera were stored at −80° C. and then subjected to pretreatment immediately before use. A method for pretreatment of serum is as follows. Specifically, host *Escherichia coli* (XL1-Blue MRF') was infected with a λ ZAP Express phage in which no foreign gene had been inserted and then cultured overnight on a NZY plate medium at 37° C. Subsequently, buffer (0.2 M $NaHCO_3$ and pH 8.3) containing 0.5 M NaCl was added to the plate, the plate was left to stand at 4° C. for 15 hours, and then a supernatant was collected as an *Escherichia coli*/phage extract. Next, the thus collected *Escherichia coli*/phage extract was applied to an NHS-column (GE Healthcare Bio-Science), so that an *Escherichia coli*•phage-derived protein was immobilized. The serum of a canine patient was applied to the protein-immobilized column for reaction and then *Escherichia coli* and an antibody adsorbed to the phage were removed from the serum. The serum fraction that had passed through the column was diluted 500-fold with TBS containing 0.5% powdered skim milk. The resultant was used as an immunoscreening material.

A membrane onto which the treated serum and the above fusion protein had been blotted was washed 4 times with TBS-T (0.05% Tween20/TBS) and then caused to react with goat anti-canine IgG (Goat anti-Dog IgG-h+I HRP conjugated (BETHYL Laboratories)) diluted 5000-fold with TBS containing 0.5% powdered skim milk as a secondary antibody for 1 hour at room temperature. Detection was performed via an enzyme coloring reaction using an NBT/BCIP reaction solution (Roche). Colonies that matched sites positive for a coloring reaction were collected from the NZY agarose plate (Φ90×15 mm) and then suspended in 500 μl of an SM buffer (100 mM NaCl, 10 mM $MgClSO_4$, 50 mM Tris-HCl, 0.01% gelatin, and pH 7.5). Until colonies positive for coloring reaction were unified, secondary screening and tertiary screening were repeated by a method similar to the above, so that 30,940 phage clones reacting with serum IgG were screened. Thus, 5 positive clones were isolated.

(3) Homology Search for Isolated Antigen Gene

For nucleotide sequence analysis of the 5 positive clones isolated by the above method, a procedure for conversion from phage vectors to plasmid vectors was performed. Specifically, 200 μl of a solution was prepared to contain host *Escherichia coli* (XL1-Blue MRF') so that absorbance $OD_{600}$ was 1.0. The solution was mixed with 250 μl of a purified phage solution and then with 1 μl of an ExAssist helper phage (STRATAGENE), followed by 15 minutes of reaction at 37° C. Three mililiters of LB medium was added and then culture was performed at 37° C. for 2.5 to 3 hours. Immediately after culture, the temperature of the solution was kept at 70° C. by water bath for 20 minutes, centrifugation was performed at 4° C. and 1000×g for 15 minutes, and then the supernatant was collected as a phagemid solution. Subsequently, 200 μl of a solution was prepared to contain phagemid host *Escherichia coli* (SOLR) so that absorbance $OD_{600}$ was 1.0. The solution was mixed with 10 μl of a purified phage solution, followed by 15 minutes of reaction at 37° C. The solution (50 μl) was seeded on LB agar medium containing ampicillin (to a final concentration of 50 μg/ml) and then cultured overnight at 37° C. Transformed SOLR single colonies were collected and then cultured in LB medium containing ampicillin (final concentration: 50 μg/ml) at 37° C. A plasmid DNA containing an insert of interest was purified using a QIAGEN plasmid Miniprep Kit (QIAGEN).

The purified plasmid was subjected to analysis of the full-length sequence by a primer walking method using the T3 primer according to SEQ ID NO: 31 and the T7 primer according to SEQ ID NO: 32. As a result of sequence analysis, the gene sequences according to SEQ ID NOS: 5, 7, 9, 11, and 13 were obtained. A homology search program, BLAST search (http://www.ncbi.Nlm.Nih.gov/BLAST/), was performed using the nucleotide sequences of the genes and amino acid sequences (SEQ ID NOS: 6, 8, 10, 12, and 14) of the proteins encoded by the genes. As a result of this homology search with known genes, it was revealed that all of the 5 obtained genes encoded CAPRIN-1. Regarding regions to be translated to proteins, the sequence identity among the 5 genes was 100% in terms of nucleotide sequence and 99% in terms of amino acid sequence. Also, regarding regions to be translated to proteins, the sequence identity between the genes and genes encoding human homolog thereof was 94% in terms of nucleotide sequence and 98% in terms of amino acid sequence. The nucleotide sequences of the human homolog are shown in SEQ ID NOS: 1 and 3 and the amino acid sequences of the same are shown in SEQ ID NOS: 2 and 4. Also, regarding regions to be translated to proteins, the sequence identity between the obtained canine genes and a gene encoding a cattle homolog was 94% in terms of nucleotide sequence and 97% in terms of amino acid sequence. The nucleotide sequence of the cattle homolog is shown in SEQ ID NO: 15 and the amino acid sequence of the same is shown in SEQ ID NO: 16. Regarding regions to be translated to proteins, the sequence identity between the genes encoding the human homolog and the gene encoding the cattle homolog was 94% in terms of nucleotide sequence and ranged from 93% to 97% in terms of amino acid sequence. Also, regarding regions to be translated to proteins, the sequence identity between the obtained canine genes and a gene encoding an equine homolog was 93% in terms of nucleotide sequence and 97% in terms of amino acid sequence. The nucleotide sequence of the equine homolog is shown in SEQ ID NO: 17 and the amino acid sequence of the same is shown in SEQ ID NO: 18. Regarding regions to be translated to proteins, the sequence identity between the genes encoding the human homolog and the gene encoding the equine homolog was 93% in terms of nucleotide sequence and 96% in terms of amino acid sequence. Also, regarding regions to be translated to proteins, the sequence identity between the obtained canine genes and genes encoding mouse homolog ranged from 87% to 89% in terms of nucleotide sequence and ranged from 95% to 97% in terms of amino acid sequence. The nucleotide sequences of the mouse homolog are shown in SEQ ID NOS: 19, 21, 23, 25, and 27 and the amino acid sequences of the same are shown in SEQ ID NOS: 20, 22, 24, 26, and 28. Regarding regions to be translated to proteins, the sequence identity between the genes encoding the human homolog and the genes encoding the mouse homolog ranged from 89% to 91% in terms of nucleotide sequence and ranged from 95% to 96% in terms of amino acid sequence. Also, regarding regions to be translated to proteins, the sequence identity between the obtained canine genes and a gene encoding a chicken homolog was 82% in terms of nucleotide sequence and 87% in terms of amino acid sequence. The nucleotide sequence of the chicken homolog is shown in SEQ ID NO: 29 and the amino acid sequence of the same is shown in SEQ ID NO: 30. Regarding regions to be translated to proteins, the sequence identity between the genes encoding the human homolog and the gene encoding the chicken homolog ranged from 81% to 82% in terms of nucleotide sequence and was 86% in terms of amino acid sequence.

(4) Gene Expression Analysis in Each Tissue

Expression of the genes obtained by the above method in canine and human normal tissues and various cell lines was examined by an RT-PCR (Reverse Transcription-PCR) method. A reverse transcription reaction was performed as follows. Specifically, total RNA was extracted from each tissue (50 mg to 100 mg) and each cell line (5 to $10\times10^6$ cells) using a TRIZOL reagent (Invitrogen Corporation) according to protocols included therewith. cDNA was synthesized using the total RNA and Superscript First-Strand Synthesis System for RT-PCR (Invitrogen Corporation) according to protocols included therewith. PCR was performed as follows using primers specific to the obtained genes (according to SEQ ID NOS: 33 and 34). Specifically, PCR was performed by preparing a reaction solution adjusted to a total amount of 25 μl through addition of each reagent and an included buffer (0.25 μl of a sample prepared by reverse transcription reaction, the above primers (2 μM each), dNTP (0.2 mM each), and 0.65 U of ExTaq polymerase (Takara-baio Co., Ltd.)) and then by reacting the solution through repeating 30 times a cycle of 94° C./30 seconds, 60° C./30 seconds, and 72° C./30 seconds using a Thermal Cycler (BIO RAD). The gene-specific primers mentioned above were used to amplify the region between nucleotide 206 and nucleotide 632 in the nucleotide sequence of SEQ ID NO: 5 (canine CAPRIN-1 gene) and the region between nucleotide 698 and nucleotide 1124 in the nucleotide sequence of SEQ ID NO: 1 (human CAPRIN-1 gene). For control, GAPDH-specific primers (according to SEQ ID NOS: 35 and 36) were used at the same time. As a result, as shown in FIG. 1, strong expression was observed in testis in the case of healthy canine tissues, while expression was observed in canine breast cancer and adenocarcinoma tissues. Furthermore, expression of the human homolog of the obtained genes was also confirmed. As a result, similarly to the case of canine CAPRIN-1 genes, expression could be confirmed only in the testis in the case of normal tissues. However, in the case of cancer cells, expression was detected in many types of cancer cell line, such as cell lines of breast cancer, brain tumor, leukemia, lung cancer, and esophageal cancer. Expression was confirmed in a particularly large number of breast cancer cell lines. Based on the results, it was confirmed that CAPRIN-1 expression was not observed in normal tissues other than those of the testis, while CAPRIN-1 was expressed in many cancer cells and particularly in breast cancer cell lines.

In addition, in FIG. 1, Reference No. 1 along the longitudinal axis indicates the expression pattern of each of the above-identified genes and Reference No. 2 along the same indicates the expression pattern of the GAPDH gene for control.

(5) Immunohistochemical Staining (5)-1 CAPRIN-1 Expression in Normal Mouse and Canine Tissues Mice (Balb/c, female) and dogs (beagle dogs, female) were exsanguinated under ether anesthesia and ketamine/isoflurane anesthesia. After laparotomy, organs (stomach, liver, eyeball, thymus gland, muscle, bone marrow, uterus, small intestine, esophagus, heart, kidney, salivary gland, large intestine, mammary gland, brain, lung, skin, adrenal gland, ovary, pancreas, spleen, and bladder) were each transferred to a 10 cm dish containing PBS. Each organ was cut open in PBS and then fixed by perfusion overnight with 0.1 M phosphate buffer (pH 7.4) containing 4% paraformaldehyde (PFA). The perfusate was discarded, the tissue surface of each organ was rinsed with PBS, and then a PBS solution containing 10% sucrose was added to a 50 ml centrifugal tube. Each tissue was then placed in each tube and then shaken using a rotor at 4° C. for 2 hours. Each solution was substituted with a PBS solution containing 20% sucrose and then left to stand at 4° C. until tissues precipitated. Each solution was substituted with a PBS solution containing 30% sucrose and then left to stand at 4° C. until tissues precipitated. Each tissue was removed and a necessary portion was excised with a surgical scalpel. Next, an OCT compound (Tissue Tek) was applied and spread over each tissue surface, and then the tissues were placed on Cryomold. Cryomold was placed on dry ice for rapid freezing. Tissues were sliced into pieces 10 to 20 μm long using a cryostat (LEICA) and then the sliced tissue pieces were air-dried on glass slides for 30 minutes using a hair dryer, so that glass slides onto which sliced tissue pieces had been applied were prepared. Next, each glass slide was placed in a staining bottle filled with PBS-T (saline containing 0.05% Tween20), so that a procedure involving exchange with PBS-T every 5 minutes was performed 3 instances. Excess water around each specimen was removed using Kimwipes and then each section was encircled using DAKOPEN (DAKO). As blocking solutions, a MOM mouse Ig blocking reagent (VECTASTAIN) was applied onto mouse tissue and PBS-T solution containing a 10% fetal calf serum was applied onto canine tissue. The resultants were left to stand in a moist chamber at room temperature for 1 hour. Next, a solution prepared with the blocking solution to a 10 μg/ml anti-CAPRIN-1 monoclonal antibody (monoclonal antibody #8) having the heavy chain variable region of SEQ ID NO: 55 and the light chain variable region of SEQ ID NO: 56, which reacts with the cancer cell surfaces prepared in Example 3, was applied onto each slide glass and then left to stand within a moist chamber at 4° C. overnight. After 3 instances of 10 minutes of washing with PBS-T, a MOM biotin-labeled anti-IgG antibody (VECTASTAIN) diluted 250-fold with the blocking solution was applied onto each glass slide and then left to stand within a moist chamber at room temperature for 1 hour. After 3 instances of 10 minutes of washing with PBS-T, an avidin-biotin ABC reagent (VECTASTAIN) was applied and then left to stand within a moist chamber at room temperature for 5 minutes. After 3 instances of 10 minutes of washing with PBS-T, a DAB staining solution (DAB 10 mg+30% $H_2O_2$ 10 μl/0.05 M Tris-HCl (pH 7.6) 50 ml) was applied and then the glass slides were left to stand within a moist chamber at room temperature for 30 minutes. Glass slides were rinsed with distilled water and then a hematoxylin reagent (DAKO) was applied. After being left to stand at room temperature for 1 minute, the glass slides were rinsed with distilled water. The glass slides were immersed in 70%, 80%, 90%, 95%, and 100% ethanol solutions in such order for 1 minute each and then left to stand in xylene overnight. The glass slides were removed, coverslipped with Glycergel Mounting Medium (DAKO), and then observed. As a result, CAPRIN-1 expression was observed to a slight degree within cells in all salivary gland, kidney, colon, and stomach tissues, but CAPRIN-1 expression was never observed on cell surfaces. Also, absolutely no CAPRIN-1 expression was observed in tissues from other organs.

(5)-2 CAPRIN-1 Expression in Canine Breast Cancer Tissue

With the use of 108 frozen canine breast cancer tissue specimens from dogs diagnosed by pathological diagnosis as having malignant breast cancer, frozen section slides were prepared by a method similar to the above and immunohistochemical staining was performed using the monoclonal antibody #8 prepared in Example 3. As a result, CAPRIN-1 expression was confirmed in 100 out of the 108 specimens (92.5%). CAPRIN-1 was particularly strongly expressed on the surfaces of highly atypical cancer cells.

(5)-3 CAPRIN-1 Expression in Human Breast Cancer Tissue

Immunohistochemical staining was performed using 188 breast cancer tissue specimens of a paraffin-embedded human breast cancer tissue array (BIOMAX). After 3 hours of treatment at 60° C., the human breast cancer tissue array was immersed into a staining bottle filled with xylene and then xylene replacement every 5 minutes was performed 3 instances. Next, a similar procedure was performed using ethanol and PBS-T instead of xylene. The human breast cancer tissue array was immersed into a staining bottle filled with 10 mM citrate buffer (pH6.0) containing 0.05% Tween20, treated for 5 minutes at 125° C., and then left to stand at room temperature for 40 minutes or more. Excess water around each specimen was removed from the array using Kimwipes, each section was encircled using DAKOPEN (DAKO), and then an appropriate amount of Peroxidase Block (DAKO) was added dropwise onto the array. The array was left to stand at room temperature for 5 minutes and then immersed into a staining bottle filled with PBS-T. PBS-T replacement every 5 minutes was performed 3 instances. As a blocking solution, a PBS-T solution containing 10% FBS was applied onto the array and then the array was left to stand within a moist chamber at room temperature for 1 hour. Next, the monoclonal antibody #8 prepared in Example 3 adjusted to 10 μg/ml using a PBS-T solution containing 5% FBS was applied and then the array was left to stand overnight within a moist chamber at 4° C. After 3 instances of 10 minutes of washing with PBS-T, an appropriate amount of Peroxidase Labeled Polymer Conjugated (DAKO) was added dropwise onto the array, and then the array was left to stand at room temperature for 30 minutes within a moist chamber. After 3 instances of 10 minutes of washing with PBS-T, a DAB staining solution (DAKO) was applied onto the array and then the array was left to stand at room temperature for 10 minutes. The DAB staining solution was discarded from the array and then 10 minutes of washing was performed with PBS-T for 3 instances. The array was rinsed with distilled water and then immersed in 70%, 80%, 90%, 95%, and 100% ethanol solutions in order for 1 minute each and then left to stand in xylene overnight. The array was removed, coverslipped with Glycergel Mounting Medium (DAKO), and then observed. As a result, strong CAPRIN-1 expression was observed for 138 (73%) out of the total 188 breast cancer tissue specimens.

(5)-4 CAPRIN-1 Expression in Human Malignant Brain Tumor

With the use of 247 malignant brain tumor tissue specimens of paraffin-embedded human malignant brain tumor tissue arrays (BIOMAX), immunohistochemical staining was performed by a method similar to that in (5)-3 above using the monoclonal antibody #8 prepared in Example 3. As a result, strong CAPRIN-1 expression was observed in 227 (92%) out of the total 247 malignant brain tumor tissue specimens.

(5)-5 CAPRIN-1 Expression in Human Breast Cancer Metastatic Lymph Node

With the use of 150 tissue specimens of human breast cancer metastatic lymph nodes of paraffin-embedded human breast cancer metastatic lymph node tissue arrays (BIOMAX), immunohistochemical staining was performed by a method similar to that in (5)-3 above using the monoclonal antibody #8 prepared in Example 3. As a result, strong CAPRIN-1 expression was observed in 136 (90%) out of the total 150 tissue specimens of human breast cancer metastatic lymph nodes. Specifically, it was revealed that CAPRIN-1 is also strongly expressed in a cancer tissue that has metastasized from breast cancer.

Example 2: Preparation of New Canine and Human Cancer Antigen Proteins (1) Preparation of Recombinant Protein A recombinant protein was prepared by the following method based on the gene of SEQ ID NO: 5 obtained in Example 1. PCR was performed by preparing a reaction solution adjusted to a total amount of 50 μl through addition of each reagent and an included buffer (1 μl of a vector prepared from the phagemid solution obtained in Example 1 and then subjected to sequence analysis, 2 types of primer (0.4 μM each; according to SEQ ID NOS: 37 and 38) containing Nde I and Kpn I restriction enzyme cleavage sequences, 0.2 mM dNTP, 1.25 U PrimeSTAR HS polymerase (Takara-baio Co., Ltd.)) and then by reacting the solution through repeating 30 times a cycle of 98° C./10 seconds and 68° C./1.5 minutes using a Thermal Cycler (BIO RAD). The above 2 types of primer were used to amplify the region encoding the full-length amino acid sequence of SEQ ID NO: 6 (P47). After PCR, the thus amplified DNA was subjected to 1% agarose gel electrophoresis and then a DNA fragment of about 1.4 kbp was purified from the gel using a QIAquick Gel Extraction Kit (QIAGEN).

The purified DNA fragment was ligated to a pCR-Blunt cloning vector (Invitrogen Corporation). The vector was transformed into *Escherichia coli* and then the plasmid was collected. It was confirmed based on the sequence that the amplified gene fragment matched the target sequence. The plasmid that matched the sequence of interest was treated with Nde I and Kpn I restriction enzymes and then the resultant was purified using a QIAquick Gel Extraction Kit. Then the gene sequence of interest was inserted into a pET30b expression vector (Novagen) for *Escherichia coli* treated with Nde I and Kpn I restriction enzymes. A His tag-fused recombinant protein can be produced using the vector. The plasmid was transformed into *Escherichia coli* BL21 (DE3) for expression and then expression induction was performed using 1 mM IPTG, so that the target protein was expressed within *Escherichia coli*.

Also, the recombinant protein of a canine homologous gene was prepared by the following method based on the gene of SEQ ID NO: 7. PCR was performed by preparing a reaction solution adjusted to a total amount of 50 μl through addition of each reagent and an included buffer (1 μl of cDNA from among cDNAs of various tissues and/or cells constructed in Example 1, for which the expression could be confirmed by an RT-PCR method, 2 types of primer (0.4 μM each; according to SEQ ID NOS: 39 and 40) containing Nde I and Kpn I restriction enzyme cleavage sequences, 0.2 mM dNTP, 1.25 U PrimeSTAR HS polymerase (Takara-baio Co., Ltd.)) and then by reacting the solution through repeating 30 times a cycle of 98° C./10 seconds and 68° C./2.5 minutes using a Thermal Cycler (BIO RAD). The above 2 types of primer were used to amplify the region encoding the full-length amino acid sequence of SEQ ID NO: 8. After PCR, the thus amplified DNA was fractionated with 1% agarose gel electrophoresis and then a DNA fragment of about 2.2 kbp was purified using a QIAquick Gel Extraction Kit (QIAGEN).

The purified DNA fragment was ligated to pCR-Blunt cloning vector (Invitrogen Corporation). The vector was transformed into *Escherichia coli*, and then the plasmid was collected. It was then confirmed based on the sequence that the amplified gene fragment matched the sequence of interest. The plasmid that matched the sequence of interest was treated with Nde I and Kpn I restriction enzymes and then the resultant was purified using a QIAquick Gel Extraction Kit. Then the gene sequence of interest was inserted into a pET30b expression vector (Novagen) for *Escherichia coli* treated with Nde I and Kpn I restriction enzymes. A His tag-fused recombinant protein can be produced using the vector. The plasmid was transformed into *Escherichia coli* BL21 (DE3) for expression and then expression induction was performed using 1 mM IPTG, so that the protein of interest was expressed within *Escherichia coli*.

Also, the recombinant protein of a human homologous gene was prepared by the following method based on the gene of SEQ ID NO: 1. PCR was performed by preparing a reaction solution adjusted to a total amount of 50 μl through addition of each reagent and an included buffer (cDNA (1 μl) from among cDNAs of various tissues and/or cells constructed in Example 1, for which the expression could be confirmed by an RT-PCR method, 2 types of primer (0.4 μM each; according to SEQ ID NOS: 41 and 42) containing Sac I and Xho I restriction enzyme cleavage sequences, 0.2 mM dNTP, 1.25 U PrimeSTAR HS polymerase (Takara-baio Co., Ltd.)) and then by reacting the solution through repeating 30 times a cycle of 98° C./10 seconds and 68° C./2.5 minutes using a Thermal Cycler (BIO RAD). The above 2 types of primer were used to amplify the region encoding the full-length amino acid sequence of SEQ ID NO: 2. After PCR, the thus amplified DNA was subjected to 1% agarose gel electrophoresis and then a DNA fragment of about 2.1 kbp was purified using a QIAquick Gel Extraction Kit (QIAGEN).

The purified DNA fragment was ligated to a cloning vector pCR-Blunt (Invitrogen Corporation). The vector was transformed into *Escherichia coli*, and then the plasmid was collected. It was then confirmed based on the sequence that the amplified gene fragment matched the sequence of interest. The plasmid that matched the sequence of interest was treated with Sac I and Xho I restriction enzymes and then the resultant was purified using a QIAquick Gel Extraction Kit. Then the gene sequence of interest was inserted into a pET30a expression vector (Novagen) for *Escherichia coli* treated with Sac I and Xho I restriction enzymes. A His tag-fused recombinant protein can be produced using the vector. The plasmid was transformed into *Escherichia coli* BL21 (DE3) for expression and then expression induction was performed using 1 mM IPTG, so that the protein of interest was expressed within *Escherichia coli*.

(2) Purification of Recombinant Protein

The above-obtained recombinant *Escherichia coli* expressing SEQ ID NO: 1, 5, or 7 was cultured at 37° C. in LB medium containing 30 μg/ml kanamycin until the absorbance at 600 nm reached around 0.7. Then isopropyl-β-D-1-thiogalactopyranoside was added to a final concentration of 1 mM, followed by 4 hours of culture at 37° C. Subsequently, cells were collected by 10 minutes of centrifugation at 4800 rpm. The cell pellet was suspended in phosphate buffered saline and then centrifuged at 4800 rpm for 10 minutes for washing cells.

The cells were suspended in phosphate buffered saline and then subjected to ultrasonication on ice. The thus ultrasonicated *Escherichia coli* solution was centrifuged at 6000 rpm for 20 minutes. The thus obtained supernatant was used as a soluble fraction and the thus obtained precipitate was used as an insoluble fraction.

Figure 2:
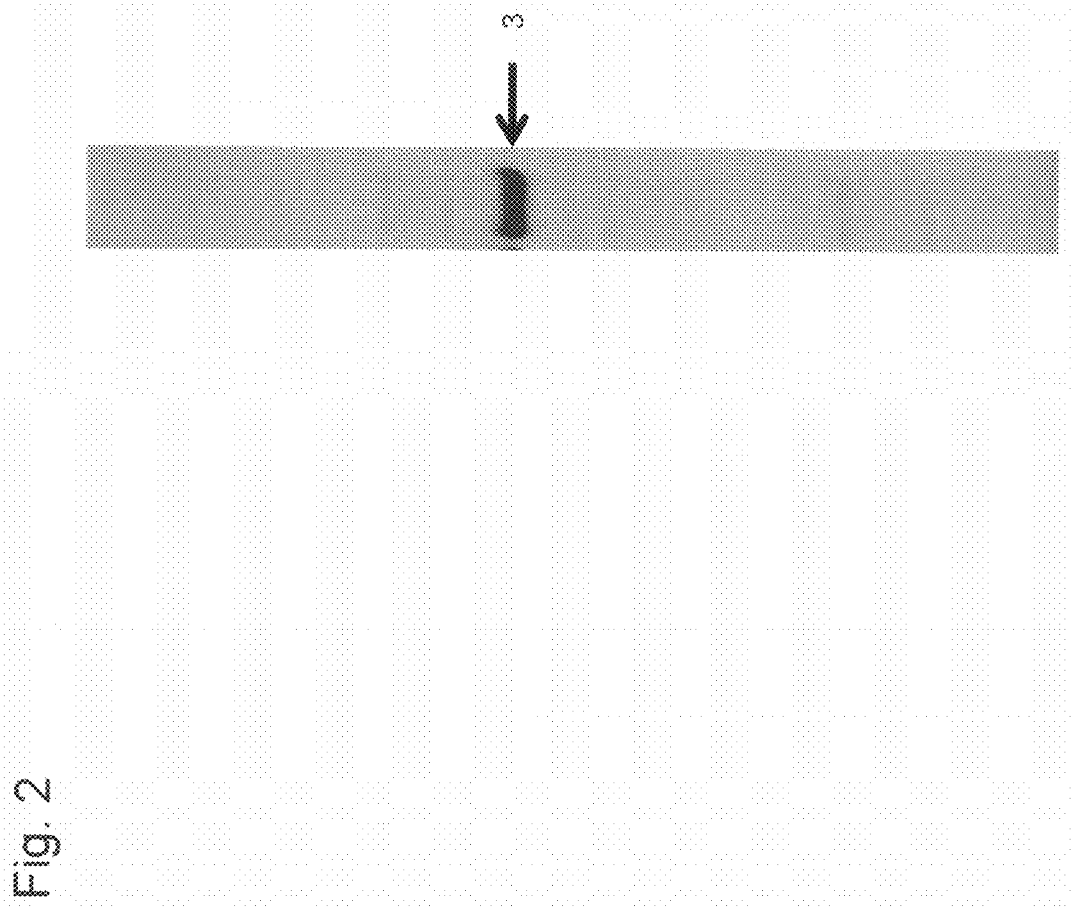
FIG. 2 shows the results of detecting by Coomassie staining the canine CAPRIN-1-derived polypeptide that is an example of polypeptides to be used in the present invention, which were produced and purified using *Escherichia coli* in the Examples. Reference No. 3 indicates the band of a canine CAPRIN-1-derived polypeptide.

The soluble fraction was added to a nickel chelate column (carrier: Chelating Sepharose (TradeMark) Fast Flow (GE Healthcare), column capacity: 5 mL, 50 mM hydrochloric acid buffer (pH 8.0) as equilibrated buffer)) prepared according to a conventional method. The unbinded fraction was washed with 50 mM hydrochloric acid buffer (pH 8.0) in an amount 10 times the capacity of the column and 20 mM phosphate buffer (pH8.0) containing 20 mM imidazole. Immediately after washing, 6 beds were eluted with 20 mM phosphate buffer (pH8.0) containing 100 mM imidazole. After the elution of the protein of interest had been confirmed by Coomassie staining, an elution fraction of 20 mM phosphate buffer (pH8.0) containing 100 mM imidazole was added to a strong anion exchange column (carrier: Q Sepharose (TradeMark) Fast Flow (GE Healthcare), column capacity: 5 mL, and 20 mM phosphate buffer (pH8.0) as equilibrated buffer). The unbinded fraction was washed with 20 mM phosphate buffer (pH7.0) in an amount 10 times the column capacity and 20 mM phosphate buffer (pH7.0) containing 200 mM sodium chloride. Immediately after washing, 5 beds were eluted using 20 mM phosphate buffer (pH7.0) containing 400 mM sodium chloride. Thus, purified fractions of proteins each having the amino acid sequence shown in SEQ ID NO: 2, 6, or 8 were obtained. These purified fractions were then used as materials for an administration test. FIG. 2 shows the result of the protein of SEQ ID NO: 2 fractionated by electrophoresis and detected by Coomassie staining.

200 μl of each purified preparation obtained by the above method was dispensed into 1 ml of reaction buffer (20 mM Tris-HCl, 50 mM NaCl, 2 mM $CaCl_2$ pH7.4) and then 2 μl of enterokinase (Novagen) was added. The preparation was left to stand at room temperature overnight for reaction, His tag was cleaved, and then purification was performed according to included protocols using an Enterokinase Cleavage Capture Kit (Novagen). Next, 1.2 ml of each purified preparation obtained by the above method was substituted with physiological phosphate buffer (Nissui Pharmaceutical Co., Ltd.) using ultrafiltration NANOSEP 10K OMEGA (PALL). Sterilized filtration was performed using 0.22 μm HT Tuffryn Acrodisc (PALL) and then the resultants were used for the following experiments.

Example 3: Preparation of Antibody Against CAPRIN-1

(1) Preparation of Polyclonal Antibody Against CAPRIN-1-Derived Peptide

To obtain an antibody binding to CAPRIN-1, CAPRIN-1-derived peptide (Arg-Asn-Leu-Glu-Lys-Lys-Lys-Gly-Lys- Leu-Asp-Asp-Tyr-Gln (SEQ ID NO: 43)) was synthesized. One milligram of the peptide as an antigen was mixed with an incomplete Freund's adjuvant (IFA) solution in an amount equivalent to the peptide. The mixture was subcutaneously administered to a rabbit 4 times every 2 weeks. Subsequently, blood was collected, so that an antiserum containing a polyclonal antibody was obtained. Furthermore, the antiserum was purified using a protein G carrier (GE Healthcare Bio-Sciences) and then a polyclonal antibody against the CAPRIN-1-derived peptide was obtained. Next, the reactivity of the obtained polyclonal antibody to the breast cancer cell surface was examined. Specifically, $10^6$ cells of the MDA-MB-231V human breast cancer cell line were subjected to centrifugation in a 1.5 ml microcentrifugal tube. A PBS solution supplemented with 0.1% fetal calf serum (FBS) containing the polyclonal antibody was added to the tube. The solution was left to stand on ice for 1 hour. After washing with PBS, an FITC-labeled goat anti-mouse IgG antibody (Invitrogen Corporation) diluted 500-fold with PBS containing 0.1% FBS was added to the solution, and then the solution was left to stand on ice for 1 hour. After washing with PBS, fluorescence intensity was measured using a FACS Calibur (Becton, Dickinson and Company). Meanwhile, a procedure similar to the above was performed so that a control was prepared by adding PBS containing 0.1% FBS instead of the polyclonal antibody. As a result, it was revealed that fluorescence intensity was found to be stronger in cells treated with the polyclonal antibody than that in control cells. Therefore, it was demonstrated that the obtained polyclonal antibody binds to the breast cancer cell surface.

(2) Preparation of Monoclonal Antibody Against CAPRIN-1 Protein

The antigen protein (human CAPRIN-1) (100 μg) shown in SEQ ID NO: 2 prepared in Example 2 was mixed with a MPL+TDM adjuvant (Sigma) in an amount equivalent to that of the antigen protein. The mixture was used as an antigen solution per mouse. The antigen solution was administered intraperitoneally to a 6-week-old Balb/c mouse (Japan SLC Inc.) and then further administered 3 instances every week. Spleen was removed on day 3 after the final immunization and then ground in between two sterilized glass slides. The resultant was washed with PBS (−) (Nissui) and then centrifuged at 1500 rpm for 10 minutes, so that a procedure to remove supernatants was repeated 3 instances. Thus, spleen cells were obtained. The thus obtained spleen cells were mixed with mouse myeloma cells SP2/0 (purchased from ATCC) at a ratio of 10:1. The PEG solution prepared by mixing 200 μl of RPMI1640 medium containing 10% FBS heated at 37° C. and 800 μl of PEG1500 (Boehringer) was added to the cells. The solution was left to stand for 5 minutes for cell fusion. Centrifugation was performed at 1700 rpm for 5 minutes to remove supernatants. Cells were suspended in 150 ml of RPMI1640 medium (HAT selective medium) containing 15% FBS, to which 2% equivalent of HAT solution (Gibco) had been added and then seeded onto fifteen 96-well plates (Nunc) at 100 μl per well. Cells were cultured for 7 days under conditions of 37° C. and 5% $CO_2$, so that hybridomas resulting from fusion of spleen cells to myeloma cells were obtained.

Hybridomas were selected using as an index the binding affinity of the antibody produced by the thus prepared hybridomas for the CAPRIN-1 protein. The CAPRIN-1 protein solution (1 μg/ml) prepared in Example 2 was added at 100 μl per well of 96-well plates and then left to stand at 4° C. for 18 hours. Each well was washed 3 instances with PBS-T, and then 0.5% Bovine Serum Albumin (BSA) solution (Sigma) was added at 400 μl per well, and then the plates were left to stand at room temperature for 3 hours. The solution was removed and then each well was washed 3 instances with 400 μl of PBS-T. Each culture supernatant of the hybridomas obtained above was added at 100 μl per well and then left to stand at room temperature for 2 hours. Each well was washed 3 instances with PBS-T, an HRP-labeled anti-mouse IgG (H+L) antibody (Invitrogen Corporation) diluted 5000-fold with PBS was added at 100 μl per well and then left to stand at room temperature for 1 hour. Each well was washed 3 instances with PBS-T A TMB substrate solution (Thermo) was added at 100 μl per well and then left to stand for 15-30 minutes, so that a color reaction was performed. After color development, 1N sulfuric acid was added at 100 μl per well to stop the reaction. Absorbance was measured at 450 nm and 595 nm using an absorption spectrometer. As a result, a plurality of hybridomas producing antibodies with high absorbances were selected.

The thus selected hybridomas were added at 0.5 hybridomas per well of 96-well plates and then cultured. After 1 week, hybridomas forming single colonies in wells were observed. Cells in these wells were further cultured. Hybridomas were selected using as an index the binding affinity of the antibody produced by cloned hybridomas for the CAPRIN-1 protein. The CAPRIN-1 protein solution (1 μg/ml) prepared in Example 2 was added at 100 μl per well of 96-well plates and then left to stand at 4° C. for 18 hours. Each well was washed 3 instances with PBS-T. A 0.5% BSA solution was added at 400 μl per well, and then left to stand at room temperature for 3 hours. The solution was removed and then each well was washed 3 instances with 400 μl of PBS-T. Each culture supernatant of the hybridomas obtained above was added at 100 μl per well and then left to stand at room temperature for 2 hours. Each well was washed 3 instances with PBS-T. An HRP-labeled anti-mouse IgG (H+L) antibody (Invitrogen Corporation) diluted 5000-fold with PBS was added at 100 μl per well and then left to stand at room temperature for 1 hour. Each well was washed 3 instances with PBS-T, a TMB substrate solution (Thermo) was added at 100 μl per well and then left to stand for 15-30 minutes, so that a color reaction was performed. After color development, 1N sulfuric acid was added at 100 μl per well to stop the reaction. Absorbance was measured at 450 nm and 595 nm using an absorption spectrometer. As a result, a plurality of hybridoma cell lines producing monoclonal antibodies exerting reactivity to the CAPRIN-1 protein were obtained. Culture supernatants of hybridomas were purified using a protein G carrier, so that 150 monoclonal antibodies binding to the CAPRIN-1 protein were obtained.

Next, from among these monoclonal antibodies, monoclonal antibodies exerting reactivity to the surfaces of breast cancer cells expressing CAPRIN-1 were selected. Specifically, $10^6$ cells of the MDA-MB-231V human breast cancer cell line were subjected to centrifugation with a 1.5 ml microcentrifugal tube. The supernatant (100 μl) of each hybridoma above was added and then left to stand on ice for 1 hour. After washing with PBS, an FITC-labeled goat anti-mouse IgG antibody (Invitrogen Corporation) diluted 500-fold with PBS containing 0.1% fetal calf serum was added and then left to stand on ice for 1 hour. After washing with PBS, fluorescence intensity was measured using FACS Calibur (Becton, Dickinson and Company). Meanwhile, a procedure similar to the above was performed so that a control supplemented with a medium instead of the antibody was prepared. As a result, 10 monoclonal antibodies (#1-

#10) having fluorescence intensity stronger than that of the control; that is, reacting with the surfaces of breast cancer cells were selected. The heavy chain variable regions and the light chain variable regions of these monoclonal antibodies were shown in SEQ ID NOS: 44-60. The above monoclonal antibody #1 comprises the heavy chain variable region of SEQ ID NO: 44 and the light chain variable region of SEQ ID NO: 45, the monoclonal antibody #2 comprises the heavy chain variable region of SEQ ID NO: 44 and the light chain variable region of SEQ ID NO: 46, the monoclonal antibody #3 comprises the heavy chain variable region of SEQ ID NO: 44 and the light chain variable region of SEQ ID NO: 47, the monoclonal antibody #4 comprises the heavy chain variable region of SEQ ID NO: 44 and the light chain variable region of SEQ ID NO: 48, the monoclonal antibody #5 comprises the heavy chain variable region of SEQ ID NO: 49 and the light chain variable region of SEQ ID NO: 50, the monoclonal antibody #6 comprises the heavy chain variable region of SEQ ID NO: 51 and the light chain variable region of SEQ ID NO: 52, the monoclonal antibody #7 comprises the heavy chain variable region of SEQ ID NO: 53 and the light chain variable region of SEQ ID NO: 54, the monoclonal antibody #8 comprises the heavy chain variable region of SEQ ID NO: 55 and the light chain variable region of SEQ ID NO: 56, the monoclonal antibody #9 comprises the heavy chain variable region of SEQ ID NO: 57 and the light chain variable region of SEQ ID NO: 58, and the monoclonal antibody #10 comprises the heavy chain variable region of SEQ ID NO: 59 and the light chain variable region of SEQ ID NO: 60.

(3) Identification of a Peptide in CAPRIN-1 Protein, to which an Antibody Against CAPRIN-1 Reacting to Cancer Cell Surface Binds With the use of monoclonal antibodies #1-#10 against CAPRIN-1, reacting with the surfaces of cancer cells obtained above, partial sequences in the CAPRIN-1 protein to be recognized by these monoclonal antibodies were identified.

First, DTT (Fluka) was added to 100 μl of a recombinant CAPRIN-1 protein solution adjusted to contain the protein at a concentration of 1 μg/μl with PBS to a final concentration of 10 mM, followed by 5 minutes of reaction at 95° C., so that reduction of disulfide bonds within the CAPRIN-1 protein was performed. Next, iodoacetamide (Wako Pure Chemical Industries, Ltd.) with a final concentration of 20 mM was added and then an alkylation reaction was performed for thiol groups at 37° C. for 30 minutes under shading conditions. Fifty microgram each of monoclonal antibodies #1-#10 against CAPRIN-1 was added to 40 μg of the thus obtained reduced-alkylated CAPRIN-1 protein. The volume of the mixture was adjusted to 1 mL of 20 mM phosphate buffer (pH7.0), and then the mixture was left to react overnight at 4° C. while stirring and mixing each mixture.

Next, trypsin (Promega) was added to a final concentration of 0.2 μg. After 1 hour, 2 hours, 4 hours, and then 12 hours of reaction at 37° C., the resultants were mixed with protein A-glass beads (GE) subjected in advance to blocking with PBS containing 1% BSA (Sigma) and washing with PBS in 1 mM calcium carbonate and NP-40 buffer (20 mM phosphate buffer (pH7.4), 5 mM EDTA, 150 mM NaCl, and 1% NP-40), followed by 30 minutes of reaction.

The reaction solutions were each washed with 25 mM ammonium carbonate buffer (pH8.0) and then antigen-antibody complexes were eluted using 100 μl of 0.1% formic acid. LC-MS analysis was conducted for eluates using Q-TOF Premier (Waters-MicroMass) according to protocols included with the instrument.

As a result, the polypeptide of SEQ ID NO: 61 was identified as a partial sequence of CAPRIN-1, which was recognized by all of the monoclonal antibodies #1-#10 against CAPRIN-1. Furthermore, the peptide of SEQ ID NO: 62 was identified as a partial sequence in the polypeptide of SEQ ID NO: 61 above, which was recognized by the monoclonal antibodies #1-#4, #5-#7, and #9. It was further revealed that the monoclonal antibodies #1-#4 recognized the peptide of SEQ ID NO: 63 that was a partial sequence peptide thereof.

Example 4: Cancer Diagnosis Using CAPRIN-1 Polypeptide (1) Canine Cancer Diagnosis Blood was collected from 342 canine patients confirmed to have malignant or benign tumors and 6 healthy dogs, and serum was separated. With the use of the canine CAPRIN-1 polypeptide (SEQ ID NO: 8) and the anti-canine IgG antibody prepared in Example 2, the titer of the serum IgG antibody specifically reacting with the polypeptide was measured by an ELISA method.

Immobilization of the thus prepared polypeptide was performed by adding a recombinant protein solution diluted to 5 μg/mL with phosphate buffered saline to 96-well immobilizer amino plates (Nunc) at 100 μl/well and then leaving the plates to stand at 4° C. overnight. Blocking was performed by adding a 50 mM sodium bicarbonate buffer solution (pH 8.4) (hereinafter, blocking solution) containing 0.5% BSA (bovine serum albumin) (Sigma Aldrich Japan) at 100 μl/well and then shaking the solution at room temperature for 1 hour. Serum diluted 1000-fold with the blocking solution was added at 100 μl/well and then the mixture was shaken at room temperature for 3 hours for reaction. The reaction solutions were washed 3 instances with phosphate buffered saline (hereinafter, PBS-T) containing 0.05% Tween20 (Wako Pure Chemical Industries, Ltd.). An HRP modified canine IgG antibody (Goat anti-Dog IgG-h+I HRP conjugated: BETHYL Laboratories) diluted 3000-fold with the blocking solution was added at 100 μl/well, followed by 1 hour of reaction at room temperature while shaking the solution. After 3 instances of washing with PBS-T, HRP substrate TMB (1-Step Turbo TMB (tetramethylbenzidine), PIERCE) was added at 100 μl/well and then an enzyme-substrate reaction was conducted at room temperature for 30 minutes. Subsequently, a 0.5 M sulfuric acid solution (Sigma Aldrich Japan) was added at 100 μl/well to stop the reaction. Absorbance at 450 nm was measured using a microplate reader. As controls, a specimen in connection with which no recombinant protein prepared had been immobilized and a specimen in connection with which a reaction with the serum of a cancer-bearing dog had not been conducted were similarly subjected to the above treatment and comparison.

As a result of pathologic diagnosis using excised tumor tissue, definitive diagnosis was made indicating that 215 out of the total 342 specimens used for the cancer diagnosis were malignant.

Specifically, specimens were diagnosed as having cancer such as malignant melanoma, malignant mixed tumor, hepatocellular carcinoma, basal cell carcinoma, acanthoma-like gingival tumor, tumor of oral cavity, perianal adenocarcinoma, anal sac tumor, anal sac apocrine adenocarcinoma, Sertoli cell carcinoma, cancer of vaginal vestibule, sebaceous adenocarcinoma, sebaceous epithelioma, sebaceous adenoma, sweat gland carcinoma, intranasal adenocarcinoma, nasal adenocarcinoma, thyroid cancer, large-bowel cancer, bronchial adenocarcinoma, adenocarcinoma, ductal carcinoma, breast adenocarcinoma, composite type breast adenocarcinoma, malignant mammary mixed tumor, intraductal papillary adenocarcinoma, fibrosarcoma, hemangiopericytoma, osteosarcoma, chondrosarcoma, soft tissue sarcoma, histiocytic sarcoma, myxosarcoma, undifferentiated sarcoma, lung cancer, mastocytoma, cutaneous leiomyoma, intraperitoneal leiomyoma, leiomyoma, squamous cell carcinoma, chronic lymphocytic leukemia, lymphoma, gastrointestinal lymphoma, digestive lymphoma, small-cell-to-medium-cell lymphoma, adrenomedullary tumor, granulosa cell tumor, and pheochromocytoma.

Figure 3:
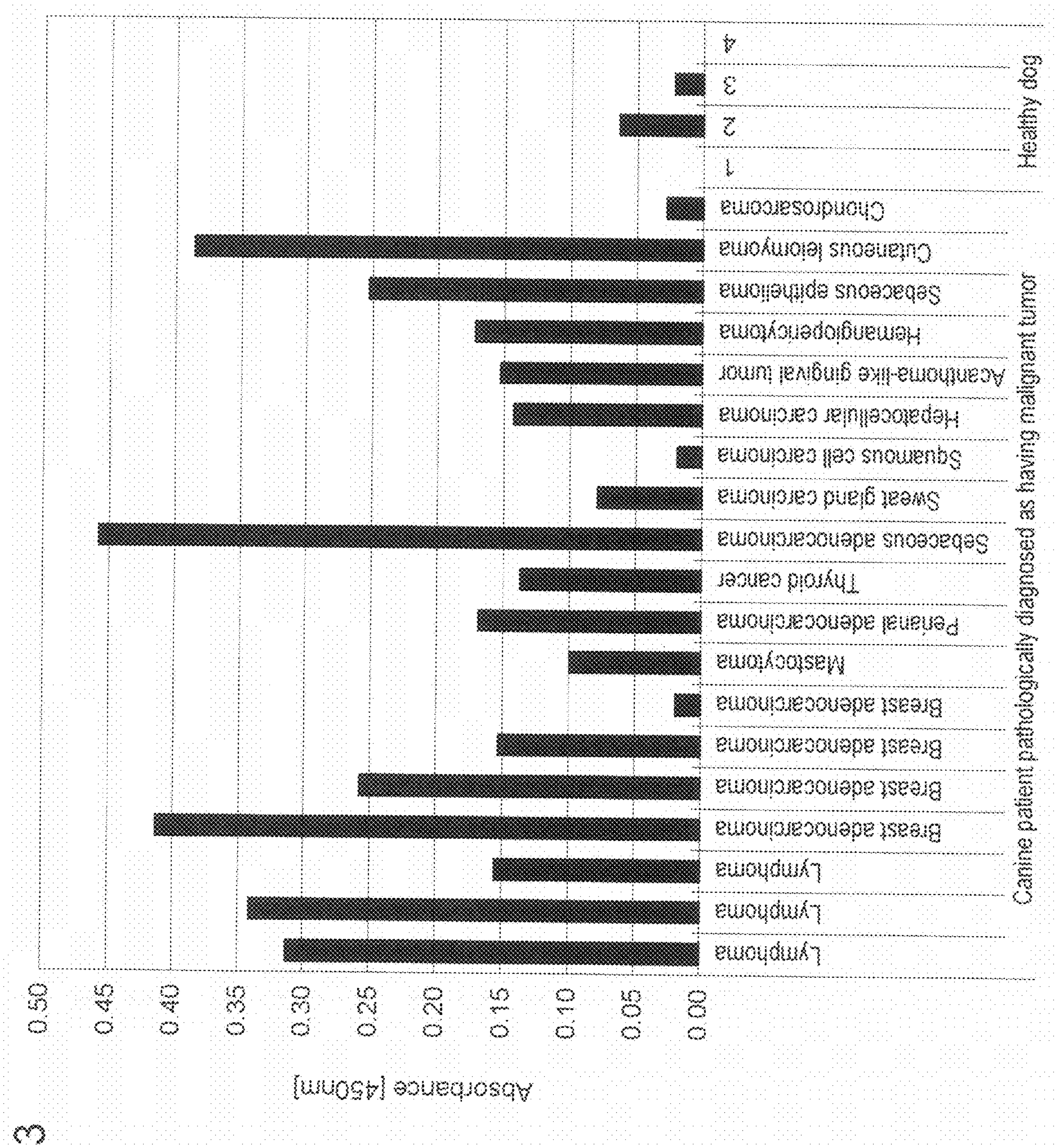
FIG. 3 shows some of the results of cancer diagnosis for cancer-bearing dogs using the canine CAPRIN-1-derived polypeptides prepared in the Examples.

The sera from the living bodies of these cancer-bearing dogs were found to have significantly high antibody titers against the recombinant protein as shown in FIG. 3. When the reference value as malignant cancer regarding the diagnostic method was determined to be twice or more the average value for healthy dogs, it was demonstrated that malignancy could be diagnosed for 108 specimens, which accounted for accounting for 50.2% of all the specimens. The cancer types of, these 108 specimens are as follows. Although development of a plurality of types of cancer had indicated for some specimens, the following numerical values are cumulative total values for each cancer type:

6 cases of malignant melanoma, 11 cases of lymphoma, 1 case of suppurative inflammation, 1 case of granulosa cell tumor, 4 cases of hepatocellular carcinoma, 3 cases of malignant testicular tumor, 3 cases of tumor of oral cavity, 7 cases of perianal adenocarcinoma, 12 cases of sarcoma, 35 cases of breast adenocarcinoma, 1 case of lung cancer, 6 cases of ductal carcinoma, 2 cases of sebaceous adenocarcinoma, 5 cases of mastocytoma, 1 case of smooth muscle sarcoma, 3 cases of squamous cell carcinoma, 2 cases of malignant mixed tumor, 1 case of hemangiopericytoma, 1 case of transitional epithelial cancer, 1 case of hemangiopericytoma, 1 case of hemangiopericytoma, and 1 case of sebaceous epithelioma.

As a result of similar diagnosis using pleural effusions and ascites collected from canine patients with terminal cancer, values similar to the results obtained by the diagnostic method using serum could be detected and cancer diagnosis could be made.

Figure 4:
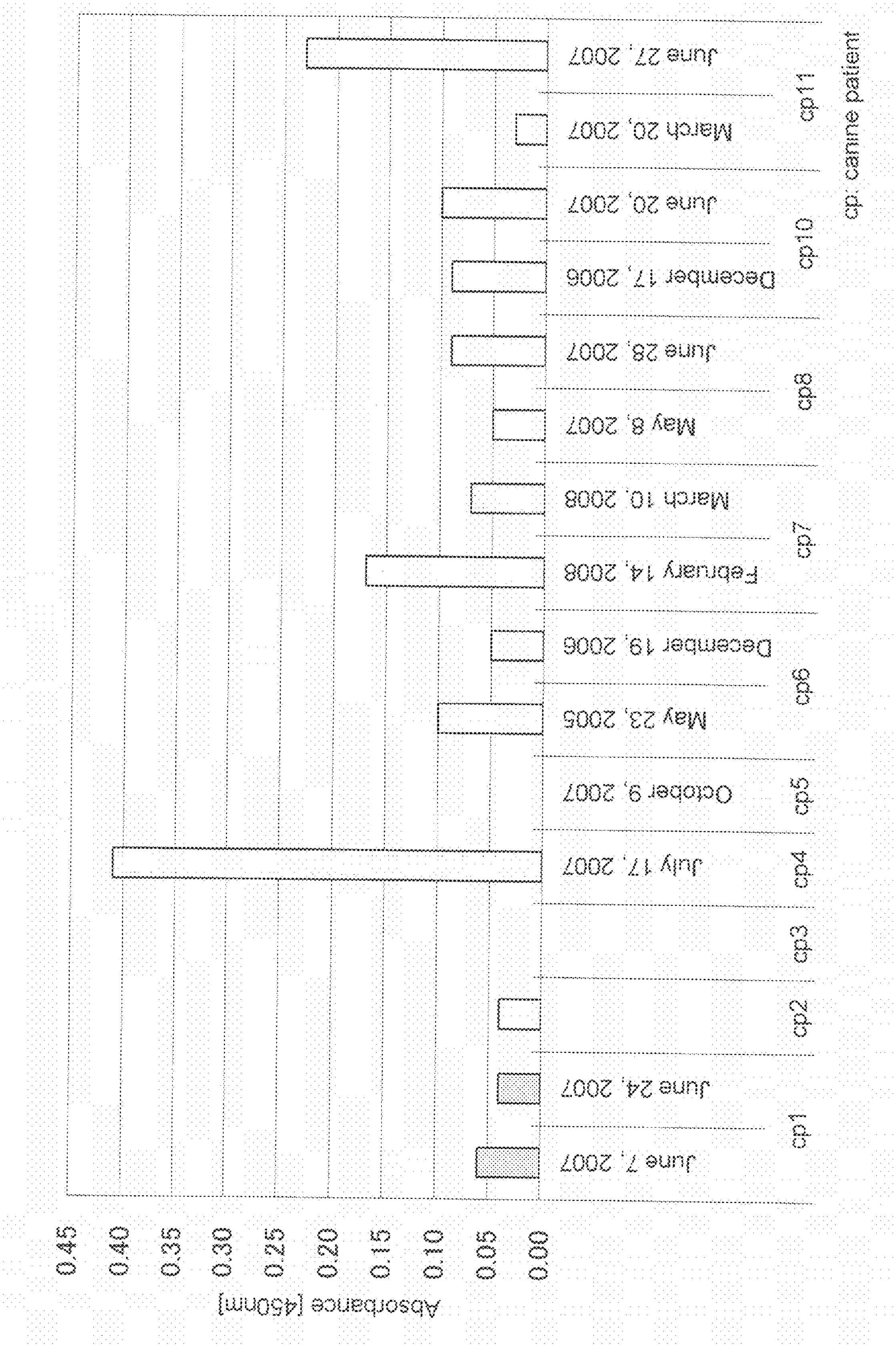
FIG. 4 shows some of the results of detailed cancer diagnosis for cancer-bearing dogs using the canine CAPRIN-1-derived polypeptides prepared in the Examples.

Also, it was demonstrated that the use of the diagnostic method enables diagnosis of cancer in a location invisible to the naked eye, the extent of cancer, malignancy or postoperative course of cancer, recurrence, metastasis, and the like. Several specific examples of detailed diagnosis shown in FIG. 4 are as described below.

(2)-1 Cancer Diagnosis for Tumor Invisible to the Naked Eye

On Jun. 7, 2007, no tumor mass was confirmed for canine patient 1 (flat coated retriever). However, about 20 days later, on Jun. 24, 2007, a peduncular tumor mass with a diameter of 2 mm was found in the gum at the root of the maxillary left cuspid tooth of canine patient 1. On the day when the mass was found, the peduncular portion was ligated and excised. Absorbance at 450 nm was found to be 0.06 before the tumor mass could be visually confirmed, and this figure was almost the same as 0.04, which was determined when the tumor was found. It was also demonstrated by the result that diagnosis of cancer in a location invisible to the naked eye, such as intraperitoneal cancer, is possible with the use of this technique.

In addition, it can be said that a warning sign of tumor development was successfully detected, since a rise in the aforementioned level could be confirmed before the tumor could be confirmed with the naked eye. Hence, it was confirmed that the technique is also useful for health examinations such as routine health checkups.

(2)-2 Diagnosis of the Extent of Cancer

The extent of cancer is determined based on tumor size, tumor depth, how the tumor affects the peripheral tissue, and the presence or the absence of metastasis. It was revealed that a higher value was detected when metastasis had occurred or cancer had progressed.

(2)-3 Diagnosis of Cancer Malignancy

Basal cell tumors include malignant basal cell tumors and benign basal cell tumors. In recent year, malignant basal cell tumors have tended to be classified as examples of basal cell carcinoma and benign basal cell tumors tend to be classified as examples of trichoblastoma according to the new WHO.

Canine patient 2 (Beagle) diagnosed as having basal cell carcinoma (malignant) was subjected to serodiagnosis upon surgery, so that the absorbance at 450 nm was found to be 0.04. Meanwhile, canine patient 3 (mongrel) diagnosed as having trichoblastoma (benign) was subjected to serodiagnosis upon surgery, so that the absorbance at 450 nm was found to be 0, indicating no detection. Therefore, it was demonstrated that different types of basal cell tumor, i.e., malignant basal cell carcinoma and benign trichoblastoma, can be diagnosed, even if they are classified as basal cell tumors.

Next, examples of mammary gland tumors are as follows. Mammary gland tumors are classified as malignant tumors such as breast adenocarcinoma and malignant mammary mixed tumor and benign mammary gland tumors exhibiting no malignant findings.

Canine patient 4 (Shetland Sheepdog) underwent extirpative surgery on Jul. 17, 2007, for breast adenocarcinoma. Canine patient 4 had 3 tumors. Pathologic diagnosis using isolated tissue resulted in the same diagnosis. Strongly atypical and invasive mammary gland tissue experienced somewhat widespread papillary-adenoid growth, and vascular invasion was also confirmed for the specimens. Thus, canine patient 4 was diagnosed as having highly malignant breast cancer. As a result of serodiagnosis using blood collected upon surgery, absorbance at 450 nm was found to be 0.41.

Meanwhile, canine patient 5 (toy poodle) had extirpative surgery on Oct. 9, 2007, for a mammary gland tumor. Pathologic diagnosis using isolated tissues at this time revealed that: whereas tumors were formed in which mammary gland epithelial cells and myoepithelial cells grew, myoepithelial cell components were uniform spindle cells and no malignancy was detected; and the mammary gland epithelial cell component exhibited a slight difference in size and dyskaryosis as observed. Hence, canine patient 5 was diagnosed as having a benign mammary gland tumor for which no malignancy was detected. As a result of blood collection and serodiagnosis upon surgery thereof, absorbance at 450 nm was found to be 0.

The above results for the 2 specimens revealed that the malignancy of a highly malignant tumor is greater than that of a benign low-malignant tumor.

Also, distribution of the diagnoses for 54 malignant tumor (breast cancer) specimens, such as breast adenocarcinoma or malignant mammary mixed tumor specimens and 21 benign mammary gland tumor specimens exhibiting no malignancy, were examined. Whereas benign mammary gland tumor specimens showed a distribution similar to that in the case of healthy dogs, breast cancer specimens showed a distribution of high values.

(2)-4 Diagnosis of Postoperative Course

Canine patient 6 (mongrel) visited the hospital because of mastocytoma and had extirpative surgery on May 23, 2005. As a result of serodiagnosis made at this time, absorbance at 450 nm was found to be 0.10. Mastocytoma is a tumor that repeatedly undergoes recurrence or metastasis when resected incompletely. Hence, whether or not complete tumor resection can be achieved by surgery is important. At the follow-up on Dec. 19, 2006, absorbance at 450 nm was found to be 0.05, so that a decreased antibody titer was confirmed. At this time, no recurrence was confirmed. Hence, in the case of canine patient 6, it can be said that since the tumor could be completely resected, the serodiagnosis results were lower than those upon surgery.

Canine patient 7 (Beagle) had extirpative surgery on Feb. 14, 2008, for mastocytoma. As a result of serodiagnosis performed at this time, absorbance at 450 nm was found to be 0.17. As a result of histopathological diagnosis using excised tissues, invasive hyperplasia was observed and Canine patient 7 was diagnosed as having mastocytoma corresponding to the moderately differentiated type (Patnaik II type). Canine patient 7 visited again for follow-up on Mar. 10, 2008 and was subjected to serodiagnosis again. As a result, absorbance at 450 nm was found to be 0.07. At this time, neither metastasis nor recurrence was confirmed. Thus, in the case of canine patient 7, it can be said that the serodiagnosis results were lower than those upon surgery since the tumor could be completely resected.

(2)-5 Recurrence Diagnosis

Canine patient 8 (Husky) had extirpative surgery on May 8, 2007, for breast adenocarcinoma. As a result of serodiagnosis performed at this time, absorbance at 450 nm was found to be 0.05. As a result of pathologic diagnosis using excised tissue, strongly atypical epithelial cells grew mainly forming a tubular structure. Thus, canine patient 8 was diagnosed as having adenocarcinoma from the primary mammary gland. At this time, the presence of many cancer cells in lymph ducts had already been confirmed, indicating a high risk of metastasis to or recurrence at the lymph nodes or distant sites. On Jun. 28, 2007, (about 1 and a half months after surgery), recurrence was confirmed at the same site. The result of serodiagnosis at this time was 0.09, and thus an increased value was confirmed. In the case of canine patient 8, it was revealed that because of incomplete tumor resection or recurrence thereof, the diagnostic results were higher in late June than in early May.

(2)-6 Diagnosis of Metastasis

Canine patient 9 (Scottish terrier) experienced multiple metastases and recurrences, including a mammary gland tumor in February 2003, intraoral malignant melanoma in August 2003, labial malignant melanoma in January 2005, and intraoral melanoma on Apr. 13, 2005. All of these tumors had been resected by surgery. Canine patient 9 revisited the hospital on Dec. 17, 2006, for follow-up after the recurrence of intraoral melanoma on April 2005 and was subjected to serodiagnosis. As a result, absorbance at 450 nm was found to be 0.09. Half a year later, canine patient 9 revisited the hospital on Jun. 20, 2007 because of cervical lymphoid and popliteal lymphoid hyperplasia. In the case of lymphoma, the lymph nodes swell up systemically. Canine patient 9 had swelling lymph nodes at only two sites. Hence, canine patient 9 was clinically diagnosed as likely to have lymphoma due to metastasis. Diagnosis made by this technique also revealed that absorbance at 450 nm was increased to 0.10, indicating that the lymphoma was caused by metastasis from the previous tumor.

Canine patient 10 (Shiba inu) underwent tumorectomy on Mar. 11, 2006, because of intraoral malignant melanoma of the right lip. Canine patient 10 had a history of treatment with an anticancer agent (cyclophosphamide) from Jun. 10, 2006, to Sep. 26, 2006, and had been under medication with BIREMO S having organic germanium as a major ingredient since May 23, 2006. Serodiagnosis was made on Mar. 20, 2007, upon the removal of a tumor thought to have resulted from metastasis of the previous tumor, so that the absorbance at 450 nm was found to be almost 0.03, indicating almost no detection. Pathologic diagnosis was made for the tissue excised at this time so that the disease was diagnosed as metastatic malignant melanoma. However, metastasis occurred again on Jun. 27, 2007, 3 months after surgery for metastatic melanoma. A tumor developed at the right portion of the cervix on Mar. 20, 2007, and further tumor development occurred on the side opposite to such portion on Jun. 27, 2007. The tumors formed black masses analogous to those of the previous findings. Tumor size was 3.1×3.2×0.8 cm, and the tumors were clinically diagnosed as metastatic tumors. As a result of serodiagnosis at this time, absorbance at 450 nm was confirmed to have increased to 0.23, suggesting that the tumors resulted from metastasis of previous tumors.

(2)-7 Cancer Diagnosis Using Human CAPRIN-1-Derived Polypeptide

With the use of the polypeptide (SEQ ID NO: 2) of human CAPRIN-1 prepared in Example 2, the titer of canine serum IgG antibody reacting with the polypeptide was measured in a manner similar to that used above. As a result of examination using serum of a healthy dog, almost no absorbance was detected at 450 nm, similarly to the case above.

Meanwhile, canine patient 11 (Shih tzu) had extirpative surgery for breast adenocarcinoma on Jun. 21, 2007. As a result of pathologic diagnosis using excised tissues, canine patient 11 was diagnosed as having breast adenocarcinoma of moderate malignancy, wherein strongly atypical and invasive mammary gland tissues underwent adenoid-tubular-papillary growth so as to form large and small masses, in addition to the presence of somewhat diffuse hyperplasia of fibrillar connective tissues. The absorbance at 450 nm for canine patient 11 was found to be 0.26.

(3) Feline Cancer Diagnosis

Next, cancer-bearing cats and healthy cats were diagnosed. With the use of the polypeptide of canine CAPRIN-1 (used above) and an anti-feline IgG antibody, the titer of feline serum IgG antibody specifically reacting with the polypeptide was measured, in a manner similar to the above. As a secondary antibody, an HRP modified anti-feline IgG antibody (PEROXIDASE-CONJUGATED GOAT IgG FRACTION TO CAT IgG (WHOLE MOLECULE): CAPPEL RESEARCH REAGENTS) was diluted 8000-fold with a blocking solution and then used.

Feline patient 1 (mongrel) had tumor extirpative surgery for breast adenocarcinoma on May 8, 2007. The absorbance at 450 nm for feline patient 1 was found to be 0.21. Also, in the case of feline patient 2 (Himalayans) that had extirpative surgery for ductal carcinoma on Oct. 17, 2006, the absorbance at 450 nm was found to be 0.18. On the other hand, no absorbance was detected in the case of healthy cats.

Also, with the use of the polypeptide (SEQ ID NO: 2) of human CAPRIN-1 prepared in Example 2, the titer of feline serum IgG antibody reacting with the polypeptide was measured in a manner similar to the above. As a result, in the case of healthy cats, almost no absorbance was detected at 450 nm when the polypeptide had been immobilized. Meanwhile, feline patient 3 (American Shorthair) had extirpative surgery for breast adenocarcinoma on Apr. 15, 2008. As a result of pathologic diagnosis using excised tissues, feline patient 3 was diagnosed as having highly malignant breast adenocarcinoma associated with large and small dead tissues, wherein strongly atypical and invasive mammary gland tissues underwent sheet-like growth into large and small masses. Also in the case of feline patient 3, the absorbance at 450 nm was found to be 0.12.

Therefore, it was demonstrated that cancer diagnosis is also possible for cats by this technique, similarly to dogs, since values were detected for specimens from cats with cancer, but none was detected for specimens from healthy cats.

(4) Human Cancer Diagnosis

With the use of the polypeptide (SEQ ID NO: 2) of human CAPRIN-1 prepared in Example 2 and an anti-human IgG antibody, the titer of a healthy human serum IgG antibody specifically reacting with the polypeptide was measured. Immobilization of the prepared polypeptide was performed by adding a recombinant protein solution diluted to 100 μg/mL with phosphate buffered saline to 96-well immobilizer amino plates (Nunc) at 100 μl/well and then leaving the plates to stand overnight at 4° C. Blocking was performed as follows. Four gram of Block Ace powder (DS PHARMA BIOMEDICAL Co., Ltd.) was dissolved in 100 ml of purified water and then the solution was diluted 4-fold with purified water. Then the solution (hereinafter, blocking solution) was added at 100 μl/well and then shaken at room temperature for 1 hour. Serum diluted 1000-fold with the blocking solution was added at 100 μl/well and then shaken at room temperature for 3 hours for reaction. After washing 3 instances with phosphate buffered saline (hereinafter, PBS-T) containing 0.05% Tween20 (Wako Pure Chemical Industries, Ltd.), an HRP-modified anti-human IgG antibody (HRP-Goat Anti-Human IgG (H+L) Conjugate: Zymed Laboratories) diluted 10000-fold with the blocking solution was added at 100 μl/well and then shaken at room temperature for 1 hour for reaction. After 3 instances of washing with PBS-T, HRP substrate TMB (1-Step Turbo TMB (tetramethylbenzidine), PIERCE) was added at 100 μl/well and then an enzyme-substrate reaction was performed at room temperature for 30 minutes. Subsequently, a 0.5 M sulfuric acid solution (Sigma Aldrich Japan) was added at 100 μl/well to stop the reaction and then absorbance at 450 nm was measured using a microplate reader. An ovalbumin antigen adjusted to 50 μg/ml with phosphate buffered saline was immobilized and then used as a positive control. As a result, absorbance at 450 nm was found to be as high as 0.45 on average as the results for 7 healthy subjects in the case of the ovalbumin antigen, but no absorbance (0) was detected in the case of the above polypeptide.

In a manner similar to the above, 17 serum specimens (purchased from ProMedDx) from patients with malignant breast cancer were further subjected to measurement of the titer of serum IgG antibody specifically reacting with the human-derived cancer antigen protein (the amino acid sequence of SEQ ID NO: 3). As a result, absorbance at 450 nm was found to be as high as 0.48 in the case of the above polypeptide, on average as the results for 17 breast cancer patients.

Also, with the use of the polypeptide (SEQ ID NO: 8) of canine CAPRIN-1 prepared in Example 2 and an anti-human IgG antibody, the titer of human serum IgG antibody specifically reacting with the polypeptide was measured in a manner similar to that above. As a result, whereas the average of the results for 7 healthy subjects was 0.04, the average of the results for 17 breast cancer patients was as high as 0.55.

Based on the above results, it was demonstrated that cancer in humans can also be detected by this technique.

Example 5: Cancer Diagnosis Through Measurement of Antigen Polypeptide

With the use of the polyclonal antibody against CAPRIN-1-derived peptide (SEQ ID NO: 43) obtained in Example 3 (1) and each monoclonal antibody against the CAPRIN-1 protein obtained in Example 3 (2) in combination, the antigen polypeptide itself contained in specimens (cancer-bearing living organism-derived serum) reacted positive upon cancer diagnosis using the polypeptide of CAPRIN-1 in Example 4 (1)-(3) was detected by Sandwich ELISA. The polyclonal antibody was used as a primary antibody and each monoclonal antibody was used as a secondary antibody. The serum protein level of the protein specifically reacting with each of the above antibodies was measured.

The primary antibody was immobilized by adding the polyclonal antibody diluted to a concentration of 5 μg/ml with phosphate buffered saline to 96-well immobilizer amino plates (Nunc) at 100 μl/well and then shaking the plates at room temperature for 2 hours. Blocking was performed by adding a 50 mM sodium bicarbonate buffer solution (pH 8.4) (hereinafter, blocking solution) containing 0.5% BSA (bovine serum albumin, Sigma Aldrich Japan) at 100 μl/well and then shaking at room temperature for 1 hour. Subsequently, a cancer-bearing living organism-derived serum diluted using the blocking solution was added at 100 μl/well and then the resultants were shaken at room temperature for 3 hours for reaction. The dilution rate at this time was adjusted with 10-fold (10-1000-fold) dilution series. After 3 instances of washing with phosphate buffered saline (hereinafter, PBS-T) containing 0.05% Tween20 (Wako Pure Chemical Industries, Ltd.), each monoclonal antibody as a secondary antibody diluted to a concentration of 1 μg/ml with the blocking solution was added at 100 μl/well and then the resultants were shaken at room temperature for 1 hour for reaction. After 3 instances of washing with PBS-T, an HRP-labeled anti-mouse IgG (H+L) antibody (Invitrogen Corporation) as a tertiary antibody diluted 5000-fold with the blocking solution was added at 100 μl per well and then left to stand at room temperature for 1 hour. After 3 instances of washing of wells with PBS-T, a TMB substrate solution (Thermo) was added at 100 μl per well and then left to stand for 15-30 minutes for color reaction. After color development, 1 N sulfuric acid was added at 100 μl per well to stop the reaction and then absorbance at 450 nm was measured using an absorption spectrometer.

As a result, when the #1-#10 monoclonal antibodies reacting with the surfaces of cancer cells were used as secondary antibodies, absorbance values (polypeptide levels) of 0.3 or higher were detected for all specimens from cancer-bearing dogs and cancer-bearing cats with breast cancer, malignant melanoma, and the like, but no absorbance was detected for healthy dogs and healthy cats. On the other hand, when monoclonal antibodies reacting with the CAPRIN-1 protein itself but not reacting with the surfaces of cancer cells were used as secondary antibodies, polypeptide levels were detected for all specimens, but absorbance values were all 0.05 or less, which were lower than the results for combinations of antibodies reacting with the surfaces of cancer cells.

Therefore, cancer can also be diagnosed by this technique that involves detection of antigen polypeptides using antibodies against CAPRIN-1.

INDUSTRIAL APPLICABILITY

The present invention is industrially useful for diagnosis or detection of cancer.

This description includes part or all of the contents as disclosed in the description and/or drawings of Japanese Patent Application No. 2008-202320, which is a priority document of the present application. Also, all publications, patents, and patent applications cited herein are incorporated herein by reference in their entirety.

SEQUENCE LISTING FREE TEXT

SEQ ID NOS: 31-42: primers

The invention claimed is:

1. A method for detecting a cancer, comprising:

obtaining an antibody or antigen binding fragment thereof which binds a CAPRIN-1 protein having any one of the amino acid sequences shown in the even-numbered SEQ ID NOS: 2-30 in the Sequence Listing by selecting by screening antibodies isolated against CAPRIN-1 protein for binding to CAPRIN-1 protein on a surface of a cancer cell, detecting a CAPRIN-1 protein expression on a surface of a cell in a sample from a human by utilizing the antibody or antigen binding fragment thereof, identifying the human as having cancer by detecting the CAPRIN-1 expression on the surface of the cell in the sample separated from the human, and treating the human for the cancer, wherein the treatment comprises an anticancer agent, hormone therapy, radiotherapy and/or surgery.

2. The method according to claim 1, wherein the CAPRIN-1 protein to be measured is a CAPRIN-1 protein having any one of the amino acid sequences shown in the even-numbered SEQ ID NOS: 2-30 or a polypeptide having 85% or more sequence identity with the CAPRIN-1 protein.

3. The method according to claim 1, wherein the sample is serum or blood plasma.

4. The method according to claim 1 further comprising detecting the malignancy of a cancer based on the fact that the malignancy of cancer is high when the expression level of the CAPRIN-1 protein is higher than that of a control.

5. The method according to claim 1 further comprising detecting the progression of cancer on the basis of the indicator that the extent of cancer is advanced when the expression level of the CAPRIN-1 protein is higher than that of a control.

6. The method according to claim 1, wherein the cancer is at least one type of cancer selected from the group consisting of brain tumor, squamous cell carcinoma of the head, neck, lung, uterus or esophagus, melanoma, adenocarcinoma of the lung or uterus, renal cancer, malignant mixed tumor, hepatocellular carcinoma, basal cell carcinoma, acanthoma-like gingival tumor, tumor of the oral cavity, perianal adenocarcinoma, anal sac tumor, anal sac apocrine adenocarcinoma, sertoli cell carcinoma, cancer of vaginal vestibule, sebaceous adenocarcinoma, sebaceous epithelioma, sebaceous adenoma, sweat gland carcinoma, intranasal adenocarcinoma, nasal adenocarcinoma, thyroid cancer, large-bowel cancer, bronchial adenocarcinoma, adenocarcinoma, ductal carcinoma, breast adenocarcinoma, composite type breast adenocarcinoma, malignant mammary mixed tumor, intraductal papillary adenocarcinoma, fibrosarcoma, hemangiopericytoma, osteosarcoma, chondrosarcoma, soft tissue sarcoma, histiocytic sarcoma, myxosarcoma, undifferentiated sarcoma, lung cancer, mastocytoma, cutaneous leiomyoma, intraperitoneal leiomyoma, leiomyoma, chronic lymphocytic leukemia, lymphoma, gastrointestinal lymphoma, digestive lymphoma, small-cell-to-medium-cell lymphoma, adrenomedullary tumor, granulosa cell tumor, and pheochromocytoma.

7. The method according to claim 1, wherein the antibody or antigen binding fragment thereof specifically binds a fragment of the CAPRIN-1 protein consisting of the amino acid sequence shown in SEQ ID NO: 43 or 61.

8. The method according to claim 1, wherein the cancer is breast cancer.

9. A method for detecting a cancer, comprising:

obtaining an antibody or antigen binding fragment thereof which binds a CAPRIN-1 protein having any one of the amino acid sequences shown in the even-numbered SEQ ID NOS: 2-30 in the Sequence Listing by selecting by screening antibodies isolated against CAPRIN-1 protein for binding to CAPRIN-1 protein on a surface of a cancer cell, contacting a cell separated from a human with the antibody or antigen-binding fragment thereof, detecting a CAPRIN-1 protein expression on the surface of the cell separated from the human, identifying the human as having cancer by detecting the CAPRIN-1 protein expression on the surface of the cell separated from the human, and treating the human for the cancer, wherein the treatment comprises an anticancer agent, hormone therapy, radiotherapy and/or surgery.

10. The method according to claim 9, wherein the antibody or an antigen-binding fragment thereof which specifically binds a CAPRIN-1 protein expressed on the cell surface of a cancer cell specifically binds a fragment of the CAPRIN-1 protein consisting of the amino acid sequence shown in SEQ ID NO: 43 or 61.

11. The method according to claim 9, wherein the cancer is breast cancer.

12. The method according to claim 9, wherein the cancer is at least one type of cancer selected from the group consisting of brain tumor, squamous cell carcinoma of the head, neck, lung, uterus or esophagus, melanoma, adenocarcinoma of the lung or uterus, renal cancer, malignant mixed tumor, hepatocellular carcinoma, basal cell carcinoma, acanthoma-like gingival tumor, tumor of the oral cavity, perianal adenocarcinoma, anal sac tumor, anal sac apocrine adenocarcinoma, sertoli cell carcinoma, cancer of vaginal vestibule, sebaceous adenocarcinoma, sebaceous epithelioma, sebaceous adenoma, sweat gland carcinoma, intranasal adenocarcinoma, nasal adenocarcinoma, thyroid cancer, large-bowel cancer, bronchial adenocarcinoma, adenocarcinoma, ductal carcinoma, breast adenocarcinoma, composite type breast adenocarcinoma, malignant mammary mixed tumor, intraductal papillary adenocarcinoma, fibrosarcoma, hemangiopericytoma, osteosarcoma, chondrosarcoma, soft tissue sarcoma, histiocytic sarcoma, myxosarcoma, undifferentiated sarcoma, lung cancer, mastocytoma, cutaneous leiomyoma, intraperitoneal leiomyoma, leiomyoma, chronic lymphocytic leukemia, lymphoma, gastrointestinal lymphoma, digestive lymphoma, small-cell-to-medium-cell lymphoma, adrenomedullary tumor, granulosa cell tumor, and pheochromocytoma.

13. A method for detecting a cancer, comprising:

obtaining an antibody or antigen binding fragment thereof which binds a CAPRIN-1 protein by selecting by screening antibodies isolated against CAPRIN-1 protein for binding to CAPRIN-1 protein on a surface of a cancer cell, detecting a CAPRIN-1 protein expression on a surface of a cell in a sample from a human by utilizing the antibody or antigen binding fragment thereof, identifying the human as having cancer by detecting the CAPRIN-1 protein expression on the surface of the cell separated from the human, and treating the human for the cancer, wherein the treatment comprises an anticancer agent, hormone therapy, radiotherapy and/or surgery.

14. The method according to claim 13, wherein the antibody or antigen binding fragment thereof specifically binds a fragment of the CAPRIN-1 protein consisting of the amino acid sequence shown in SEQ ID NO: 43 or 61.

15. The method according to claim 13, wherein the cancer is breast cancer.

16. The method according to claim 13, wherein the cancer is at least one type of cancer selected from the group consisting of brain tumor, squamous cell carcinoma of the head, neck, lung, uterus or esophagus, melanoma, adenocarcinoma of the lung or uterus, renal cancer, malignant mixed tumor, hepatocellular carcinoma, basal cell carcinoma, acanthoma-like gingival tumor, tumor of the oral cavity, perianal adenocarcinoma, anal sac tumor, anal sac apocrine adenocarcinoma, sertoli cell carcinoma, cancer of vaginal vestibule, sebaceous adenocarcinoma, sebaceous epithelioma, sebaceous adenoma, sweat gland carcinoma, intranasal adenocarcinoma, nasal adenocarcinoma, thyroid cancer, large-bowel cancer, bronchial adenocarcinoma, adenocarcinoma, ductal carcinoma, breast adenocarcinoma, composite type breast adenocarcinoma, malignant mammary mixed tumor, intraductal papillary adenocarcinoma, fibrosarcoma, hemangiopericytoma, osteosarcoma, chondrosarcoma, soft tissue sarcoma, histiocytic sarcoma, myxosarcoma, undifferentiated sarcoma, lung cancer, mastocytoma, cutaneous leiomyoma, intraperitoneal leiomyoma, leiomyoma, chronic lymphocytic leukemia, lymphoma, gastrointestinal lymphoma, digestive lymphoma, small-cell-to-medium-cell lymphoma, adrenomedullary tumor, granulosa cell tumor, and pheochromocytoma.

* * * * *